United States Patent
Shinohata et al.

(10) Patent No.: US 8,362,293 B2
(45) Date of Patent: *__Jan. 29, 2013__

(54) PROCESS FOR PRODUCING ISOCYANATES

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/521,077

(22) PCT Filed: Jan. 10, 2008

(86) PCT No.: PCT/JP2008/050171
§ 371 (c)(1),
(2), (4) Date: Jun. 24, 2009

(87) PCT Pub. No.: WO2008/084824
PCT Pub. Date: Jul. 17, 2008

(65) Prior Publication Data
US 2010/0069665 A1    Mar. 18, 2010

(30) Foreign Application Priority Data

| Jan. 11, 2007 | (JP) | 2007-003242 |
| Jan. 11, 2007 | (JP) | 2007-003244 |
| Jan. 11, 2007 | (JP) | 2007-003245 |

(51) Int. Cl.
*C07C 263/00* (2006.01)
(52) U.S. Cl. ........................................ 560/345
(58) Field of Classification Search ................ None
See application file for complete search history.

(56) References Cited

U.S. PATENT DOCUMENTS

| 2,692,275 | A |   | 10/1954 | Bortnick |
| 3,125,598 | A |   | 3/1964 | Kuhle et al. |
| 3,734,941 | A |   | 5/1973 | Sydor |
| 3,992,430 | A | * | 11/1976 | Bacskai .......................... 560/345 |
| 4,081,472 | A |   | 3/1978 | Tsumura et al. |
| 4,097,676 | A |   | 6/1978 | Romano |
| 4,123,450 | A |   | 10/1978 | Weber, Jr. |
| 4,290,970 | A |   | 9/1981 | Merger et al. |
| 4,354,979 | A | * | 10/1982 | Schwendemann et al. ... 560/344 |

(Continued)

FOREIGN PATENT DOCUMENTS

| CN | 1419538 A | 2/2001 |
| DE | 925496 | 3/1955 |

(Continued)

OTHER PUBLICATIONS

Xylenol printout http://en.wikipedia.org/wiki/Xylenol.*

(Continued)

*Primary Examiner* — Johann Richter
*Assistant Examiner* — Jennifer C Sawyer
(74) *Attorney, Agent, or Firm* — Morgan, Lewis & Bockius LLP

(57) ABSTRACT

An object of the present invention is to provide a process allowing long-term, stable production of isocyanates at a high yield without the various problems found in the prior art during production of isocyanates without using phosgene. The present invention discloses a process for producing an isocyanate by subjecting a carbamic acid ester to a decomposition reaction in the presence of a compound having an active proton and a carbonic acid derivative.

18 Claims, 4 Drawing Sheets

U.S. PATENT DOCUMENTS

| | | | |
|---|---|---|---|
| 4,386,033 A | 5/1983 | Konig et al. | |
| 4,388,238 A | 6/1983 | Heitkamper et al. | |
| 4,388,246 A | 6/1983 | Sundermann et al. | |
| 4,388,426 A | 6/1983 | Schure et al. | |
| 4,430,505 A | 2/1984 | Heitkamper et al. | |
| 4,480,110 A | 10/1984 | Heitkamper et al. | |
| 4,482,499 A | 11/1984 | Merger et al. | |
| 4,497,963 A | 2/1985 | Merger et al. | |
| 4,514,339 A | 4/1985 | Romano et al. | 260/453 P |
| 4,596,678 A | 6/1986 | Merger et al. | |
| 4,596,679 A | 6/1986 | Hellbach et al. | |
| 4,613,466 A | 9/1986 | Merger et al. | |
| 4,659,845 A | 4/1987 | Rivetti et al. | |
| 4,692,550 A | 9/1987 | Engbert et al. | |
| 4,925,971 A | 5/1990 | Aoki et al. | |
| 5,087,739 A | 2/1992 | Bohmholdt et al. | |
| 5,315,034 A | 5/1994 | Mizia et al. | |
| 5,386,053 A | 1/1995 | Otterbach et al. | |
| 5,502,244 A | 3/1996 | Okawa et al. | |
| 5,616,784 A | 4/1997 | Schwarz et al. | |
| 5,883,291 A * | 3/1999 | Schleenstein et al. | 560/345 |
| 6,143,917 A | 11/2000 | Harada et al. | |
| 6,222,065 B1 | 4/2001 | Okawa et al. | 560/338 |
| 6,992,214 B2 | 1/2006 | Cesti et al. | |
| 7,446,218 B2 | 11/2008 | Miyake et al. | |
| 2003/0055282 A1 | 3/2003 | Bosman et al. | |
| 2005/0080274 A1 | 4/2005 | Miyake et al. | |
| 2007/0055042 A1 | 3/2007 | Miyake et al. | 528/196 |
| 2008/0275262 A1 | 11/2008 | Miyake et al. | |
| 2010/0029981 A1 | 2/2010 | Shinohata et al. | |
| 2010/0069665 A1 | 3/2010 | Shinohata et al. | |
| 2011/0054211 A1 | 3/2011 | Shinohata et al. | |
| 2011/0092731 A1 | 4/2011 | Shinohata et al. | |

FOREIGN PATENT DOCUMENTS

| | | |
|---|---|---|
| EP | 1 640 357 A1 | 11/1984 |
| EP | 0125 726 A1 | 11/1984 |
| EP | 0320235 A | 6/1989 |
| EP | 0355443 A | 2/1990 |
| EP | 0446514 A1 | 9/1991 |
| EP | 0957073 A1 | 11/1999 |
| GB | 1217122 | 12/1970 |
| JP | 46-27593 B1 | 8/1971 |
| JP | 52-71443 A | 6/1977 |
| JP | 52-136147 A | 11/1977 |
| JP | 57-159752 A | 10/1982 |
| JP | 59-108754 | 6/1984 |
| JP | 59-108754 A | 6/1984 |
| JP | 60-231640 A | 11/1985 |
| JP | 61-183257 A | 8/1986 |
| JP | 1-230550 A | 9/1989 |
| JP | 4-26665 A | 1/1992 |
| JP | 6-25136 A | 2/1994 |
| JP | 3382289 B | 2/1994 |
| JP | 06-056984 A | 3/1994 |
| JP | 06-192204 A | 7/1994 |
| JP | 07-258194 | 10/1995 |
| JP | 7-258194 A | 10/1995 |
| JP | 09-087239 | 3/1997 |
| JP | 09087239 A | 3/1997 |
| JP | 10-316645 A | 12/1998 |
| JP | 11-5774 A | 1/1999 |
| JP | 2000-344730 | 12/2000 |
| JP | 2000-344730 A | 12/2000 |
| JP | 3238201 B | 10/2001 |
| JP | 2001-323106 A | 11/2001 |
| JP | 2002-500654 A | 1/2002 |
| JP | 2003-055332 A | 2/2003 |
| JP | 2003-525267 A | 8/2003 |
| JP | 2004-244349 A | 9/2004 |
| JP | 2004-262834 A | 9/2004 |
| JP | 2004-262835 A | 9/2004 |
| JP | 2006-069941 A | 3/2006 |
| WO | 95/23484 A1 | 8/1995 |
| WO | 98/54128 A1 | 12/1998 |
| WO | 03/055840 A1 | 7/2003 |
| WO | 2004-014840 A1 | 2/2004 |
| WO | 2005/111049 A1 | 11/2005 |

OTHER PUBLICATIONS

Berchte der Deutechen Chemischen Gesellschaft, vol. 3, p. 653, 1870.

Elizabeth Dyer et al., "Thermal Degradation of Alkyl N-Phenylcarbamates", Journal of the American Chemical Society, vol. 81, p. 2138-2143, 1959.

D.S. Tarbell et al., "Acidic and Basic Catalysis in Urethan Formation", Journal of the American Chemical Society, vol. 64 (9), p. 2229-2230, 1942.

English translation of IPRP for PCT/JP2008/058952.

Kosa et al. (2004) New combined phenol-hindered amine stabilizers for polymers based on diphenylmethane-4,4'-diisocyanate and dicyclohexylmethane-4,4'-diisocyanate, Polymer Degradation and Stability 86:391-400.

Habicher et al. (2001) Synthesis and Antioxidative Properties of Novel Multifunctional Stabilizers, J. of Vinyl & Additive Technology, 7:4-18.

Kovacic et al. (1966) Reactions of t-Butylperoxy Isopropyl Carbonate with Aromatic Compounds under Friedel-Crafts Conditions, J. Organic Chem. 31:2459-2467.

Petersen (1949) Polyurethans. V. Low-molecular Conversion of Products of Diisocyanates, Ann. 562:205-229.

Yamazaki et al. (1979) The Reaction of Diphenyl Carbonate with Amines and Its Application to Polymer Synthesis, J. Polymer Sci. 17:835-841.

Kagaku Dai Jiten Henshu linkai, Kagaku Dai Jiten 7 (1989) vol. 32, Kyoritsu Shuppan Co., Ltd., pp. 725-728.

Leuckart (1890) Ueber Einige Synthesen Mittelst Phenylcyanat, J. fur Praktische Chemie, 41:301-329.

OHME (1971) Synthesen mit Brenzacatechincarbonat, J. fur Praktische Chemie, 313:626-635.

STN Accession No. 127:247849 CASREACT structure diagram for Schleenstein et al US5883291.

English translation of IPRP for PCT/JP2007/072268.

Supplementary European Search Report for EP 07831998.

English translation of IPR for PCT/JP2008/058952.

* cited by examiner

PROCESS FOR PRODUCING ISOCYANATES

TECHNICAL FIELD

The present invention relates to a process for producing isocyanates.

BACKGROUND ART

Isocyanates are widely used as production raw materials of products, such as polyurethane foams, paints and adhesives. The main industrial production process of isocyanates includes reacting amine compounds with phosgene (phosgene method), and nearly the entire amount of isocyanates produced throughout the world are produced according to the phosgene method. However, the phosgene method has numerous problems.

Firstly, this method requires the use of a large amount of phosgene as raw material. Phosgene is extremely toxic and requires special handling precautions to prevent exposure of handlers thereof, and also requires special apparatuses to detoxify waste.

Secondly, since highly corrosive hydrogen chloride is produced in large amounts as a byproduct of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a process for producing isocyanates has been sought that does not use phosgene. One example of a method for producing isocyanate compounds without using phosgene that has been proposed involves thermal decomposition of carbamic acid esters. Isocyanates and hydroxy compounds have long been known to be obtained by thermal decomposition of carbamic acid esters (see, for example, Non-Patent Document 1). The basic reaction is illustrated by the following formula:

$$R(NHCOOR')_a \rightarrow R(NCO)_a + aR'OH \quad (1)$$

(wherein R represents an organic residue having a valence of a, R' represents a monovalent organic residue, and a represents an integer of 1 or more).

On the other hand, thermal decomposition of carbamic acid esters is susceptible to the simultaneous occurrence of various irreversible side reactions such as thermal denaturation reactions undesirable for carbamic acid esters or condensation of isocyanates formed by the thermal decomposition. Examples of these side reactions include a reaction in which urea bonds are formed as represented by the following formula (2), a reaction in which carbodiimides are formed as represented by the following formula (3), and a reaction in which isocyanurates are formed as represented by the following formula (4) (see, Non-Patent Document 1 and Non-Patent Document 2).

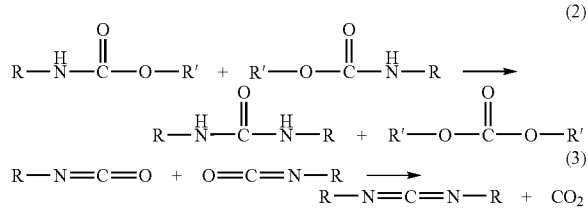

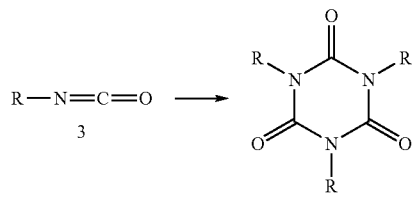

In addition to these side reactions leading to a decrease in yield and selectivity of the target isocyanate, in the production of polyisocyanates in particular, these reactions may make long-term operation difficult as a result of, for example, causing the precipitation of polymeric solids that clog the reaction vessel.

Various methods have been proposed for producing isocyanates that do not contain phosgene.

According to the description of Patent Document 1, an aliphatic diurethane and/or alicyclic diurethane and/or aliphatic polyurethane and/or alicyclic polyurethane are obtained by reacting an aliphatic primary diamine and/or alicyclic primary diamine and/or aliphatic primary polyamine and/or alicyclic primary polyamine in the presence of an O-alkylcarbamate and alcohol and in the presence or absence of a catalyst at 160 to 300° C. at a ratio of amine $NH_2$ group:carbamate:alcohol of 1:0.8 to 10.0:0.25 to 50, and removing the ammonia formed as necessary. The resulting diurethane and/or polyurethane can be converted to the corresponding diisocyanate and/or highly functional polyisocyanate as necessary. The detailed reaction conditions for the thermal decomposition are not described in this patent publication.

According to the description of Patent Document 2, an aromatic diisocyanate and/or polyisocyanate are produced by going through the following two steps. In the first step, an aromatic primary amine and/or an aromatic primary polyamine are reacted with an O-alkylcarbamate in the presence or absence of a catalyst and in the presence or absence of urea and alcohol to form an aryl diurethane and/or aryl polyurethane followed by removal of the ammonia formed as necessary. In the second step, an aromatic isocyanate and/or aromatic polyisocyanate are obtained by thermal decomposition of the aryl diurethane and/or aryl polyurethane.

Other publications contain descriptions relating to partial substitution of urea and/or diamine by a carbonyl-containing compound such as N-substituted carbamate and/or dialkylcarbamate, or mono-substituted urea, di-substituted urea, mono-substituted polyurea or di-substituted polyurea (see Patent Document 3, Patent Document 4, Patent Document 5, Patent Document 6 and Patent Document 7). Patent Document 8 describes a method for producing aliphatic O-aryl urethanes by reacting (cyclic) aliphatic polyamines with urea and aromatic hydroxy compounds.

There are several known methods for forming corresponding isocyanates and alcohols by thermal decomposition of (cyclic) aliphatic, and particularly aromatic, monourethanes and diurethanes, including methods carried out in the vapor phase at a high temperature, and methods carried out in a liquid phase under comparatively low temperature conditions. In these methods, however, the reaction mixture gives rise to the side reactions described above, thereby causing, for example, the formation of sediment, polymeric substances and obstructions in the reaction vessel and recovery apparatus, or the formation of substances that adhere to the sidewalls of the reaction vessel, thereby resulting in poor economic efficiency in the case of producing isocyanates over a long period of time.

Thus, the use of a chemical method, such as the use of a special catalyst (see Patent document 9 and Patent Document 10) or a catalyst combined with an inert solvent (see Patent Document 11), has been disclosed to improve the yield in the thermal decomposition of urethane.

For example, Patent document 12 describes a process for producing hexamethylene diisocyanate including thermal decomposition of hexamethylene diethyl urethane in the presence of dibenzyl toluene used as a solvent and in the presence of a catalyst mixture composed of methyl toluene sulfonate and diphenyl tin dichloride. However, since there are no detailed descriptions of production or isolation of the starting components or purification and arbitrary recovery of the solvent and catalyst mixture, the economic efficiency of this process could not be evaluated.

According to the method described in Patent Document 13, urethane can be easily broken down into isocyanate and alcohol in a carbon-containing fluidized bed without using a catalyst. In addition, according to the description of Patent document 14, hexamethylene dialkyl urethane can be decomposed in the gaseous phase at a temperature in excess of 300° C. in the presence or absence of a gas permeable packaging material made of, for example, carbon, copper, brass, steel, zinc, aluminum, titanium, chromium, cobalt or quartz to form hexamethylene diisocyanate.

In addition, according to the description of Patent Document 14, this method is carried out in the presence of a hydrogen halide and/or hydrogen halide donor. However, this method is unable to achieve a yield of hexamethylene diisocyanate of 90% or more. This is because the decomposition products are partially recombined resulting in the formation of urethane bonds. Thus, the hexamethylene is required to be additionally purified by distillation, which frequently increases yield loss.

Moreover, according to the description of Patent Document 15, a monocarbonate is disclosed to be able to be decomposed with favorable yield and in the absence of a solvent and in the presence or absence of a catalyst and/or stabilizer at a comparatively low temperature and advantageously under reduced pressure. The decomposition products (monoisocyanate and alcohol) are removed from a boiling reaction mixture by distillation and separately captured by separative condensation. A method for removing byproducts formed during thermal decomposition including partially removing the reaction mixture outside the system is described in a generic form. Thus, although byproducts can be removed from the bottom of the reaction vessel, problems remain with respect to the case of adherence to the sidewalls of the reaction vessel as previously described, and problems with respect to long-term operation remain unsolved. In addition, there is no description regarding industrial utilization of the removed reaction mixture (containing large amounts of useful components).

According to the description of Patent Document 16, thermal decomposition of aliphatic, alicyclic or aromatic polycarbamates is carried out in the presence of an inert solvent at 150 to 350° C. and 0.001 to 20 bar, and in the presence or absence of a catalyst, and an assistant in the form of hydrogen chloride, organic acid chloride, alkylation agent or organic tin chloride. Byproducts formed, can be continuously removed from the reaction vessel together with the reaction solution, for example, and a corresponding amount of fresh solvent or recovered solvent can is added simultaneously. A shortcoming of this method is, for example, a reduction in the space-time yield of polyisocyanates as a result of using a refluxing solvent, while also requiring considerable energy, including that for recovery of the solvent. Moreover, the assistants used are volatile under the reaction conditions, resulting in the potential for contamination of the decomposition products. In addition, the amount of residue is large based on the formed polyisocyanate, thus leaving room for doubt regarding economic efficiency and the reliability of industrial methods.

According to the description of Patent Document 17, a method is described for continuous thermal decomposition of a carbamate such as the cyclic diurethane, 5-(ethoxycarbonylamino)-1-(ethoxycarbonylaminomethyl)-1,3,3-trimethyl-cyclohexane, supplied along the inner surface of a tubular reaction vessel in a liquid form in the presence of a high boiling point solvent. This method has the shortcomings of low yield during production of (cyclic) aliphatic diisocyanates and low selectivity. In addition, there is no description of a continuous method accompanying recovery of recombined or partially decomposed carbamates, while there is also no mention made of post-treatment of solvent contained in the byproducts and catalyst.

According to Patent Document 18, a circulation process is disclosed for producing (cyclic) aliphatic diisocyanates by converting corresponding diamines to diurethane followed by thermal decomposition of this urethane. This process minimizes reductions in yield by recirculating the product of the urethane decomposition step following reaction with alcohol to a urethanation step. Byproducts unable to be recirculated are removed by separation by distillation of the mixture of urethanation products, and in this case, a valueless residue is formed in the form of bottom products, while all comparatively low boiling point components, including diurethane, are removed from the top of the column. However, this process has the shortcoming of using a large amount of energy. This is because all of the diurethane must be evaporated in the presence of catalyst, and this diurethane must be evaporated at a temperature level within the range of the decomposition temperature of urethane. Moreover, isocyanate groups formed in useful products react with residue urethane groups, frequently resulting in the formation of comparatively high molecular weight byproducts that lower yield.

In addition, according to the description of Patent Document 19, a method is disclosed for partially removing valueless byproducts outside the system during thermal decomposition of polyurethane. A shortcoming of this method is that isocyanate yield decreases due to polyurethane ending up being contained in byproducts partially removed outside the system. In addition, heating of byproducts remaining in the reaction vessel without being removed outside the system results in the formation of polymeric compounds, and the adherence of these compounds to the reaction vessel makes continuous operation over a long period of time difficult.

Patent Document 1: U.S. Pat. No. 4,497,963;
Patent Document 2: U.S. Pat. No. 4,290,970;
Patent Document 3: U.S. Pat. No. 4,388,238;
Patent Document 4: U.S. Pat. No. 4,430,505;
Patent Document 5: U.S. Pat. No. 4,480,110;
Patent Document 6: U.S. Pat. No. 4,596,678;
Patent Document 7: U.S. Pat. No. 4,596,679;
Patent Document 8: European Patent Application Laid-open No. 0320235;
Patent document 9: U.S. Pat. No. 2,692,275;
Patent Document 10: U.S. Pat. No. 3,734,941;
Patent Document 11: U.S. Pat. No. 4,081,472;
Patent document 12: U.S. Pat. No. 4,388,426;
Patent Document 13: U.S. Pat. No. 4,482,499;
Patent document 14: U.S. Pat. No. 4,613,466;

Patent Document 15: U.S. Pat. No. 4,386,033;
Patent Document 16: U.S. Pat. No. 4,388,246;
Patent Document 17: U.S. Pat. No. 4,692,250;
Patent Document 18: European Patent Application No. 0355443;
Patent Document 19: Japanese Patent No. 3382289;
Non-Patent Document 1: Berchte der Deutechen Chemischen Gesellschaft, Vol. 3, p. 653, 1870; and
Non-Patent Document 2: Journal of American Chemical Society, Vol. 81, p. 2138, 1959.

DISCLOSURE OF INVENTION

Problems to be Solved by the Invention

As has been described above, various processes have been studied to produce isocyanates without using highly toxic phosgene. However, since these processes have problems such as the formation of high boiling point byproducts, and difficulties in continuous operation over a long period of time due to the adherence of these high boiling point byproducts to the reaction vessel, hardly any of these processes have been carried out industrially.

An object of the present invention is to provide a process for long-term, stable production of isocyanates at a high yield without the various problems found in the prior art during production of isocyanates without using phosgene.

Means for Solving the Problems

In view of the above, as a result of conducting extensive studies on the above-mentioned problems, the inventors of the present invention unexpectedly found that a carbamic acid ester or isocyanate is less susceptible to the occurrence of side reactions like those described above in the presence of a specific compound having an active proton. Moreover, it was also found that, in the case of having used this specific compound having an active proton, there is hardly any precipitation of high boiling point byproducts formed as a result of the side reactions, thereby not causing adherence to or obstruction of the reaction vessel. As a result of conducting extensive studies thereon, the inventors of the present invention determined that high boiling point substances formed by these side reactions have high solubility in the specific compound having an active proton, thereby enabling these substances to be easily removed outside the system. In addition, although there are cases in which some of specific compounds having an active proton are subjected to a reaction presumed to be the result of thermal denaturation, it was unexpectedly further found that, in the case of carrying out thermal decomposition of a carbamic acid ester in the presence of a specific carbonic acid derivative, in addition to this thermal denaturation being less likely to occur, the yield of isocyanate is improved. Although the mechanism by which isocyanate yield is improved is not clear, the inventors of the present invention presume that since the compound having the active proton reduces the likelihood of thermal denaturation as result of the coexistence of a specific carbonic acid derivative, the formation of high boiling point substances is most likely inhibited by a reaction between the compound having the active proton subjected to thermal denaturation and the carbamic acid ester and/or isocyanate.

The inventors of the present invention solved the above-mentioned problems of the prior art based on the unexpected findings described above, thereby leading to completion of the present invention.

Namely, the present invention provides the following:
[1] a process for producing an isocyanate by subjecting a carbamic acid ester to a decomposition reaction, wherein the decomposition reaction is carried out in the presence of a compound having an active proton;
[2] the process according to item [1], wherein the compound having the active proton is a compound having a hydroxyl group;
[3] the process according to item [2], wherein the compound having the hydroxyl group is an aromatic hydroxy compound;
[4] the process according to item [3], wherein the aromatic hydroxy compound is an aromatic hydroxy compound having a substituent;
[5] the process according to item [4], wherein the aromatic hydroxy compound having the substituent is a compound represented by the following formula (1):

(wherein ring A represents an aromatic hydrocarbon which has 6 to 20 carbon atoms, and which may has a substituent, the ring A being monocyclic or multicyclic,
R$^1$ represents or a hydroxyl group or a group other than a hydrogen atom, the group being an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy and the aralkyl groups containing an atom selected from carbon, oxygen and nitrogen atoms, and R$^1$ may bond with A to form a ring structure);
[6] the process according to item [5], wherein the aromatic hydroxy compound is a compound represented by the following formula (2):

(wherein ring A and R$^1$ are the same as defined above,
R$^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 atoms, the above groups containing an atom selected from carbon, oxygen and nitrogen atoms, or a hydrogen atom or a hydroxyl group, and R$^2$ may bond with A to form a ring structure);
[7] the process according to item [6], wherein in formula (2) above, a total number of carbon atoms constituting R$^1$ and R$^2$ is from 2 to 20;
[8] the process according to any one of items [5] to [7], wherein the ring A of the aromatic hydroxy compound is a structure containing at least one structure selected from the group consisting of a benzene ring, a naphthalene ring and an anthracene ring;

[9] the process according to item [1], wherein the carbamic acid ester is an aliphatic carbamic acid ester;
[10] the process according to item [9], wherein the aliphatic carbamic acid ester is an aliphatic polycarbamic acid ester;
[11] the process according to item [9], wherein the aliphatic carbamic acid ester is a compound represented by the following formula (3):

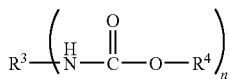
(3)

(wherein $R^3$ represents a group selected from the group consisting of an aliphatic group having 1 to 20 carbon atoms and an aromatic group having 6 to 20 carbon atoms, the aliphatic and the aromatic groups containing an atom selected from carbon and oxygen atoms, and the groups having a valence equal to n, $R^4$ represents an aliphatic group which has 1 to 20 carbon atoms, and which has an atom selected from carbon and oxygen atoms, and n represents an integer of 1 to 10);
[12] the process according to item [11], wherein the aliphatic carbamic acid ester is a compound represented by the formula (3) wherein $R^3$ represents a group selected from the group consisting of an alkyl group having 1 to 20 carbon atoms and a cycloalkyl group having 5 to 20 carbon atoms;
[13] the process according to item [1], wherein the decomposition reaction is carried out in the presence of the compound having the active proton and a carbonic acid derivative;
[14] the process according to item [13], wherein the carbonic acid derivative is a compound represented by the following formula (4):

(4)

(wherein each of X and Y independently represents an aliphatic alkoxy group having 1 to 20 carbon atoms, an aryloxy group having 6 to 20 carbon atoms, an aralkyloxy group having 7 to 20 carbon atoms or an amino group having 0 to 20 carbon atoms);
[15] the process according to item [14], wherein the carbonic acid derivative is carbonic acid ester or urea compound;
[16] the process according to item [15], wherein the carbonic acid derivative is a carbonic acid ester represented by the following formula (5):

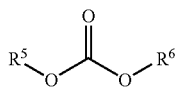
(5)

(wherein each of $R^5$ and $R^6$ independently represents an aliphatic group having 1 to 20 carbon atoms, an aryl group having 6 to 20 carbon atoms or an aralkyl group having 7 to 20 carbon atoms, the aliphatic, the aryl and aralkyl groups containing an atom selected from carbon and oxygen atoms);
[17] the process according to item [15], wherein the urea compound is urea;
[18] the process according to item [1], wherein the decomposition reaction is a thermal decomposition reaction;
[19] the process according to item [1], wherein the carbamic acid ester is supplied to a reaction vessel in which the decomposition reaction is carried out in a form of a mixture with the compound having the active proton;
[20] the process according to item [2], wherein the carbamic acid ester is supplied to a reaction vessel in which the decomposition reaction is carried out in a form of a mixture with the carbonic acid derivative;
[21] the process according to item [20], wherein the carbamic acid ester is supplied to a reaction vessel in which the decomposition reaction is carried out in a form of a mixture with the carbonic acid derivative and the compound having the active proton;
[22] the process according to any one of items [19] to [21], wherein a low boiling point component formed by the decomposition reaction is extracted from the reaction vessel in a form of a gaseous component, and all or a portion of a solution containing the carbamic acid ester and/or the compound having the active proton is extracted from a bottom of the reaction vessel.

Advantageous Effects of the Invention

According to the present invention, isocyanates can be produced efficiently without using phosgene.

BRIEF DESCRIPTION OF DRAWINGS

DESCRIPTION OF REFERENCE NUMERICALS (FIG. 1)
101, 107: distillation column, 102: column-type reaction vessel, 103, 106: thin film evaporator, 104: autoclave, 105: decarbonization tank, 111, 112, 117: reboiler, 121, 123, 126, 127: condenser, 1, 9: supply line, 2, 4, 5, 6, 7, 8, 10, 11, 12, 13, 14: transfer line, 3, 15: recovery line, 16: extraction line, 17: feed line.
(FIG. 2)
201: feed tank, 202: thin film evaporator, 203, 204: distillation column, 205, 207: condenser, 206, 208: reboiler, 21, 22, 23, 24, 25, 26, 27, 28, 29, 30, 31, 32, 33: transfer line
(FIG. 3)
401: feed tank, 402: thin film evaporator, 403, 404, 405: distillation column, 406, 408, 410: reboiler, 407, 409, 411: condenser, 41, 42, 43, 44, 45, 46, 47, 48, 49, 50, 51, 52, 53, 54, 55, 56, 57, 58: transfer line
(FIG. 4)
601, 604: stirring tank, 602, 605: tank, 603: thin film evaporator, 613: ion exchange resin column, 607, 610: distillation column, 608, 611: condenser, 609, 612: reboiler, 61, 62, 63, 64, 65, 66, 67, 68, 69, 70, 71, 72, 73, 74, 75, 76, 77, 78, 79, 80, 81: transfer line

BEST MODE FOR CARRYING OUT THE INVENTION

Figure 1:
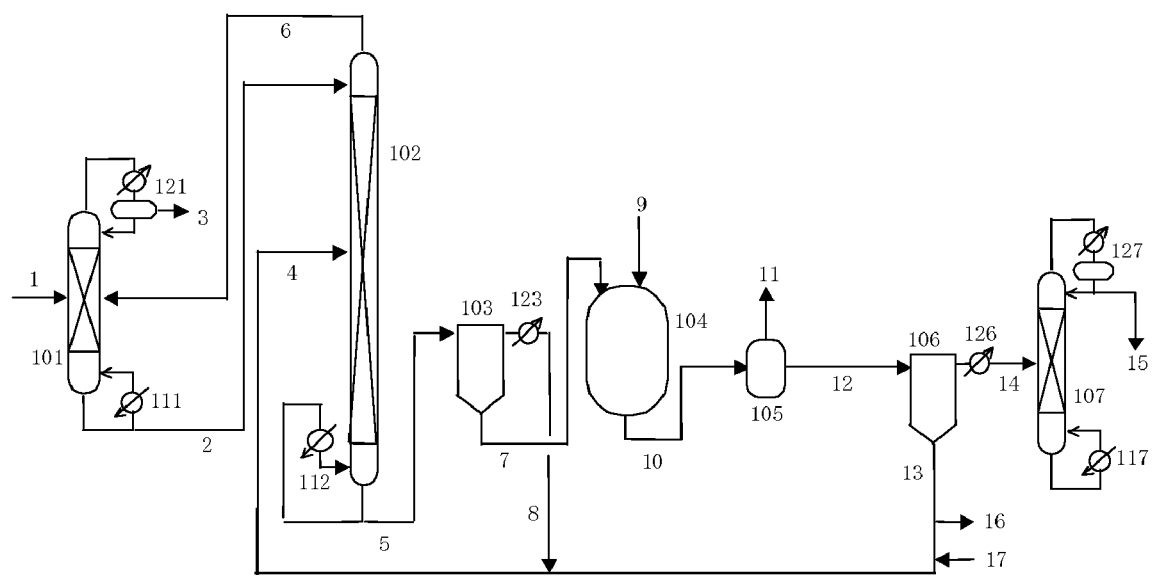
FIG. 1 shows a conceptual drawing illustrating the continuous production apparatus for producing carbonic acid ester used in an embodiment of the present invention.

The following provides a detailed explanation of the best mode for carrying out the present invention (hereinafter referred to as "the present embodiment"). Furthermore, the present invention is not limited to the following present embodiment, but rather can be modified in various ways within the scope of the gist thereof.

The process for producing an isocyanate according to the present embodiment comprises a process for producing an isocyanate by supplying a carbamic acid ester to a decomposition reaction, wherein the decomposition reaction is carried out in the presence of a compound having an active proton. Moreover, the present invention comprises carrying out the decomposition reaction in the presence of a compound having an active proton and a carbonic acid derivative.

To begin with, the explanation is given of those compounds used in the process for producing the isocyanates according to the present embodiment.

The term "active proton" in the compound having the active proton used in the present embodiment refers to a hydrogen atom as explained below.

In general, although there are many cases in which hydrogen atoms bound to carbon atoms in molecules of organic compounds are inert and lack reactivity, there are many cases in which hydrogen atoms bound to oxygen atoms, sulfur atoms or nitrogen atoms and the like are strongly reactive and easily react with various types of reagents. Such a hydrogen atom is referred to as an active proton in the present embodiment. Examples of such active protons include hydrogen atoms contained in an atomic group such as an —OH group, —SH group, —NH$_2$ group or —COOH group. In addition, hydrogen atoms bound to a carbon atom to which is bound a strong electron-attracting group such as a —COOR group, —CN group, —NO$_2$ group or —COR group (wherein R represents an aliphatic group or aromatic group) demonstrate greater reactivity than hydrogen atoms bound to an general carbon atom, and such hydrogen atoms are also included as an active proton in the present embodiment.

Note that the compound having the active proton in the present embodiment differs from the inert solvent referred to in the prior art (see, for example, U.S. Pat. No. 4,081,472). For example, according to this patent publication, although an inert solvent refers to a compound that does not react with an isocyanate formed by thermal decomposition of carbamic acid ester, as is described in the literature with regard to this (Journal of the American Chemical Society, Vol. 64, p. 2229, 1942) that urethane is formed by a reaction between an aromatic hydroxy compound and phenyl isocyanate, the compound having the active proton reacts with the isocyanates. In this manner, the use of the compound having the active proton was avoided in the prior art due to the risk of reacting with the isocyanates, and an inert solvent was used instead that does not react with the isocyanates. However, according to studies conducted by the inventors of the present invention, it was found that the isocyanates can be advantageously recovered even in the presence of the compound having the active proton. Moreover, in the case of carrying out thermal decomposition of carbamic acid ester in the presence of the compound having the active proton, it was found that the effect of improving the yield of isocyanate is demonstrated in comparison with the case carrying out the reaction in the absence of the compound having the active proton.

The compound having the active proton used in the present embodiment is a compound having an active proton as defined above. In particular, although the compound having an —OH group, —SH group, —NH$_2$ group or —COOH group is used preferably, in the case the acidity or basicity of this group is excessively high or low, there is a strong tendency for compounds having the active proton to strongly associate, which is presumed to make it difficult to demonstrate the effects of the compounds having the active proton to be described hereinafter. According to studies conducted by the inventors of the present invention, since there are cases in which the effect of improving isocyanate yield is small, the compound having the hydroxyl group is used more preferably, while an aromatic hydroxy compound is used even more preferably.

Although there are no particular limitations on the aromatic hydroxy compound used in the present embodiment provided it is a compound having a hydroxyl group directly bound to an aromatic ring, it is preferably an aromatic hydroxy compound having a substituent, and particularly an aromatic hydroxy compound having a substituent at least one ortho position relative to a hydroxyl group as represented by the following formula (10):

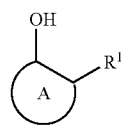

(10)

(wherein ring A represents an aromatic hydrocarbon which has 6 to 20 carbon atoms, and which may has a substituent, the ring A being monocyclic or multicyclic, $R^1$ represents or a hydroxyl group or a group other than a hydrogen atom, the group being an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy and the aralkyl groups containing an atom selected from carbon, oxygen and nitrogen atoms, and $R^1$ may bond with A to form a ring structure).

Examples of $R^1$ in formula (10) above include aliphatic alkyl groups in which the number of carbon atoms constituting the group is a number selected from integers of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers) or the like; aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers) or the like; aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers), a tributylphenyl group (including isomers) or the like; aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers), a tributylphenoxy group (including isomers) or the like; aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers), a phenylnonyl group (including isomers) or the like; and aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers), a phenylnonyloxy group (including isomers) or the like.

Examples of ring A in formula (10) above include a benzene ring, a naphthalene ring, an anthracene ring, a phenanthracene ring, a naphthacene ring, a chrycene ring, a pyrene ring, a triphenylene ring, a pentalene ring, a azulene ring, a heptalene ring, an indacene ring, a biphenylene ring, an acenaphthylene ring, an aceanthrylene ring, an acephenanthrylene ring or the like. Preferable examples include rings selected from the group consisting of a benzene ring, a naphthalene ring and an anthracene ring. In addition, these rings may have a substituent other than the above-mentioned $R^1$, examples of which include aliphatic alkyl groups in which the number of carbon atoms constituting the group is a number selected from integers of 1 to 20, such as a methyl group, an ethyl group, an propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers) or the like; aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers) or the like; aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers), a tributylphenyl group (including isomers) or the like; aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers), a tributylphenoxy group (including isomers) or the like; aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers), a phenylnonyl group (including isomers) or the like; aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers), a phenylnonyloxy group (including isomers) or the like; and hydroxyl groups.

In addition, the aromatic hydroxy compound can be used preferably whether it is an aromatic hydroxy compound having a substituent at one ortho position relative to a hydroxyl group or an aromatic hydroxy compound having substituents at two ortho positions relative to a hydroxyl group as in a compound represented by the following formula (11):

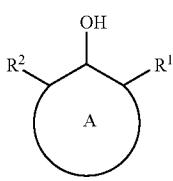

(11)

(wherein ring A and $R^1$ are the same as defined above, $R^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 atoms, the above groups containing an atom selected from carbon, oxygen and nitrogen atoms, or a hydrogen atom or a hydroxyl group, and $R^2$ may bond with A to form a ring structure).

Examples of $R^2$ in the above-mentioned formula (11) include a hydrogen atom; a hydroxyl group; aliphatic alkyl groups in which the number of carbon atoms constituting the group is a number selected from integers of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers) or the like; aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers) or the like; aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers), a tributylphenyl group (including isomers) or the like; aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers), a tributylphenoxy group (including isomers) or the like; aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers), a phenylnonyl group (including isomers) or the like; and aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers), a phenylnonyloxy group (including isomers) or the like.

In the case the aromatic hydroxy compound used in the process for producing isocyanates according to the present embodiment is an aromatic hydroxy compound having substituents at two ortho positions relative to a hydroxyl group, aromatic hydroxy compounds represented by the above-mentioned formula (11) in which the total number of carbon atoms constituting $R^1$ and $R^2$ is 2 to 20 are used preferably. There are no particular limitations on the combinations of $R^1$ and $R^2$ provided the total number of carbon atoms constituting $R^1$ and $R^2$ is 2 to 20.

Examples of such aromatic hydroxy compounds include compounds represented by the following formula (12):

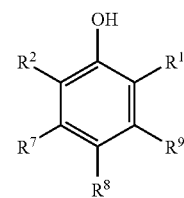

(12)

(wherein $R^1$ and $R^2$ are the same as previously defined, and
$R^7$, $R^8$ and $R^9$ respectively and independently represent a hydrogen atom, or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl and aralkyloxy groups containing an atom selected from carbon, oxygen and nitrogen atoms).

In particular, aromatic hydroxy compounds in which $R^1$ and $R^8$ in the above-mentioned formula (12) respectively and independently represent a group represented by the following formula (13) and $R^2$, $R^7$ and $R^9$ represent hydrogen atoms, or aromatic hydroxy compounds in which $R^1$ in the above-mentioned formula (12) represents a linear or branched alkyl group having 1 to 8 carbon atoms and $R^2$ and $R^8$ respectively and independently represent a hydrogen atom or a linear or branched alkyl group having 1 to 8 carbon atoms, are used preferably:

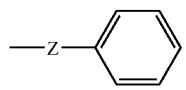
(13)

(wherein Z merely represents a bond, or a branched structure selected from the structures represented by the following formulas (14) or (15):

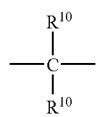
(14)

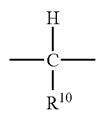
(15)

wherein $R^{10}$ represents a linear or branched alkyl group having 1 to 3 carbon atoms).

Examples of such aromatic hydroxy compounds include 2-ethylphenol, 2-propylphenol (including isomers), 2-butylphenol (including isomers), 2-pentylphenol (including isomers), 2-hexylphenol (including isomers), 2-heptylphenol (including isomers), 2-phenylphenol (including isomers), 2,6-dimethylphenol, 2,4-diethylphenol, 2,6-diethylphenol, 2,4-dipropylphenol (including isomers), 2,6-dipropylphenol (including isomers), 2,4-dibutylphenol (including isomers), 2,4-dipentylphenol (including isomers), 2,4-dihexylphenol (including isomers), 2,4-diheptylphenol (including isomers), 2-methyl-6-ethylphenol, 2-methyl-6-propylphenol (including isomers), 2-methyl-6-butylphenol (including isomers), 2-methyl-6-pentylphenol (including isomers), 2-ethyl-6-propylphenol (including isomers), 2-ethyl-6-butylphenol (including isomers), 2-ethyl-6-pentylphenol (including isomers), 2-propyl-6-butylphenol (including isomers), 2-ethyl-4-methylphenol (including isomers), 2-ethyl-4-propylphenol (including isomers), 2-ethyl-4-butylphenol (including isomers), 2-ethyl-4-pentylphenol (including isomers), 2-ethyl-4-hexylphenol (including isomers), 2-ethyl-4-heptylphenol (including isomers), 2-ethyl-4-octylphenol (including isomers), 2-ethyl-4-phenylphenol (including isomers), 2-ethyl-4-cumylphenol (including isomers), 2-propyl-4-methylphenol (including isomers), 2-propyl-4-ethylphenol (including isomers), 2-propyl-4-butylphenol (including isomers), 2-propyl-4-pentylphenol (including isomers), 2-propyl-4-hexylphenol (including isomers), 2-propyl-4-hetpylphenol (including isomers), 2-propyl-4-octylphenol (including isomers), 2-propyl-4-phenylphenol (including isomers), 2-propyl-4-cumylphenol (including isomers), 2-butyl-4-methylphenol (including isomers), 2-butyl-4-ethylphenol (including isomers), 2-butyl-4-propylphenol (including isomers), 2-butyl-4-pentylphenol (including isomers), 2-butyl-4-hexylphenol (including isomers), 2-butyl-4-heptylphenol (including isomers), 2-butyl-4-octylphenol (including isomers), 2-butyl-4-phenylphenol (including isomers), 2-butyl-4-cumylphenol (including isomers), 2-pentyl-4-methylphenol (including isomers), 2-pentyl-4-ethylphenol (including isomers), 2-pentyl-4-propylphenol (including isomers), 2-pentyl-4-butylphenol (including isomers), 2-pentyl-4-hexylphenol (including isomers), 2-pentyl-4-heptylphenol (including isomers), 2-pentyl-4-octylphenol (including isomers), 2-pentyl-4-phenylphenol (including isomers), 2-pentyl-4-cumylphenol (including isomers), 2-hexyl-4-methylphenol (including isomers), 2-hexyl-4-ethylphenol (including isomers), 2-hexyl-4-propylphenol (including isomers), 2-hexyl-4-butylphenol (including isomers), 2-hexyl-4-pentylphenol (including isomers), 2-hexyl-4-heptylphenol (including isomers), 2-hexyl-4-octylphenol (including isomers), 2-hexyl-4-phenylphenol (including isomers), 2-hexyl-4-cumylphenol (including isomers), 2-heptyl-4-methylphenol (including isomers), 2-heptyl-4-ethylphenol (including isomers), 2-heptyl-4-propylphenol (including isomers), 2-heptyl-4-butylphenol (including isomers), 2-heptyl-4-pentylphenol (including isomers), 2-heptyl-4-hexylphenol (including isomers), 2-heptyl-4-octylphenol (including isomers), 2-heptyl-4-phenylphenol (including isomers), 2-heptyl-4-cumylphenol (including isomers), 2,4,6-trimethylphenol, 2,6-dimethyl-4-ethylphenol, 2,6-dimethyl-4-propylphenol (including isomers), 2,6-dimethyl-4-butylphenol (including isomers), 2,6-dimethyl-4-pentylphenol (including isomers), 2,6-dimethyl-4-hexylphenol (including isomers), 2,6-dimethyl-4-phenylphenol (including isomers), 2,6-dimethyl-4-cumylphenol (including isomers), 2,4,6-triethylphenol, 2,6-diethyl-4-methylphenol, 2,6-diethyl-4-propylphenol (including isomers), 2,6-diethyl-4-butylphenol (including isomers), 2,6-diethyl-4-pentylphenol (including isomers), 2,6-diethyl-4-hexylphenol (including isomers), 2,6-diethyl-4-phenylphenol, 2,6-diethyl-4-cumylphenol, 2,4,6,-tripropylphenol (including isomers), 2,6-dipropyl-4-ethylphenol (including isomers), 2,6-dipropyl-4-methylphenol (including isomers), 2,6-dipropyl-4-butylphenol (including isomers), 2,6-dipropyl-4-pentylphenol (including isomers), 2,6-dipropyl-4-hexylphenol (including isomers), 2,6-dipropyl-4-phenylphenol (including isomers), 2,6-dipropyl-4-cumylphenol (including isomers), 2,4-dimethyl-6-ethylphenol, 2-methyl-4,6-diethylphenol, 2-methyl-4-propyl-6-ethylphenol (including isomers), 2-methyl-4-butyl-6-ethylphenol (including isomers), 2-methyl-4-pentyl-6-ethylphenol (including isomers), 2-methyl-4-hexyl-6-ethylphenol (including isomers), 2-methyl-4-phenyl-6-ethylphenol (including isomers), 2-methyl-4-cumyl-6-ethylphenol (including isomers), 2,4-dimethyl-6-propylphenol (including isomers), 2-methyl-4,6-dipropylphenol (including isomers), 2-methyl-4-ethyl-6-propylphenol (including isomers), 2-methyl-4-butyl-6-propylphenol (including isomers), 2-methyl-4-pentyl-6-propylphenol (including isomers), 2-methyl-4-hexyl-6-propylphenol (including isomers), 2-methyl-4-phenyl-6-propylphenol (including isomers), 2-methyl-4-cumyl-6-propylphenol (including isomers), 2,4-dimethyl-6-butylphenol (including isomers), 2-methyl-4,6-dibutylphenol (including isomers), 2-methyl-4-propyl-6-butylphenol (including isomers), 2-methyl-4-ethyl-6-butylphenol (including isomers), 2-methyl-4-pentyl-6-butylphenol (including isomers), 2-methyl-4-hexyl-6- butylphenol (including isomers), 2-methyl-4-phenyl-butylphenol (including isomers), 2-methyl-4-cumyl-6-butylphenol (including isomers), 2,4-dimethyl-6-pentylphenol, 2-methyl-4,6-dipentylphenol (including isomers), 2-methyl-4-propyl-6-pentylphenol (including isomers), 2-methyl-4-butyl-6-pentylphenol (including isomers), 2-methyl-4-ethyl-6-pentylphenol (including isomers), 2-methyl-4-hexyl-6-pentylphenol (including isomers), 2-methyl-4-phenyl-6-pentylphenol (including isomers), 2-methyl-4-cumyl-6-pentylphenol (including isomers), 2,4-dimethyl-6-hexylphenol, 2-methyl-4,6-dihexylphenol, 2-methyl-4-propyl-6-hexylphenol (including isomers), 2-methyl-4-butyl-6-hexylphenol (including isomers), 2-methyl-4-pentyl-6-hexylphenol (including isomers), 2-methyl-4-ethyl-6-hexylphenol (including isomers), 2-methyl-4-phenyl-6-hexylphenol (including isomers), 2-methyl-4-cumyl-6-hexylphenol (including isomers), 2-ethyl-4-methyl-6-propylphenol (including isomers), 2,4-diethyl-6-propylphenol (including isomers), 2-ethyl-4,6-propylphenol (including isomers), 2-ethyl-4-butyl-6-propylphenol (including isomers), 2-ethyl-4-pentyl-6-propylphenol (including isomers), 2-ethyl-4-hexyl-6-propylphenol (including isomers), 2-ethyl-4-heptyl-6-propylphenol (including isomers), 2-ethyl-4-octyl-6-propylphenol (including isomers), 2-ethyl-4-phenyl-6-propylphenol (including isomers), 2-ethyl-4-cumyl-6-propylphenol (including isomers), 2-ethyl-4-methyl-6-butylphenol (including isomers), 2,4-diethyl-6-butylphenol (including isomers), 2-ethyl-4,6-butylphenol (including isomers), 2-ethyl-4-propyl-6-butylphenol (including isomers), 2-ethyl-4-pentyl-6-butylphenol (including isomers), 2-ethyl-4-hexyl-6-butylphenol (including isomers), 2-ethyl-4-heptyl-6-butylphenol (including isomers), 2-ethyl-4-octyl-6-butylphenol (including isomers), 2-ethyl-4-phenyl-6-butylphenol (including isomers), 2-ethyl-4-cumyl-6-butylphenol (including isomers), 2-ethyl-4-methyl-6-pentylphenol (including isomers), 2,4-diethyl-6-pentylphenol (including isomers), 2-ethyl-4,6-pentylphenol (including isomers), 2-ethyl-4-butyl-6-pentylphenol (including isomers), 2-ethyl-4-propyl-6-pentylphenol (including isomers), 2-ethyl-4-hexyl-6-pentylphenol (including isomers), 2-ethyl-4-heptyl-6-pentylphenol (including isomers), 2-ethyl-4-octyl-6-pentylphenol (including isomers), 2-ethyl-4-phenyl-6-pentylphenol (including isomers), 2-ethyl-4-cumyl-6-pentylphenol (including isomers), 2-ethyl-4-methyl-6-hexylphenol (including isomers), 2,4-diethyl-6-hexylphenol (including isomers), 2-ethyl-4,6-hexylphenol (including isomers), 2-ethyl-4-propyl-6-hexylphenol (including isomers), 2-ethyl-4-pentyl-6-hexylphenol (including isomers), 2-ethyl-4-butyl-6-hexylphenol (including isomers), 2-ethyl-4-heptyl-6-hexylphenol (including isomers), 2-ethyl-4-octyl-6-hexylphenol (including isomers), 2-ethyl-4-phenyl-6-hexylphenol (including isomers), 2-ethyl-4-cumyl-6-hexylphenol (including isomers), 2-propyl-4-methyl-6-butylphenol (including isomers), 2,4-dipropyl-6-butylphenol (including isomers), 2-propyl-4,6-dibutylphenol (including isomers), 2-proypl-4-ethyl-6-butylphenol (including isomers), 2-propyl-4-pentyl-6-butylphenol (including isomers), 2-propyl-4-hexyl-6-butylphenol (including isomers), 2-propyl-4-heptyl-6-butylphenol (including isomers), 2-propyl-4-octyl-6-butylphenol (including isomers), 2-propyl-4-phenyl-6-butylphenol (including isomers), 2-propyl-4-cumyl-6-butylphenol (including isomers), 2,4-dicumylphenol and the like.

The inventors of the present invention unexpectedly found that carbamic acid esters are less susceptible to the occurrence of the above-mentioned side reactions in the presence of the hydroxy compounds as described above. Although the mechanism by which the hydroxy compound inhibits these side reactions is unclear, the inventors of the present invention presumed that, for example, in a reaction that forms a urea bond as represented by the above-mentioned formula (2), as a result of a urethane bond (—NHCOO—) of carbamic acid esters and the hydroxy compounds forming a hydrogen bond, since the urethane bonds are formed in a state in which it is difficult for them to approach each other, it is difficult for the side reaction resulting in the formation of urea bonds to occur. In particular, in the case of the aromatic hydroxy compounds having a substituent at an ortho position relative to the hydroxyl group, in addition to the effects described above, the inventors of the present invention presume that due to the effect of the substituent bound at an ortho position relative to the hydroxyl group sterically protecting the urethane bonds, the effect is demonstrated by which reactions with urethane bonds of other carbamic acid esters are strongly inhibited.

In addition, as a result of conducting extensive studies, the inventors of the present invention unexpectedly found that the aromatic hydroxy compounds having a substituent as described above has favorable solubility with respect to carbamic acid esters, carbonic acid derivatives to be described later, and high boiling point substances formed by side reactions. Namely, in the decomposition of carbamic acid esters to be described later, it is not necessary to add another solvent to obtain a homogeneous liquid phase, and even in the case a high boiling point substance is formed during decomposition of carbamic acid esters, since the aromatic hydroxy compounds used in the present embodiment dissolve this high boiling point substance, the effect is demonstrated of not allowing such substances to adhere to or obstruct the reaction vessel.

The hydroxy compound is preferable an aromatic hydroxy compound having a standard boiling point higher than the standard boiling point of a hydroxy compound corresponding to an aliphatic alkoxy group, aryloxy group or aralkyloxy group that composes the ester group of a carbamic acid ester described below. The term "standard boiling point" used in the present invention refers to the boiling point at 1 atmosphere.

<Carbamic Acid Ester>

There are no particular limitations on the carbamic acid ester used in the process for producing isocyanates according to the present embodiment, and aliphatic carbamic acid esters are used preferably. Examples of aliphatic carbamic acid esters include compounds represented by the following formula (16):

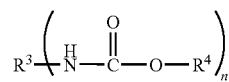

(16)

(wherein $R^3$ represents a group selected from the group consisting of an aliphatic group having 1 to 20 carbon atoms and an aromatic group having 6 to 20 carbon atoms, the aliphatic and aromatic groups containing an atom selected from carbon and oxygen atoms, and the groups having a valence equal to n, $R^4$ represents an aliphatic group which has 1 to 20 carbon atoms, and which contains an atom selected from carbon and oxygen atoms, and n represents an integer of 1 to 10).

In formula (16) above, n is preferably a number selected from integers of 2 or more, and more preferably an aliphatic polycarbamic acid ester in which n is 2.

Examples of $R^3$ in formula (16) include linear hydrocarbon groups such as methylene, dimethylene, trimethylene, tetramethylene, pentamethylene, hexamethylene, octamethylene or the like; unsubstituted acyclic hydrocarbon groups such as cyclopentane, cyclohexane, cycloheptane, cyclooctane, bis(cyclohexyl)alkane or the like; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers), hexylcyclohexane (including isomers) or the like; dialkyl-substituted cyclohexanes such as dimethylcyclohexane (including isomers), diethylcyclohexane (including isomers), dibutylcyclohexane (including isomers) or the like; trialkyl-substituted cyclohexanes such as 1,5,5-trimethylcyclohexane, 1,5,5-triethylcyclohexane, 1,5,5-tripropylcyclohexane (including isomers), 1,5,5-tributylcyclohexane (including isomers) or the like; monoalkyl-substituted benzenes such as toluene, ethylbenzene, propylbenzene; dialkyl-substituted benzenes such as xylene, diethylbenzene, dipropylbenzene; or the like and aromatic hydrocarbons such as diphenylalkane, benzene or the like. In particular, hexamethylene, phenylene, diphenylmethane, toluene, cyclohexane, xylene, methylcyclohexane, isophorone and cyclohexylmethane are used preferably.

Examples of $R^4$ in formula (16) include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers) or the like; cycloalkyl groups such as a cyclopentyl group, a cyclohexyl group, a cycloheptyl group, a cyclooctyl group, a cyclononyl group, a cyclodecyl group or the like; and, alkoxyalkyl groups such as a methoxymethyl group, a methyoxyethyl group (including isomers), a methoxypropyl group (including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group, an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group, an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group, a pentadecyloxyethyl group (including isomers), a pentadecyloxypropyl group (including isomers), a pentadecyloxybutyl group (including isomers), a pentadecyloxypentyl group (including isomers), a hexadecyloxymethyl group (including isomers), a hexadecyloxyethyl group (including isomers), a hexadecyloxypropyl group (including isomers), a hexadecyloxybutyl group (including isomers), a heptadecyloxymethyl group, a heptadecyloxyethyl group (including isomers), a heptadecyloxypropyl group (including isomers), an octadecyloxymethyl group (including isomers), an octadecyloxyethyl group (including isomers) or the like. Among these, alkyl groups in which the number of carbon atoms constituting the group is a number selected from an integer of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers) or the like, and cycloalkyl groups in which the number of carbon atoms constituting the group is a number selected from an integer of 5 to 20, such as a cyclopentyl group, a cyclohexyl group, a cycloheptyl group, a cyclooctyl group, a dicyclopentyl group (including isomers), a dicyclohexyl group (including isomers) or the like are more preferable, alkyl groups in which the number of carbon atoms constituting the alkyl group is a number selected from an integer of 4 to 6 being even more preferable.

Examples of such alkyl polycarbamates include alkyl carbamates such as N,N'-hexanediyl-bis-carbamic acid dimethyl ester, N,N'-hexanediyl-bis-carbamic acid diethyl ester, N,N'-hexanediyl-bis-carbamic acid dibutyl ester (including isomers), N,N'-hexanediyl-bis-carbamic acid dipentyl ester (including isomers), N,N'-hexanediyl-bis-carbamic acid dihexyl ester (including isomers), N,N'-hexanediyl-bis-carbamic acid dioctyl ester (including isomers), dimethyl-4,4'-methylene-dicyclohexyl carbamate, diethyl-4,4'-methylene-dicyclohexyl carbamate, dipropyl-4,4'-methylene-dicyclohexyl carbamate (including isomers), dibutyl-4,4'-methylene-dicyclohexyl carbamate (including isomers), dipentyl-4,4'-methylene-dicyclohexyl carbamate (including isomers), dihexyl-4,4'-methylene-dicyclohexyl carbamate (including isomers), diheptyl-4,4'-methylene-dicyclohexyl carbamate (including isomers), dioctyl-4,4'-methylene-dicyclohexyl carbamate (including isomers), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers), 3-(octyloxycarbonylamino-methyl)-3,5,5-trimethylcyclohexyl carbamic acid octyl ester (including isomers), toluene-dicarbamic acid dimethyl ester (including isomers), toluene-dicarbamic acid diethyl ester (including isomers), toluene-dicarbamic acid dipropyl ester (including isomers), toluene-dicarbamic acid dibutyl ester (including isomers), toluene-dicarbamic acid dipentyl ester (including isomers), toluene-dicarbamic acid dihexyl ester (including isomers), toluene-dicarbamic acid diheptyl ester (including isomers), toluene-dicarbamic acid dioctyl ester (including isomers), N,N'-(4,4'-methanediyl-diphenyl)-biscarbamic acid dimethyl ester, N,N'-(4,4'-methanediyl-diphenyl)-biscarbamic acid diethyl ester, N,N'-(4,4'-methanediyl-diphenyl)-biscarbamic acid dipropyl ester, N,N'-(4,4'-methanediyl-diphenyl)-biscarbamic acid dibutyl ester, N,N'-(4,4'-methanediyl-diphenyl)-biscarbamic acid dipentyl ester, N,N'-(4,4'-methanediyl-diphenyl)-biscarbamic acid dihexyl ester, N,N'-(4,4'-methanediyl-diphenyl)-biscarbamic acid diheptyl ester, N,N'-(4,4'-methanediyl-diphenyl)-biscarbamic acid dioctyl ester or the like.

Among these, alkyl carbamates in which $R^3$ in formula (16) above represents a group selected from the group consisting of alkyl groups having 1 to 20 carbon atoms and cycloalkyl groups having 5 to 20 carbon atoms are used preferably, alkyl carbamates represented by any one of the following formulas (17) to (19) are used particularly preferably:

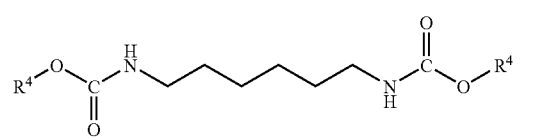

(17)

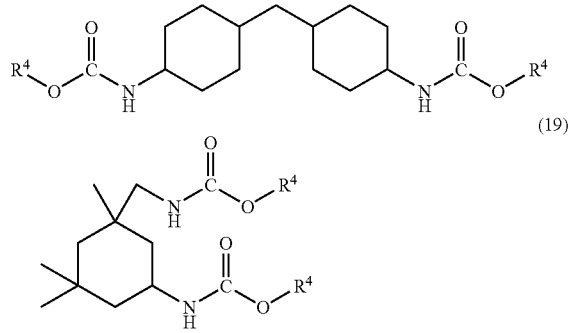

(19)

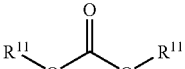

(wherein R⁴ is the same as defined above).

Examples of alkyl polycarbamates represented by formula (17) include N,N'-hexanediyl-bis-carbamic acid dimethyl ester, N,N'-hexanediyl-bis-carbamic acid diethyl ester, N,N'-hexanediyl-bis-carbamic acid dibutyl ester (including isomers), N,N'-hexanediyl-bis-carbamic acid dipentyl ester (including isomers), N,N'-hexanediyl-bis-carbamic acid dihexyl ester (including isomers) and N,N'-hexanediyl-bis-carbamic acid dioctyl ester (including isomers). In addition, examples of alkyl polycarbamates represented by formula (18) include dimethyl-4,4'-methylene-dicyclohexyl carbamate, diethyl-4,4'-methylene-dicyclohexyl carbamate, dipropyl-4,4'-methylene-dicyclohexyl carbamate (including isomers), dibutyl-4,4'-methylene-dicyclohexyl carbamate (including isomers), dipentyl-4,4'-methylene-dicyclohexyl carbamate (including isomers), dihexyl-4,4'-methylene-dicyclohexyl carbamate (including isomers), diheptyl-4,4'-methylene-dicyclohexyl carbamate (including isomers) and dioctyl-4,4'-methylene-dicyclohexyl carbamate (including isomers). Moreover, examples of alkyl polycarbamates represented by formula (19) include alkyl polycarbamates such as 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers), 3-(octyloxycarbonylamino-methyl)-3,5,5-trimethylcyclohexyl carbamic acid octyl ester (including isomers) or the like.

A known method can be used to produce these carbamic acid esters. For example, a carbamic ester may be produced by reacting amine compounds with carbon monoxide, oxygen and aliphatic alcohols or aromatic hydroxy compounds, or by reacting carbonic acid esters with an amine compounds, or by reacting amine compounds with urea and aliphatic alcohols or aromatic hydroxy compounds.

For example, examples of methods for producing carbamic acid esters by the reaction between carbonic acid esters and amine compounds is indicated below.

Carbonic acid esters represented by the following formula (20) can be used for the carbonic acid ester.

(20)

(wherein $R^{11}$ represents a linear or branched aliphatic group having 1 to 20 carbon atoms).

Examples of $R^{11}$ include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers) or the like; cycloalkyl groups such as a cyclopentyl group, a cyclohexyl group, a cycloheptyl group, a cyclooctyl group, a cyclononyl group, a cyclodecyl group or the like; and, alkoxyalkyl groups such as a methoxymethyl group, a methyoxyethyl group (including isomers), a methoxypropyl group (including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group (including isomers), an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group, an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group, a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), s pentadecyloxymethyl group (including isomers), a pentadecyloxyethyl group (including isomers), a pentadecyloxypropyl group (including isomers), a pentadecyloxybutyl group (including isomers), a pentadecyloxypentyl group (including isomers), a hexadecyloxymethyl group, a hexadecyloxyethyl group (including isomers), a hexadecyloxypropyl group (including isomers), a hexadecyloxybutyl group (including isomers), a heptadecyloxymethyl group (including isomers), a heptadecyloxyethyl group (including isomers), a heptadecyloxypropyl group (including isomers), an octadecyloxymethyl group (including isomers), an octadecyloxyethyl group (including isomers) or the like. Among these, alkyl groups in which the number of carbon atoms constituting the group is a number selected from an integer of 1 to 20 are used preferably, such as a methyl group, an ethyl group, a propyl group (including isomers), a butyl group (including isomers), a pentyl group (including isomers), a hexyl group (including isomers), a heptyl group (including isomers), an octyl group (including isomers) or the like. Examples of such carbonic acid esters include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers) or the like. Among these, dialkyl carbonates in which the number of carbon atoms constituting the alkyl group is a number selected from integers of 4 to 6 are used preferably.

The amine compounds represented by the following formula (21) are preferably used for the amine compound:

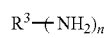

(21)

(wherein $R^3$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, and n represents an integer of 1 to 10).

In formula (21) above, a polyamine compound is used in which n is preferably 1 to 3 and more preferably n is 2.

Examples of such polyamine compounds include aliphatic diamines such as hexamethylene diamine, 4,4'-methylenebis (cyclohexylamine) (including isomers), cyclohexane diamine (including isomers), 3-aminomethyl-3,5,5-trimethylcyclohexyl amine (including isomers) or the like; and aromatic diamines such as phenylene diamine (including isomers), toluene diamine (including isomers), 4,4'-methylenedianiline or the like. Among these, aliphatic diamines such as hexamethylene diamine, 4,4'-methylenebis (cyclohexylamine) (including isomers), cyclohexane diamine (including isomers), 3-aminomethyl-3,5,5-trimethylcyclohexyl amine (including isomers) or the like are used preferably, hexamethylene diamine, 4,4'-methylenebis(cyclohexylamine) and 3-aminomethyl-3,5,5-trimethylcyclohexyl amine being used more preferably.

Reaction conditions vary according to the reacted compounds, and although the carbonic acid ester is preferably in excess based on the amino groups of the amine compound to accelerate the reaction rate and complete the reaction quickly at a stoichiometric ratio of the carbonic acid ester to amino groups of the amine compound within a range of 1.1 to 1000 times, the range is preferably from 2 to 100 times and more preferably from 2.5 to 30 times in consideration of the size of the reaction vessel. The reaction temperature is generally within the range of from normal temperature (20° C.) to 300° C., and although higher temperatures are preferable in order to accelerate the reaction rate, since undesirable reactions may conversely occur at high temperatures, the reaction temperature is preferably within the range of from 50 to 150° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or applied pressure, and the reaction is generally carried out at a pressure within the range of from 20 to $1 \times 10^6$ Pa. There are no particular limitations on the reaction time (residence time in the case of a continuous method), and is generally from 0.001 to 50 hours, preferably from 0.01 to 10 hours and more preferably from 0.1 to 5 hours. In addition, the reaction can also be completed by confirming that a desired amount of alkyl carbamate has been formed by, for example, liquid chromatography after sampling the reaction liquid. In the present embodiment, a catalyst can be used as necessary, and examples of catalysts that can be used include organic metal compounds and inorganic metal compounds of tin, lead, copper, titanium or the like, and basic catalysts such as alkylates of alkaline metals or alkaline earth metals in the form of methylates, ethylates, butyrates (including isomers) or the like of lithium, sodium, potassium, calcium or barium. Although the use of a reaction solvent is not necessarily required in the present embodiment, a suitable solvent is preferably used as a reaction solvent for the purpose of facilitating the reaction procedure, examples of which include alkanes such as hexane (including isomers), heptane (including isomers), octane (including isomers), nonane (including isomers), decane (including isomers) or the like; aromatic hydrocarbons and alkyl-substituted aromatic hydrocarbons such as benzene, toluene, xylene (including isomers), ethyl benzene, diisopropyl benzene (including isomers), dibutyl benzene (including isomers), naphthalene or the like; alcohols such as methanol, ethanol, propanol (including isomers), butanol (including isomers), pentanol (including isomers), hexanol (including isomers), heptanol (including isomers), octanol (including isomers), nonanol (including isomers) or the like; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyl toluene (including isomers) or the like; aromatic hydroxy compounds such as phenol, methyl phenol (including isomers), ethyl phenol (including isomers), butyl phenol (including isomers), pentyl phenol (including isomers), dimethyl phenol (including isomers), diethyl phenol (including isomers), dibutyl phenol (including isomers), dipentyl phenol (including isomers) or the like; aliphatic hydrocarbons such as cyclohexane, cyclopentane, cyclooctane, ethylcyclohexane or the like; alicyclic alcohols such as cyclohexanol, cyclopentanol, cyclooctanol or the like; ketones such as methyl ethyl ketone, acetophenone or the like; esters such as dibutyl phthalate, dihexyl phthalate, dioctyl phthalate, benzylbutyl phthalate or the like; ethers and thioethers such as diphenyl ether, diphenyl sulfide or the like; and sulfoxides such as dimethylsulfoxide, diphenylsulfoxide or the like. These solvents can be used alone, or two or more types of these solvents can be used as a mixture. In addition, the carbonic acid ester used in excess based on amino groups of the amine compound is also preferably used as a solvent in the reaction.

There are no particular limitations on the reaction apparatus used when carrying out the reaction, and known reaction vessels can be used. Conventionally the known reaction vessels can be suitably combined, examples of which include a stirring tank, a pressurized stirring tank, a vacuum stirring tank, a column reactor, a distillation column, a packed column, a thin film evaporator or the like. There are no particular limitations on the material of the reaction vessel, and a known material can be used. Examples of materials that can be used include glass, stainless steel, carbon steel, Hastelloy, materials comprising a base material lined with glass, and those provided with a Teflon (registered trademark) coating.

An example of a process for producing carbamic acid ester is indicated below in the case of producing carbamic acid ester by reacting urea, a hydroxy compound and an amine compound.

An alcohol represented by the following formula (22) can be used for the hydroxy compound:

$$R^{12}-OH \tag{22}$$

(wherein $R^{12}$ represents an alkyl group having 1 to 20 carbon atoms or a cycloalkyl group having 1 to 20 carbon atoms).

Examples of $R^{12}$ in formula (22) above include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers) or the like; cycloalkyl groups such as a cyclopentyl group, a cyclohexyl group, a cycloheptyl group, a cyclooctyl group, a cyclononyl group, a cyclodecyl group or the like; and, alkoxyalkyl groups such as a methoxymethyl group, a methyoxyethyl group (including isomers), a methoxypropyl group (including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group, a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group (including isomers), an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group (including isomers), an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group, a pentadecyloxyethyl group (including isomers), a pentadecyloxypropyl group (including isomers), a pentadecyloxybutyl group (including isomers), a pentadecyloxypentyl group (including isomers), a hexadecyloxymethyl group (including isomers), a hexadecyloxyethyl group (including isomers), a hexadecyloxypropyl group (including isomers), a hexadecyloxybutyl group (including isomers), a heptadecyloxymethyl group (including isomers), a heptadecyloxyethyl group (including isomers), a heptadecyloxypropyl group (including isomers), an octadecyloxymethyl group, an octadecyloxyethyl group (including isomers) or the like. Among these, alkyl groups in which the number of carbon atoms constituting the group is a number selected from an integer of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers) or the like are preferable.

A previously-described amine compound can be used for the amine compounds.

Although varying according to the reacted compounds, the reaction conditions are such that the hydroxy compounds are used within the range of from 1 to 500 times the amino groups of the amine compound when expressed as the stoichiometric ratio. Although it is preferable to use an excess of the hydroxy compounds since complex substituted urea compounds are formed easily if the amount of the hydroxy compounds is less than one times the amount of amino groups of the amine compound, in consideration of the size of the reaction vessel, the amount of the hydroxy compounds is preferably within the range of from 1 to 100 times and more preferably within the range of from 5 to 50 times. The amount of urea is within the range of from 0.5 to 3 times the amino groups of the polyamine compounds when expressed as a stoichiometric ratio. Although it is preferable to use an excess amount of urea since complex substituted urea compounds form easily if the amount used is less than 0.5 times, since complex substituted urea compounds may form easily or unreacted urea may remain even if an excess amount of urea is used, the amount of urea used is preferably within the range of from 0.8 to 2 times. The reaction temperature is preferably from 150 to 280° C. If the temperature is lower than 150° C., the reaction slows or does not occur at all due to strong bonding between the hydroxy compound and the amine compound, urea or byproduct ammonia, or the amount of complex substituted urea compounds increases, thereby making this undesirable. On the other hand, at a temperature higher than 280° C., the urea decomposes, the hydroxy compound undergoes dehydrogenation, or the product in the form of carbamic acid ester is easily decomposed or denatured, thereby making this undesirable. In this sense, the reaction temperature is more preferably within the range of from 180 to 260° C. and even more preferably within the range of from 200 to 250° C.

Since the reaction is an equilibrium reaction that shifts toward the reactants side, it is preferably to carry out the reaction while removing by byproduct ammonia outside the system, and methods for carrying out the reaction in this manner include reactive distillation, use of an inert gas, membrane separation and adsorptive separation. For example, reactive distillation refers to separating ammonia successively formed in the reaction in the form of a gas by distillation. This can be carried out while boiling a solvent or hydroxy compound to increase the ammonia distillation efficiency. In addition, examples of a method using an inert gas include separating ammonia successively formed in the reaction from the reaction system by combining with an inert gas in a gaseous state. Examples of such inert gases include nitrogen, helium, argon, carbon dioxide gas, methane, ethane and propane, and these can be used alone or as a mixture thereof, and a method that allows the inert gas to be introduced into the reaction system is preferable. Examples of adsorbents used in an adsorptive separation method include those that can be used under the temperature conditions at which the reaction is carried out, such as silica, alumina, various types of zeolite or diatomaceous earth. Methods for removing ammonia outside the system may be carried out alone or a plurality of types of methods may be combined.

A catalyst can be used in the reaction for the purpose of, for example, increasing the reaction rate. Examples of such catalysts that are used preferably include basic catalysts such as methylates, ethylates and butyrates (including isomers) or the like of lithium, sodium, potassium, calcium or barium; rare earth elements, antimony and bismuth alone or oxides, sulfides or salts of these elements; boron alone or boron compounds; metals of the copper family, zinc family, aluminum family, carbon family or titanium family of the periodic table and sulfides of these metal compounds; and carbides and nitrides of elements of the carbon family excluding carbon, titanium family, vanadium family and chromium family of the periodic table. In the case of using the catalyst, although there are no particular limitations on the amount used thereof, catalysts can be used within the range of from 0.0001 to 100 times the amount of amino groups of the amine compound in terms of the stoichiometric ratio.

Although varying according to the composition of the reaction system, reaction temperature, ammonia removal method, reaction apparatus and the like, the reaction pressure is preferably within the range of from 0.01 to 10 MPa, and in consideration of ease of carrying out industrially, preferably within the range of from 0.1 to 5 MPa. Although varying according to the composition of the reaction system, reaction temperature, ammonia removal method, reaction apparatus, reaction pressure and the like, the reaction time is generally from 0.01 to 100 hours.

In this reaction, although it not always necessary to use a reaction solvent, suitable solvent may be used for the purpose of facilitating the reaction procedure, and examples of the solvents preferably used as reaction solvents include alkanes such as pentane (including isomers), hexane (including isomers), heptane (including isomers), octane (including isomers), nonane (including isomers), decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers), naphthalene or the like; nitrile compounds such as acetonitrile, benzonitrile or the like; alcohols such as methanol, ethanol, propanol (including isomers), butanol (including isomers), pentanol (including isomers), hexanol (including isomers), heptanol (including isomers), octanol (including isomers), nonanol (including isomers) or the like; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyl toluene (including isomers) or the like; aromatic hydroxy compounds such as phenol, methyl phenol (including isomers), ethyl phenol (including isomers), butyl phenol (including isomers), pentyl phenol (including isomers), dimethyl phenol (including isomers), diethyl phenol (including isomers), dibutyl phenol (including isomers), dipentyl phenol (including isomers) or the like; aliphatic hydrocarbons such as cyclohexane, cyclopentane, cyclooctane, ethylcyclohexane or the like; alicyclic alcohols such as cyclohexanol, cyclopentanol, cyclooctanol or the like; ketones such as methyl ethyl ketone, acetophenone or the like; esters such as dibutyl phthalate, dihexyl phthalate, dioctyl phthalate, benzylbutyl phthalate or the like; ethers and thioethers such as tetrahydrofuran, 1,4-dioxane, 1,2-dimethoxyethane, diphenyl ether, diphenyl sulfide or the like; ketone compounds such as acetone, methyl ethyl ketone or the like; ester compounds such as ethyl acetate, ethyl benzoate or the like; and sulfoxides such as dimethylsulfoxide, diphenylsulfoxide or the like. Moreover, additional examples of reaction solvents include halogenated aromatic hydrocarbon compounds such as chlorobenzene, dichlorobenzene, trichlorobenzene, fluorobenzene, chlorotoluene, chloronaphthalene, bromonaphthalene or the like, and halogenated aliphatic hydrocarbon compounds or halogenated alicyclic hydrocarbon compounds such as chlorohexane, chlorocyclohexane, trichlorofluoroethane, methylene chloride, carbon tetrachloride or the like.

There are no particular limitations on the reaction apparatus used when carrying out the reaction, and known reaction vessels can be used. Conventionally the known reaction vessels can be suitably combined, examples of which include a stirring tank, a pressurized stirring tank, a vacuum stirring tank, a column reactor, a distillation column, a packed column, a thin film evaporator or the like. There are no particular limitations on the material of the reaction vessel, and a known material can be used. Examples of materials that can be used include glass, stainless steel, carbon steel, Hastelloy, materials comprising a base material lined with glass, and those provided with a Teflon (registered trademark) coating.

A carbamic acid ester produced in a method exemplified above may be subjected to a decomposition reaction as is, or may be subjected to a decomposition reaction after having purified the carbamic acid ester. Examples of methods for purifying the carbamic acid ester from the reaction liquid include known methods such as methods for distilling off low boiling point components such as hydroxy compounds, urea compounds and carbonic acid esters by distillation, methods involving washing with a solvent, and purification by crystallization. In addition, in the case of using the catalyst in the production of carbamic acid ester, the catalyst can also be used as the catalyst of a thermal decomposition reaction depending on the case, or the catalyst for use in a thermal decomposition reaction may be added while still present, or the catalyst may not be used in the thermal decomposition reaction. In addition, the catalyst used in the production of carbamic acid ester may also be removed. In the case of using a basic catalyst, since there are cases in which a reaction attributable to the catalyst occurs during the thermal decomposition reaction resulting in a decrease in yield, the thermal decomposition reaction is carried out after removing the catalyst in such cases. A known method can be used to remove the catalyst. A preferable example of such a method involves neutralizing the catalyst by treating with an organic acid or an inorganic acid in a homogeneous or heterogeneous phase. An acid used for this purpose is preferably a mono- or dicarboxylic acid, ion exchange resin type of alkyl- or arylsulfonic acid, or phosphoric acid. Although removal of the catalyst may be carried out within the range of normal temperature to 200° C., since there are cases in which the formed carbamic acid is solidified or denatured, it is preferable to continue to carry out the reaction while maintaining the temperature at which the formed carbamic acid ester does not precipitate from the reaction liquid of the carbamic acid ester production step after having carried out the carbamic acid ester production step.

Next, the carbamic acid ester is subjected to (thermal) decomposition step after having removed raw materials used in excess.

<Carbonic Acid Derivative>

A carbonic acid derivative in the present embodiment refers to a compound having a carbonyl group. In the present embodiment, the carbonic acid derivative represented by the following formula (23) is used particularly preferably:

(23)

(wherein each of X and Y independently represents an aliphatic alkoxy group having 1 to 20 carbon atoms, an aryloxy group having 6 to 20 carbon atoms, an aralkyloxy group having 7 to 20 carbon atoms or an amino group having 0 to 20 carbon atoms).

Examples of compounds represented by formula (23) above include carbonic acid esters, carbamic acid esters and urea compounds.

A carbonic acid ester refers to a compound in which one or two of the two hydrogen atoms of the carbonic acid $CO(OH)_2$ is substituted with an alkyl group or aryl group, and in the present embodiment, a compound represented by the following formula (24) is used preferably:

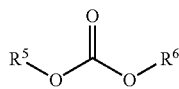

(24)

(wherein each of $R^5$ and $R^6$ independently represents an aliphatic group having 1 to 20 carbon atoms, an aryl group having 6 to 20 carbon atoms or an aralkyl group having 7 to 20 carbon atoms, the aliphatic, the aryl and aralkyl groups containing an atom selected from carbon and oxygen atoms).

Examples of $R^5$ and $R^6$ in formula (24) above include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers) or the like; cycloalkyl groups such as a cyclopentyl group, a cyclohexyl group, a cycloheptyl group, a cyclooctyl group, a cyclononyl group, a cyclodecyl group or the like; alkoxyalkyl groups such as a methoxymethyl group, a methyoxyethyl group (including isomers), a methoxypropyl group (including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group (including isomers), a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group (including isomers), an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group (including isomers), an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group, a pentadecyloxyethyl group (including isomers), a pentadecyloxypropyl group (including isomers), a pentadecyloxybutyl group (including isomers), a pentadecyloxypentyl group (including isomers), a hexadecyloxymethyl group (including isomers), a hexadecyloxyethyl group (including isomers), a hexadecyloxypropyl group (including isomers), a hexadecyloxybutyl group (including isomers), a heptadecyloxymethyl group (including isomers), a heptadecyloxyethyl group (including isomers), a heptadecyloxypropyl group (including isomers), an octadecyloxymethyl group (including isomers), an octadecyloxyethyl group (including isomers) or the like; aryl groups such as a phenyl group, a naphthyl group, an anthryl group, a pyrenyl group, phenanthryl group or the like; and aryl groups such as a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), an undecylphenyl group (including isomers), a dodecylphenyl group (including isomers), a tridecylphenyl group (including isomers), a tetradecylphenyl group (including isomers), a dimethylphenyl group (including isomers), a methylethylphenyl group (including isomers), a methylpropylphenyl group (including isomers), a methylbutylphenyl group (including isomers), a methylpentylphenyl group (including isomers), a methylhexylphenyl group (including isomers), a methylheptylphenyl group (including isomers), a methyloctylphenyl group (including isomers), a methylnonylphenyl group (including isomers), a methyldecylphenyl group (including isomers), a methylundecylphenyl group (including isomers), a methyldodecylphenyl group (including isomers), a methyltridecylphenyl group (including isomers), a diethylphenyl group (including isomers), an ethylpropylphenyl group (including isomers), an ethylbutylphenyl group (including isomers), an ethylpentylphenyl group (including isomers), an ethylhexylphenyl group (including isomers), an ethylheptylphenyl group (including isomers), an ethyloctylphenyl group (including isomers), an ethylnonylphenyl group (including isomers), an ethyldecylphenyl group (including isomers), an ethylundecylphenyl group (including isomers), an ethyldodecylphenyl group (including isomers), a dipropylphenyl group (including isomers), a propylbutylphenyl group (including isomers), a propylpentylphenyl group (including isomers), a propylhexylphenyl group (including isomers), a propylheptylphenyl group (including isomers), a propyloctylphenyl group (including isomers), a propylnonylphenyl group (including isomers), a propyldecylphenyl group (including isomers), a propylundecylphenyl group (including isomers), a dibutylphenyl group (including isomers), a butylpentylphenyl group (including isomers), a butylhexylphenyl group (including isomers), a butylheptylphenyl group (including isomers), a butyloctylphenyl group (including isomers), a butylnonylphenyl group (including isomers), a butyldecylphenyl group (including isomers), a dipentylphenyl group (including isomers), a pentylhexylphenyl group (including isomers), a pentylheptylphenyl group (including isomers), a pentyloctylphenyl group (including isomers), a pentylnonylphenyl group (including isomers), a dihexylphenyl group (including isomers), a hexylheptylphenyl group (including isomers), a hexyloctylphenyl group (including isomers), a diheptylphenyl group (including isomers), a trimethylphenyl group (including isomers), a dimethylethylphenyl group (including isomers), a dimethylpropylphenyl group (including isomers), a dimethylbutylphenyl group (including isomers), a dimethylpentylphenyl group (including isomers), a dimethylhexylphenyl group (including isomers), a dimethylheptylphenyl group (including isomers), a dimethyloctylphenyl group (including isomers), a dimethylnonylphenyl group (including isomers), a dimethyldecylphenyl group (including isomers), a dimethylundecylphenyl group (including isomers), a dimethyldodecylphenyl group (including isomers), a triethylphenyl group (including isomers), a diethylmethylphenyl group (including isomers), a diethylpropylphenyl group (including isomers), a diethylbutylphenyl group (including isomers), a diethylpentylphenyl group (including isomers), a diethylhexylphenyl group (including isomers), a diethylheptylphenyl group (including isomers), a diethyloctylphenyl group (including isomers), a diethylnonylphenyl group (including isomers), a diethyldecylphenyl group (including isomers), a tripropylphenyl group (including isomers), a dipropylmethylphenyl group (including isomers), a dipropylethylphenyl group (including isomers), a dipropylbutylphenyl group (including isomers), a dipropylpentylphenyl group (including isomers), a dipropylhexylphenyl group (including isomers), a dipropylheptylphenyl group (including isomers), a dipropyloctylphenyl group (including isomers), a tributylphenyl group (including isomers), a dibutylmethylphenyl group (including isomers), a dibutylethylphenyl group (including isomers), a dibutylpropylphenyl group (including isomers), a dibutylpentylphenyl group (including isomers), a dibutylhexylphenyl group (including isomers) or the like.

Among these, alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers); cycloalkyl groups such as a cyclopentyl group, a cyclohexyl group, a cycloheptyl group, a cyclooctyl group, a cyclononyl group, a cyclodecyl group or the like; and alkoxyalkyl groups such as a methoxymethyl group, a methyoxyethyl group (including isomers), a methoxypropyl group (including isomers), a methoxybutyl group (including isomers), a methoxypentyl group (including isomers), a methoxyhexyl group (including isomers), a methoxyheptyl group (including isomers), a methoxyoctyl group (including isomers), a methoxynonyl group (including isomers), a methoxydecyl group (including isomers), a methoxyundecyl group (including isomers), a methoxydodecyl group (including isomers), a methoxytridecyl group (including isomers), a methoxytetradecyl group (including isomers), a methoxypentadecyl group (including isomers), a methoxyhexadecyl group (including isomers), a methoxyheptadecyl group (including isomers), a methoxyoctadecyl group (including isomers), a methoxynonadecyl group (including isomers), an ethoxymethyl group, an ethoxyethyl group (including isomers), an ethoxypropyl group (including isomers), an ethoxybutyl group (including isomers), an ethoxypentyl group (including isomers), an ethoxyhexyl group (including isomers), an ethoxyheptyl group (including isomers), an ethoxyoctyl group (including isomers), an ethoxynonyl group (including isomers), an ethoxydecyl group (including isomers), an ethoxyundecyl group (including isomers), an ethoxydodecyl group (including isomers), an ethoxytridecyl group (including isomers), an ethoxytetradecyl group (including isomers), an ethoxypentadecyl group (including isomers), an ethoxyhexadecyl group (including isomers), an ethoxyheptadecyl group (including isomers), an ethoxyoctadecyl group (including isomers), a propyloxymethyl group (including isomers), a propyloxyethyl group (including isomers), a propyloxypropyl group (including isomers), a propyloxybutyl group (including isomers), a propyloxypentyl group (including isomers), a propyloxyhexyl group (including isomers), a propyloxyheptyl group (including isomers), a propyloxyoctyl group (including isomers), a propyloxynonyl group (including isomers), a propyloxydecyl group (including isomers), a propyloxyundecyl group (including isomers), a propyloxydodecyl group (including isomers), a propyloxytridecyl group (including isomers), a propyloxytetradecyl group (including isomers), a propyloxypentadecyl group (including isomers), a propyloxyhexadecyl group (including isomers), a propyloxyheptadecyl group (including isomers), a butyloxymethyl group (including isomers), a butyloxyethyl group (including isomers), a butyloxypropyl group (including isomers), a butyloxybutyl group (including isomers), a butyloxypentyl group (including isomers), a butyloxyhexyl group (including isomers), a butyloxyheptyl group (including isomers), a butyloxyoctyl group (including isomers), a butyloxynonyl group (including isomers), a butyloxydecyl group (including isomers), a butyloxyundecyl group (including isomers), a butyloxydodecyl group (including isomers), a butyloxytridecyl group (including isomers), a butyloxytetradecyl group (including isomers), a butyloxypentadecyl group (including isomers), a butyloxyhexadecyl group (including isomers), a pentyloxymethyl group (including isomers), a pentyloxyethyl group (including isomers), a pentyloxypropyl group (including isomers), a pentyloxybutyl group (including isomers), a pentyloxypentyl group (including isomers), a pentyloxyhexyl group (including isomers), a pentyloxyheptyl group (including isomers), a pentyloxyoctyl group (including isomers), a pentyloxynonyl group (including isomers), a pentyloxydecyl group (including isomers), a pentyloxyundecyl group (including isomers), a pentyloxydodecyl group (including isomers), a pentyloxytridecyl group (including isomers), a pentyloxytetradecyl group (including isomers), a pentyloxypentadecyl group (including isomers), a hexyloxymethyl group (including isomers), a hexyloxyethyl group (including isomers), a hexyloxypropyl group (including isomers), a hexyloxybutyl group (including isomers), a hexyloxypentyl group (including isomers), a hexyloxyhexyl group (including isomers), a hexyloxyheptyl group (including isomers), a hexyloxyoctyl group (including isomers), a hexyloxynonyl group (including isomers), a hexyloxydecyl group (including isomers), a hexyloxyundecyl group (including isomers), a hexyloxydodecyl group (including isomers), a hexyloxytridecyl group (including isomers), a hexyloxytetradecyl group (including isomers), a heptyloxymethyl group, a heptyloxyethyl group (including isomers), a heptyloxypropyl group (including isomers), a heptyloxybutyl group (including isomers), a heptyloxypentyl group (including isomers), a heptyloxyhexyl group (including isomers), a heptyloxyheptyl group (including isomers), a heptyloxyoctyl group (including isomers), a heptyloxynonyl group (including isomers), a heptyloxydecyl group (including isomers), a heptyloxyundecyl group (including isomers), a heptyloxydodecyl group (including isomers), a heptyloxytridecyl group (including isomers), an octyloxymethyl group (including isomers), an octyloxyethyl group (including isomers), an octyloxypropyl group (including isomers), an octyloxybutyl group (including isomers), an octyloxypentyl group (including isomers), an octyloxyhexyl group (including isomers), an octyloxyheptyl group (including isomers), an octyloxyoctyl group (including isomers), an octyloxynonyl group (including isomers), an octyloxydecyl group (including isomers), an octyloxyundecyl group (including isomers), an octyloxydodecyl group (including isomers), a nonyloxymethyl group (including isomers), a nonyloxyethyl group (including isomers), a nonyloxypropyl group (including isomers), a nonyloxybutyl group (including isomers), a nonyloxypentyl group (including isomers), a nonyloxyhexyl group (including isomers), a nonyloxyheptyl group (including isomers), a nonyloxyoctyl group (including isomers), a nonyloxynonyl group (including isomers), a nonyloxydecyl group (including isomers), a nonyloxyundecyl group (including isomers), a decyloxymethyl group (including isomers), a decyloxyethyl group (including isomers), a decyloxypropyl group (including isomers), a decyloxybutyl group (including isomers), a decyloxypentyl group (including isomers), a decyloxyhexyl group (including isomers), a decyloxyheptyl group (including isomers), a decyloxyoctyl group (including isomers), a decyloxynonyl group (including isomers), a decyloxydecyl group (including isomers), an undecyloxymethyl group (including isomers), an undecyloxyethyl group (including isomers), an undecyloxypropyl group (including isomers), an undecyloxybutyl group (including isomers), an undecyloxypentyl group (including isomers), an undecyloxyhexyl group (including isomers), an undecyloxyheptyl group (including isomers), an undecyloxyoctyl group (including isomers), an undecyloxynonyl group (including isomers), a dodecyloxymethyl group (including isomers), a dodecyloxyethyl group (including isomers), a dodecyloxypropyl group (including isomers), a dodecyloxybutyl group (including isomers), a dodecyloxypentyl group (including isomers), a dodecyloxyhexyl group (including isomers), a dodecyloxyheptyl group (including isomers), a dodecyloxyoctyl group (including isomers), a tridecyloxymethyl group (including isomers), a tridecyloxyethyl group (including isomers), a tridecyloxypropyl group (including isomers), a tridecyloxybutyl group (including isomers), a tridecyloxypentyl group (including isomers), a tridecyloxyhexyl group (including isomers), a tridecyloxyheptyl group (including isomers), a tetradecyloxymethyl group (including isomers), a tetradecyloxyethyl group (including isomers), a tetradecyloxypropyl group (including isomers), a tetradecyloxybutyl group (including isomers), a tetradecyloxypentyl group (including isomers), a tetradecyloxyhexyl group (including isomers), a pentadecyloxymethyl group (including isomers), a pentadecyloxyethyl group (including isomers), a pentadecyloxypropyl group (including isomers), a pentadecyloxybutyl group (including isomers), a pentadecyloxypentyl group (including isomers), a hexadecyloxymethyl group, a hexadecyloxyethyl group (including isomers), a hexadecyloxypropyl group (including isomers), a hexadecyloxybutyl group (including isomers), a heptadecyloxymethyl group, a heptadecyloxyethyl group (including isomers), a heptadecyloxypropyl group (including isomers), an octadecyloxymethyl group (including isomers), an octadecyloxyethyl group (including isomers) or the like are used preferably. Alkyl groups in the form of aliphatic hydrocarbon groups in which the number of carbon atoms constituting the group is a number selected from integers of 1 to 8, such as a methyl group, an ethyl group, a propyl group (including isomers), a butyl group (including isomers), a pentyl group (including isomers), a hexyl group (including isomers), a heptyl group (including isomers), an octyl group (including isomers) or the like, are used more preferably. Examples of such dialkyl carbonates include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers) or the like. Dialkyl carbonates in which the number of carbon atoms constituting the alkyl group is a number selected from integers of 4 to 6 are used more preferably.

A urea compound in the present embodiment is a compound having at least one urea bond in a molecule thereof, and preferably is a compound having a single urea bond as represented by formula (25) below:

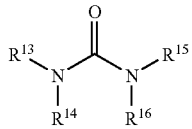

(25)

(wherein each of $R^{13}$, $R^{14}$, $R^{15}$ and $R^{16}$ independently represents an alkyl group having 1 to 20 carbon atoms or a hydrogen atom, the total number of carbon atoms constituting $R^{13}$ and $R^{14}$ is an integer of 0 to 20, and the total number of carbon atoms constituting $R^{15}$ and $R^{16}$ is an integer of 0 to 20).

Examples of $R^{13}$, $R^{14}$, $R^{15}$ and $R^{16}$ include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), a pentadecyl group (including isomers), a hexadecyl group (including isomers), a heptadecyl group (including isomers), an octadecyl group (including isomers), a nonadecyl group (including isomers), an eicosyl group (including isomers) or the like. In particular, urea, in which $R^{13}$, $R^{14}$, $R^{15}$ and $R^{16}$ in formula (25) above represent hydrogen atoms, is used preferably.

In the present embodiment, some compounds having an active proton may be susceptible to a reaction presumed to occur due to thermal denaturation depending on the conditions of the thermal decomposition reaction during thermal decomposition of carbamic acid ester in the presence of the compound having an active proton depending on the compound having the active proton. The inventors of the present invention unexpectedly found that, in the case of carrying out thermal decomposition of carbamic acid ester in the presence of the carbonic acid derivatives described above, not only is this thermal denaturation less likely to occur, but also that the yield of isocyanate is improved. Although mechanism by which isocyanate yield is improved is unclear, the inventors of the present invention presumed that since the compound having the active proton is less susceptible to thermal denaturation due to the presence of specific carbonic acid derivatives, the formation of high boiling point substances caused by a reaction between a heat-denatured compound having an active proton and carbamic acid ester and/or isocyanate is inhibited.

<Carbamic Acid Ester Decomposition Reaction>

The following provides an explanation of the carbamic acid ester decomposition reaction in the present embodiment.

The decomposition reaction in the present embodiment is a thermal decomposition reaction in which a corresponding isocyanate and a hydroxy compound (alcohol or aromatic hydroxy compound originating from the carbamic acid ester) are formed from a carbamic acid ester.

This thermal decomposition reaction is carried out in the presence of the compound having the active proton, or in the presence of the compound having the active proton and the carbonic acid derivative, as described above.

Although varying according to the compounds used, the reaction conditions are such that the amount of the compound having the active proton used is preferably from 1 to 100 times the carbamic acid ester in terms of the stoichiometric ratio. Although the amount of compound having the active proton used is preferably large from the viewpoint of inhibiting side reactions as described above, in consideration of the size of the reaction vessel and the like, the amount used is more preferably from 2 to 80 times and even more preferably from 2 to 50 times. In addition, the amount of the carbonic acid derivative used is preferably from 0.00001 to 0.1 times the compound having the active proton in terms of the stoichiometric ratio. Although some specific compounds having the active proton are susceptible to the occurrence of a reaction presumed to be caused by thermal denaturation during the thermal decomposition reaction, in the case of carrying out thermal decomposition of the carbamic acid ester in the presence of the carbonic acid derivative as previously described, the carbonic acid derivative has the effect of making it difficult for this thermal denaturation to occur. On the other hand, in the case of using a large amount of the carbonic acid derivative, there are cases in which the carbonic acid derivative reacts with the specific compound having the active proton, resulting in the formation of ether or ammonia. Thus, the amount of the carbonic acid derivative used is more preferably from 0.00005 to 0.05 times and even more preferably from 0.0001 to 0.01 times. In the case the carbonic acid derivative is contained in the carbamic acid ester during production of carbamic acid ester according to the method exemplified above, the carbonic acid derivative may be used as is, or carbonic acid derivative may be newly added to the carbamic acid ester. A specific compound having the active proton susceptible to thermal denaturation as described above refers to a compound such as an aromatic hydroxy compound substituted with a branched alkyl group. Since there are cases in which a dealkenylation reaction occurs, the formation of alkene is less likely to occur in such cases if the carbonic acid derivative is present. Although the reason for this is unclear, this dealkenylation reaction is presumed to originate from the catalyst within the system or metal ions eluted in trace amounts from the structural material of the reaction vessel, and it is presumed that the carbonic acid derivative traps these components.

Although the dealkenylation reaction as described above is not observed in the case of, for example, the aromatic hydroxy compound substituted with a group other than a branched alkyl group, since there are cases in which the yield of isocyanate formed during thermal decomposition of carbamic acid ester in the presence of the aromatic hydroxy compound decreases, it is presumed that the aromatic hydroxy compound is also subjected to some form of thermal denaturation resulting in the formation of thermal denaturation products. Side reactions between these thermal denaturation products and carbamic acid ester and/or isocyanate are then presumed to occur. In such cases as well, since the presence of the carbonic acid derivative is observed to result in an improvement of isocyanate yield, similar to the case of the aromatic hydroxy compound substituted with the branched alkyl group, the carbonic acid derivative is presumed to have the effect of reducing the likelihood of the occurrence of thermal denaturation of the aromatic hydroxy compound even in the case of aromatic hydroxy compounds substituted with the group other than the branched alkyl group.

The carbonic acid derivative need not be used in the case of using a specific compound having an active proton not subjected to thermal denaturation.

The reaction temperature is generally within the range of from 100 to 400° C., and although higher temperatures are preferable for accelerating the reaction rate, since side reactions as described above may be caused by carbamic acid ester and/or the product in the form of isocyanate at high temperatures, the reaction temperature is preferably within the range of from 130 to 300° C. and more preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or applied pressure, and the reaction is generally carried out at a pressure within the range of from 20 to $1 \times 10^6$ Pa. There are no particular limitations on the reaction time (residence time in the case of a continuous method), and is generally from 0.001 to 100 hours, preferably from 0.01 to 50 hours and more preferably from 0.1 to 30 hours. A catalyst can be used in the present embodiment, and the catalyst is used at from 0.01 to 30% by weight and preferably from 0.5 to 20% by weight, based on the weight of carbamic acid ester. For example, organic metal catalysts such as dibutyl tin dilaurate, ferrous octoate or stannous octoate, or amines such as 1,4-diazabicyclo[2,2,2]octane, triethylenediamine or triethylamine are suitable for use, the organic metal catalysts such as dibutyl tin dilaurate, ferrous octoate or stannous octoate being particularly preferable. These compounds may be used alone, or two or more types of these compounds may be used as a mixture.

A solvent can also be used in the present embodiment, and examples of solvents that can be used include alkanes such as pentane (including isomers), hexane (including isomers), heptane (including isomers), octane (including isomers), nonane (including isomers), decane (including isomers) or the like; aromatic hydrocarbons and alkyl-substituted aromatic hydrocarbons such as benzene, toluene, xylene (including isomers), ethyl benzene, diisopropyl benzene (including isomers), dibutyl benzene (including isomers), naphthalene or the like; nitrile compounds such as acetonitrile, benzonitrile or the like; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyl toluene (including isomers) or the like; aliphatic hydrocarbons such as cyclohexane, cyclopentane, cyclooctane, ethylcyclohexane or the like; alicyclic alcohols such as cyclohexanol, cyclopentanol, cyclooctanol or the like; ketones such as methyl ethyl ketone, acetophenone or the like; esters such as dibutyl phthalate, dihexyl phthalate, dioctyl phthalate, benzylbutyl phthalate or the like; ethers and thioethers such as tetrahydrofuran, 1,4-dioxane, 1,2-dimethoxyethane, diphenyl ether, diphenylsulfide or the like; ketone compounds such as acetone, methyl ethyl ketone or the like; ester compounds such as ethyl acetate, ethyl benzoate or the like; and sulfoxides such as dimethylsulfoxide, diphenylsulfoxide or the like. However, since the procedures become complex during separation and recovery of the hydroxy compound, the thermal decomposition reaction of carbamic acid ester is preferably carried out without using a solvent.

Although the thermal decomposition reaction of the present embodiment is a reaction by which the corresponding isocyanate and the hydroxy compound are formed from the carbamic acid ester as previously described, this thermal decomposition reaction is an equilibrium reaction. Thus, in order to efficiently obtain isocyanate in this thermal decomposition reaction, it is preferable to remove at least one of the products of the thermal decomposition reaction in the form of the isocyanate or the hydroxy compound from the thermal decomposition reaction system in the form of a gaseous component using a method such as distillation. Which of the isocyanate or hydroxy compound is removed can be arbitrarily determined according to the compounds used. For example, a comparison may be made of the standard boiling points of the isocyanate and the hydroxy compound, and the compound having the lower standard boiling point may be removed as a gaseous component.

The thermal decomposition reaction is preferably carried out by a continuous method. The continuous method refers to a method in which the carbamic acid ester is continuously supplied to a reaction vessel where it is subjected to the thermal decomposition reaction, at least one of the isocyanate or hydroxy compound formed is removed from the reaction vessel in the form of a gaseous component, and a portion or all of a solution containing the carbamic acid ester and/or compound having the active proton is removed from the bottom of the reaction vessel.

In the case thermal decomposition reaction is carried out on the carbamic acid ester using the continuous method, the carbamic acid ester is preferably is supplied to the reaction vessel where the thermal decomposition reaction is carried out in the form of a mixture with the carbonic acid derivative. The carbamic acid ester is more preferably supplied to the reaction vessel where the thermal decomposition reaction is carried out in the form of a mixture with the carbonic acid derivative and the compound having the active proton. There are many cases in which the carbamic acid ester is a solid at normal temperatures (for example, 25° C.). In general, the reactants are preferably liquids in the case of continuously supplying the reactants to the reaction vessel. The carbamic acid ester is preferably a liquid when continuously supplying the carbamic acid ester to the reaction vessel in this thermal decomposition reaction as well. Thus, there are many cases in which the carbamic acid ester is supplied to the reaction vessel in a state of being held to a temperature equal to or higher than the melting point of the carbamic acid ester (for example, 150° C.). However, if the carbamic acid ester is held under such temperature conditions for a long period of time, this may lead to the occurrence of side reactions as previously described, resulting in a decrease in the final yield of isocyanate.

The inventors of the present invention unexpectedly found that when the carbamic acid ester is in the form of a mixture with the compound having the active proton, or more preferably, a mixture with the carbonic acid derivative and the compound having the active proton, there is less likelihood of the above-mentioned side reactions occurring even in the case of being held under temperature conditions as described above for a long period of time. Although the mechanism by which these compounds having the active proton inhibit side reactions is unclear, the inventors of the present invention presumed that, for example, in a reaction that forms a urea bond as represented by the above-mentioned formula (2), as a result of a urethane bond (—NHCOO—) of the carbamic acid ester and the hydroxy compound forming the hydrogen bond, since the urethane bonds are formed in a state in which it is difficult for them to approach each other, it is difficult for the reaction resulting in the formation of urea bonds to occur.

In addition, since compounds having the active proton used in the present embodiment have good solubility with respect to carbamic acid esters, carbamic acid ester can be supplied to the reaction vessel where the thermal decomposition reaction is carried out in the form of a homogeneous solution of the carbamic acid ester and the compound having the active proton, thereby resulting in a simpler procedure.

In the case the carbamic acid ester is supplied to the reaction vessel where the thermal decomposition reaction is carried out in the form of a mixture with the carbonic acid derivative and the compound having the active proton, the entire amount of the compound having the active proton used may be supplied to the reaction vessel in the form of a mixture of the carbamic acid ester, the carbonic acid derivative and the compound having the active proton, or a portion of the compound having the active proton used may be added to the reaction vessel in advance, followed by adding the remainder to the reaction vessel in the form of said mixture.

Although any known material may be used for the reaction vessel and lines used to carry out the thermal decomposition reaction provided it does not have a detrimental effect on the carbamic acid ester or products in the form of the hydroxy compound and isocyanate, SUS304, SUS316, SUS316L or the like can be used preferably since they are inexpensive. There are no particular limitations on the type of reaction vessel, and a known tank reactor or a column reactor can be used. A reaction vessel is preferably used that is provided with lines for removing a low boiling point mixture containing at least one of the isocyanate and the hydroxy compound formed in the thermal decomposition reaction from the reaction vessel in the form of a gaseous component, and for removing all or a portion of a mixed liquid containing unreacted carbamic acid ester and compounds not removed in the form of gaseous components from the bottom of the reaction vessel in the form of a liquid. Various known methods are used for such a reaction vessel, examples of which include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using the thin film evaporator or the columnar reactor are preferable from the viewpoint of rapidly removing low boiling point components from the reaction system, a structure having a large gas-liquid contact area being preferable for being able to rapidly transfer the low boiling point components formed to the gaseous phase.

The reaction vessel is preferably provided with a line for supplying carbamic acid ester, a line for removing a gaseous component containing at least one of the isocyanate and the hydroxy compound formed by the thermal decomposition reaction, and a line for removing mixed liquid containing compounds not removed in the form of gaseous components, unreacted carbamic acid ester and the compound having an active proton, and a line for removing gaseous components containing at least one of the isocyanate and the hydroxy compound is preferably at a location that allows gaseous components in the reaction vessel to be removed, and the line for removing a mixed liquid containing compounds not removed in the form of gaseous components, unreacted carbamic acid ester and the compound having the active proton is particularly preferably located there below.

In addition, a line for supplying inert gas and/or liquid inert solvent from the lower portion of the reaction vessel may be separately attached, or a line may be attached for recirculating all or a portion of the mixed liquid containing unreacted carbamic acid ester and/or the compound having the active proton to the reaction vessel. Warming, cooling or heating equipment may be added to each line in consideration of clogging and the like.

The isocyanate obtained in the production process as described above can be preferably used as a production raw material of polyurethane foam, paints, adhesives or the like. Since this process enables isocyanate to be efficiently produced without using extremely toxic phosgene, the present invention is industrially extremely significant.

EXAMPLES

Although the following provides a detailed explanation of the present invention based on examples thereof, the scope of the present invention is not limited by these examples.

<Analytical Methods>

1) NMR Analysis

Apparatus: JNM-A400 FT-NMR system, JEOL Ltd., Japan (1) Preparation of $^1$H and $^{13}$C-NMR Analysis Samples About 0.3 g of sample solution were weighed followed by the addition of about 0.7 g of heavy chloroform (99.8%, Aldrich Corp., USA) and about 0.05 g of internal standard in the form of tetramethyl tin (guaranteed reagent, Wako Pure Chemical Industries, Ltd., Japan) and mixing to uniformity to obtain solutions used as NMR analysis samples.

(2) Quantitative Analysis

Analyses were performed on each standard and quantitative analyses were performed on the analysis sample solutions based on the resulting calibration curve.

2) Liquid Chromatography

Apparatus: LC-10AT system, Shimadzu Corp., Japan

Column: Silica-60 column, Tosoh Corp., Japan, two columns connected in series

Developing solvent: Mixed liquid of hexane/tetrahydrofuran (80/20) (v/v)

Solvent flow rate: 2 mL/min

Column temperature: 35° C.

Detector: R.I. (refractometer)

(1) Liquid Chromatography Analysis Samples

About 0.1 g of sample were weighed followed by the addition of about 1 g of tetrahydrofuran (dehydrated, Wako Pure Chemical Industries, Ltd., Japan) and about 0.02 g of internal standard in the form of bisphenol A (guaranteed reagent, Wako Pure Chemical Industries, Ltd., Japan) and mixing to uniformity to obtain solutions used as liquid chromatography analysis samples.

(2) Quantitative Analysis

Analyses were performed on each standard and quantitative analyses were performed on the analysis sample solutions based on the resulting calibration curve.

3) Gas Chromatography

Apparatus: GC-2010, Shimadzu Corp., Japan

Column: DB-1 column, Agilent Technologies Corp., USA, length: 30 m, inner diameter: 0.250 mm, film thickness: 1.00 µm Column temperature: Held at 50° C. for 5 minutes followed by increasing at the rate of 10° C./min to 200° C.; held at 200° C. for 5 minutes followed by increasing at the rate of 10° C./min to 300° C.

Detector: FID (1) Gas Chromatography Analysis Samples

About 0.05 g of sample were weighed followed by the addition of about 1 g of acetone (dehydrated, Wako Pure Chemical Industries, Ltd., Japan) and about 0.02 g of internal standard in the form of toluene (dehydrated, Wako Pure Chemical Industries, Ltd., Japan) and mixing to uniformity to obtain solutions used as gas chromatography analysis samples.

(2) Quantitative Analysis

Analyses were performed on each standard and quantitative analyses were performed on the analysis sample solutions based on the resulting calibration curve.

Reference Example 1

Production of Bis(3-methylbutyl) Carbonate

Step (I-1): Production of Dialkyl Tin Catalyst 625 g (2.7 mol) of di-n-butyl tin oxide (Sankyo Organic Chemicals Co., Ltd., Japan) and 2020 g (22.7 mol) of 3-methyl-1-butanol (Kuraray Co., Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd.). The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1173 g of reaction liquid were obtained in the flask. Based on the results of $^{119}$Sn, $^{1}$H and $^{13}$C-NMR analyses, 1,1,3,3-tetra-n-butyl-1,3-bis(3-methylbutyloxy)distannoxane was confirmed to have been obtained at a yield of 99% based on di-n-butyl tin oxide. The same procedure was then repeated 12 times to obtain a total of 10335 g of 1,1,3,3-tetra-n-butyl-1,3-bis(3-methylbutyloxy) distannoxane.

Step (I-2): Production of Bis(3-methylbutyl) Carbonate

Bis(3-methylbutyl) carbonate was produced in a continuous production apparatus as shown in FIG. 1. 1,1,3,3-Tetra-n-butyl-1,3-bis(3-methylbutyloxy) distannoxane produced in the manner described above was supplied at the rate of 4388 g/hr from a transfer line 4 to a column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with a distillation column 101 was supplied at the rate of 14953 g/hr from a transfer line 2. The liquid temperature inside reaction vessel 102 was controlled to 160° C. by a heater and a reboiler 112, and the pressure was adjusted to about 120 kPa-G with a pressure control valve. The residence time in the reaction vessel was about 17 minutes. 3-Methyl-1-butanol containing water at the rate of 15037 g/hr from the top of the reaction vessel via a transfer line 6, and 3-methyl-1-butanol at the rate of 825 g/hr via feed line 1, were pumped to distillation column 101 packed with Metal Gauze CY Packing and provided with a reboiler 111 and a condenser 121 to carry out distillative purification. In the top of distillation column 101, a fraction containing a high concentration of water was condensed by condenser 121 and recovered from a recovery line 3. Purified 3-methyl-1-butanol was pumped to column-type reaction vessel 102 via transfer line 2 located in the bottom of distillation column 101. An alkyl tin alkoxide catalyst composition containing di-n-butyl-bis(3-methylbutyloxy) tin and 1,1,3,3-tetra-n-butyl-1,3-bis(3-methylbutyloxy)distannoxane was obtained from the bottom of column-type reaction vessel 102, and supplied to a thin film evaporator 103 (Kobelco Eco-Solutions Co., Ltd., Japan) via a transfer line 5. The 3-methyl-1-butanol was distilled off in thin film evaporator 103 and returned to column-type reaction vessel 102 via a condenser 123, a transfer line 8 and transfer line 4. The alkyl tin alkoxide catalyst composition was pumped from the bottom of thin film evaporator 103 via a transfer line 7 and supplied to an autoclave 104 while adjusting the flow rate of di-n-butyl-bis(3-methylbutyloxy) tin and 1,1,3,3-tetra-n-butyl-1,3-bis(3-methylbutyloxy)distannoxane to about 5130 g/hr. Carbon dioxide was supplied to the autoclave by a transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl) carbonate. This reaction liquid was transferred to a decarbonization tank 105 via a transfer line 10 and a control valve to remove residual carbon dioxide, and the carbon dioxide was recovered from a transfer line 11. Subsequently, the reaction liquid was transferred to a thin film evaporator (Kobelco Eco-Solutions Co., Ltd., Japan) 106 set to about 142° C. and about 0.5 kPa via a transfer line 12 and supplied while adjusting the flow rate of 1,1,3,3-tetra-n-butyl-1,3-bis(3-methylbutyloxy) distannoxane to about 4388 g/hr to obtain a fraction containing bis(3-methylbutyl) carbonate. On the other hand, the evaporation residue was circulated to column-type reaction vessel 102 via transfer line 13 and transfer line 4 while adjusting the flow rate of 1,1,3,3-tetra-n-butyl-1,3-bis(3-methylbutyloxy)distannoxane to about 4388 g/hr. The fraction containing bis(3-methylbutyl) carbonate was supplied to a distillation column 107 packed with Metal Gauze CY packing and equipped with a reboiler 117 and a condenser 127 via a condenser 126 and a transfer line 14 at the rate of 959 g/hr followed by distillative purification to obtain 99 wt % bis(3-methylbutyl) carbonate from a recovery line 15 at the rate of 944 g/hr. When the alkyl tin alkoxide catalyst composition of a transfer line 13 was analyzed by $^{119}$Sn, $^{1}$H and $^{13}$C-NMR analysis, it was found to contain 1,1,3,3-tetra-n-butyl-1,3-bis(3-methylbutyloxy)distannoxane but not contain di-n-butyl-bis(3-methylbutyloxy) tin. After carrying out the above-mentioned continuous operation for about 240 hours, alkyl tin alkoxide catalyst composition was extracted from an extraction line 16 at the rate of 18 g/hr, while 1,1,3,3-tetra-n-butyl-1,3-bis(3-methylbutyloxy)distannoxane produced according to the above process was supplied from a feed line 17 at the rate of 18 g/hr.

Reference Example 2

Production of Dibutyl Carbonate

Step (II-1): Production of Dialkyl Tin Catalyst 692 g (2.78 mol) of di-n-butyl tin oxide and 2000 g (27 mol) of 1-butanol (Wako Pure Chemical Industries, Ltd., Japan) were placed in a 3000 mL volumetric pear-shaped flask. The flask containing the white, slurry-like mixture was attached to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator and reducing pressure inside the system, the purge valve was opened gradually to allow nitrogen to flow into the system and return to normal pressure. The oil bath temperature was set to about 126° C., the flask was immersed in the oil bath and rotation of the evaporator was started. After rotating, stirring and heating for about 30 minutes at normal pressure with the purge valve of the evaporator left open, the mixture boiled and distillation of the low boiling point component began. After maintaining in this state for 8 hours, the purge valve was closed, pressure inside the system was gradually reduced, and residual low boiling point component was distilled off with the pressure inside the system at 76 to 54 kPa. After the low boiling point component no longer appeared, the flask was taken out of the oil bath. The reaction liquid was in the form of a clear liquid. The flask was subsequently taken out of the oil bath, the purge valve was opened gradually and the pressure inside the system was returned to normal pressure. 952 g of Reaction liquid were obtained in the flask. Based on the results of $^{119}$Sn, $^{1}$H and $^{13}$C-NMR analyses, a product in the form of 1,1,3,3-tetra-n-butyl-1,3-di(n-butyloxy)distannoxane was obtained at a yield of 99% based on di-n-butyl tin oxide. The same procedure was then repeated 12 times to obtain a total of 11480 g of 1,1,3,3-tetra-n-butyl-1,3-di(n-butyloxy)distannoxane.

Step (II-2): Production of Dibutyl Carbonate

Carbonic acid ester was produced in a continuous production apparatus as shown in FIG. 1. 1,1,3,3-Tetra-n-butyl-1,3-di(n-butyloxy)distannoxane produced in step (II-1) was supplied at the rate of 4201 g/hr from transfer line 4 into a column-type reaction vessel packed with Mellapak 750Y packing (Sulzer Chemtech Ltd., Switzerland) and having an inner diameter of 151 mm and effective length of 5040 mm, and 1-butanol purified with distillation column 101 was supplied to column-type reaction vessel 102 at the rate of 24717 g/hr from feed line 2. The liquid temperature inside the reaction vessel was controlled to 160° C. by a heater and reboiler 112, and the pressure was adjusted to about 250 kPa-G with a pressure control valve. The residence time in the reaction vessel was about 10 minutes. 1-Butanol containing water at the rate of 24715 g/hr from the top of the reaction vessel via transfer line 6, and 1-butanol at the rate of 824 g/hr via feed line 1, were pumped to distillation column 101 packed with Metal Gauze CY packing (Sulzer Chemtech Ltd., Switzerland) and provided with reboiler 111 and condenser 121 to carry out distillative purification. In the top of distillation column 101, a fraction containing a high concentration of water was condensed by condenser 121 and recovered from transfer line 3. Purified 1-butanol was pumped via transfer line 2 located in the bottom of distillation column 101. An alkyl tin alkoxide catalyst composition containing di-n-butyl tin di-n-butoxide and 1,1,3,3-tetra-n-butyl-1,3-di(n-butyloxy)distannoxane was obtained from the bottom of column-type reaction vessel 102, and supplied to thin film evaporator 103 (Kobelco Eco-Solutions Co., Ltd., Japan) via a transfer line 5. The 1-butanol was distilled off in thin film evaporator 103 and returned to column-type reaction vessel 102 via condenser 123, transfer line 8 and transfer line 4. The alkyl tin alkoxide catalyst composition was pumped from the bottom of thin film evaporator 103 via transfer line 7 and supplied to autoclave 104 while adjusting the flow rate of the active components in the form of dibutyl tin dibutoxide and 1,1,3,3-tetra-n-butyl-1,3-di(butyloxy)distannoxane to about 4812 g/hr. Carbon dioxide was supplied to the autoclave by feed line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via transfer line 10 and a control valve to remove residual carbon dioxide, and the carbon dioxide was recovered from transfer line 11. Subsequently, the reaction liquid was pumped to thin film evaporator 106 (Kobelco Eco-Solutions Co., Ltd., Japan) set to 140° C. and about 1.4 kPa via transfer line 12 and supplied while adjusting the flow rate of the 1,1,3,3-tetra-n-butyl-1,3-di(n-butyloxy)distannoxane to about 4201 g/hr to obtain a fraction containing dibutyl carbonate. On the other hand, the evaporation residue was circulated to column-type reaction vessel 102 via transfer line 13 and transfer line 4 while adjusting the flow rate of 1,1,3,3-tetra-n-butyl-1,3-di(n-butyloxy) distannoxane to about 4201 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and a transfer line 14 at the rate of 830 g/hr followed by distillative purification to obtain 99 wt % dibutyl carbonate from recovery line 15 at the rate of 814 g/hr. When the alkyl tin alkoxide catalyst composition of transfer line 13 was analyzed by $^{119}$Sn, $^{1}$H and $^{13}$C-NMR analysis, it was found to contain 1,1,3,3-tetra-n-butyl-1,3-di(n-butyloxy)distannoxane but not contain di-n-butyl tin di-n-butoxide. After carrying out the above-mentioned continuous operation for about 600 hours, alkyl tin alkoxide catalyst composition was extracted from extraction line 16 at the rate of 16 g/hr, while 1,1,3,3-tetra-n-butyl-1,3-di(n-butyloxy) distannoxane produced in step (II-1) was supplied from feed line 17 at the rate of 16 g/hr.

Example 1

Step (1-1): Production of N,N'-hexanediyl-bis-carbamic Acid Bis(3-methylbutyl) Ester 2121 g (10.5 mol) of bis(3-methylbutyl) carbonate and 243.6 g (2.1 mol) of hexamethylene diamine (Aldrich Corp., USA) were placed in a 5 L volumetric four-mouth flask, a stirrer was placed in the flask, and a Dimroth condenser and a three-way valve were attached to the flask. After replacing the inside of the system with nitrogen, the four-mouth flask was immersed in an oil bath (OBH-24, Masuda Corp., Japan) heated to 80° C. followed by the addition of 40.5 g of sodium methoxide (28% methanol solution, Wako Pure Chemical Industries, Ltd., Japan) to start the reaction. Samples of the reaction liquid were suitably collected and subjected to NMR analysis, and the reaction was terminated at the time when hexamethylene diamine was no longer detected. As a result of analyzing the resulting solution by liquid chromatography, the solution was found to contain 29.9% by weight of N,N'-hexanediyl-bis-carbamic acid di(3-methylbutyl) ester. The solution was supplied to a column which was packed with an acidic sulfonic acid ion exchange resin (Amberlyst-15 (spheres), Rohm and Haas Co.) adjusted by removing moisture and warmed to 65° C. with an external jacket, to obtain a solution in which the sodium methoxide had been neutralized.

Step (1-2): Distillation of Low Boiling Point Component

The solution obtained in step (1-1) was placed in a 5 L volumetric flask equipped with a three-way valve, a condenser, a distillate collector and a thermometer, and the inside of the flask was replaced with nitrogen in a vacuum. The flask was immersed in an oil bath heated to about 130° C. Distillation was carried out while gradually reducing the pressure in the flask to a final pressure of 0.02 kPa. 1640 g of distillate were obtained. As a result of analyzing by gas chromatography, the distillate was found to be a solution containing 77.6% by weight of bis(3-methylbutyl) carbonate and 22.2% by weight of 3-methyl-1-butanol. In addition, as a result of analyzing the distillation residue obtained in the flask by liquid chromatography, the distillation residue was found to contain 93.9% by weight of N,N'-hexanediyl-bis-carbamic acid bis(3-methylbutyl) ester. In addition, when the distillation residue was analyzed by gas chromatography, the distillation residue was found to contain bis(3-methylbutyl) carbonate at a molar ratio of 0.010 to N,N'-hexanediyl-bis-carbamic acid bis(3-methylbutyl) ester.

Step (1-3): Production of Hexamethylene Diisocyanate by Thermal Decomposition of N,N'-hexanediyl-bis-carbamic Acid Bis(3-methylbutyl) Ester 2450 g of 2,4-di-tert-amylphenol (Tokyo Chemical Industry Co., Ltd., Japan) and 66.1 g of dibutyl tin dilaurate (chemical grade, Wako Pure Chemical Industries, Ltd., Japan) were added to the distillation residue obtained in step (1-2) to obtain a homogeneous solution. When this was analyzed by gas chromatography, the solution was found to contain bis(3-methylbutyl) carbonate at a stoichiometric ratio of 0.0020 to 2,4-di-tert-amylphenol.

Figure 2:
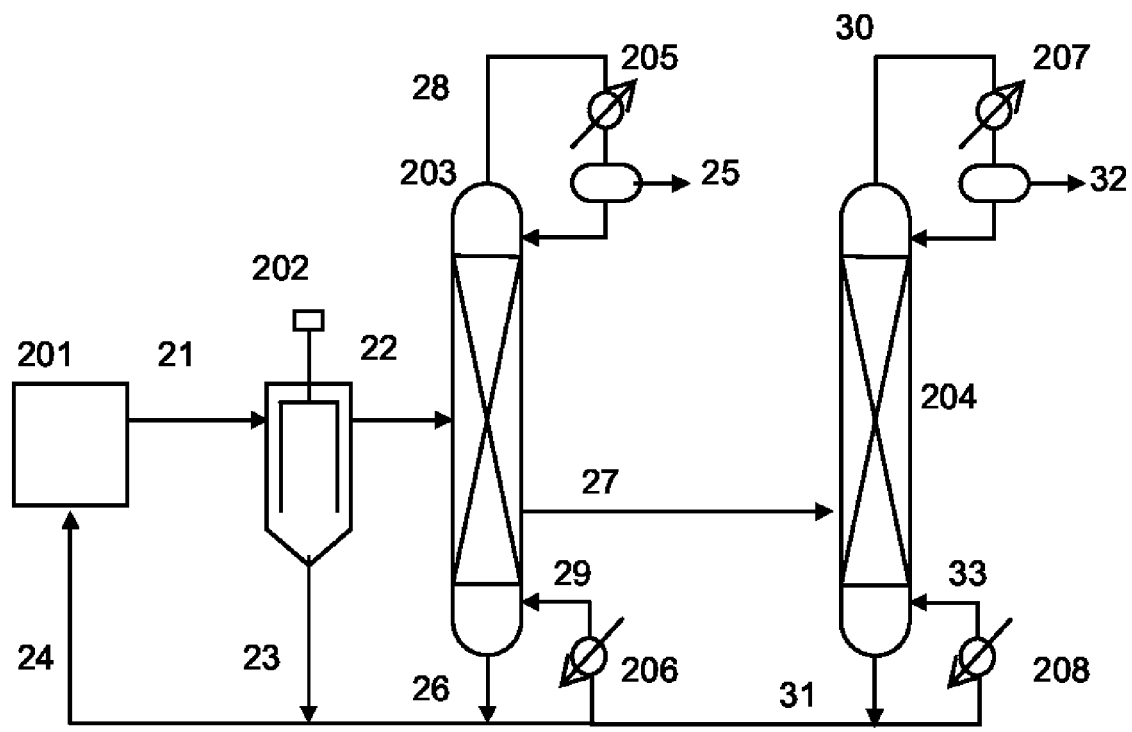
FIG. 2 shows a conceptual drawing illustrating the thermal decomposition reaction apparatus used in an embodiment of the present invention.

A thermal decomposition reaction was then carried out with a reaction apparatus as shown in FIG. 2 using this solution.

A thin film distillation apparatus 202 (Kobelco Eco-Solutions Co., Ltd., Japan) having a heat-conducting surface area of 0.2 m² was heated to 220° C., and the pressure inside the thin film distillation apparatus was set to about 1.3 kPa. The solution prepared in the manner described above was placed in a feed tank 201 and supplied to the thin film distillation apparatus via a line 21 at the rate of about 980 g/hr. A liquid component was extracted from a line 23 provided in the bottom of thin film distillation apparatus 202 and returned to feed tank 201 via a line 24. A gaseous component consisting of hexamethylene diisocyanate, 3-methyl-1-butanol and 2,4-di-tert-amylphenol was extracted from line 22 provided in the upper portion of thin film distillation apparatus 202. This gaseous component was introduced into a distillation column 203, the 3-methyl-1-butanol was separated, and a portion of the high boiling point component was returned to feed tank 201 through line 24 via a line 26 provided in the bottom of distillation column 203. A gaseous component containing hexamethylene diisocyanate and 2,4-di-tert-amylphenol was extracted from a line 27 provided in distillation column 203 and introduced into a distillation column 204. The hexamethylene diisocyanate was separated in this distillation column 204. After carrying out the reaction for 13 hours, 330 g of a solution were recovered from a line 32, and as a result of analyzing by $^1H$ and $^{13}C$-NMR analysis, the solution was found to contain 99% by weight of hexamethylene diisocyanate. The yield based on hexamethylene diamine was 93.5%. In addition, there were no substances observed to be adhered to the inside of the thin film evaporator following the reaction. There were no pentenes detected in the low boiling point component presumed to have originated from denaturation of 2,4-di-tert-amylphenol.

Example 2

Step (2-1): Production of N,N'-hexanediyl-bis-carbamic Acid Bis(3-methylbutyl) Ester The same method as step (1-1) of Example 1 was carried out with the exception of using 2158 g (10.7 mol) of bis(3-methylbutyl) carbonate, 225.4 g (1.94 mol) of hexamethylene diamine and 3.7 g of sodium methoxide (28% methanol solution) to obtain a solution containing 27.9% by weight of N,N'-hexanediyl-bis-carbamic acid bis(3-methylbutyl) ester in the solution.

Step (2-2): Distillation of Low Boiling Point Component 1707 g of a distillate were obtained when distillation of the low boiling point component was carried out in the same manner as step (1-1) of Example 1 using the solution obtained in step (2-1) instead of the solution obtained in step (1-1). When analyzed by gas chromatography, the distillate was found to be a solution containing 80.2% by weight of bis(3-methylbutyl) carbonate and 19.7% by weight of 3-methyl-1-butanol. In addition, when the distillation residue obtained in the flask was analyzed by liquid chromatography, the distillation residue was found to contain 98.2% by weight of N,N'-hexanediyl-bis-carbamic acid bis(3-methylbutyl) ester. In addition, when the distillation residue was analyzed by gas chromatography, the distillation residue was found to contain bis(3-methylbutyl) carbonate at a molar ratio of 0.012 to N,N'-hexanediyl-bis-carbamic acid bis(3-methylbutyl) ester.

Step (2-3): Production of Hexamethylene Diisocyanate by Thermal Decomposition of N,N'-hexanediyl-bis-carbamic Acid Bis(3-methylbutyl) Ester 1177 g of 2,6-dimethylphenol and 60.9 g of dibutyl tin dilaurate were added to the distillation residue obtained in step (2-2) to obtain a homogeneous solution. When this solution was analyzed by gas chromatography, the solution was found to contain bis(3-methylbutyl) carbonate at a stoichiometric ratio of 0.0024 to 2,6-dimethylphenol.

Figure 3:
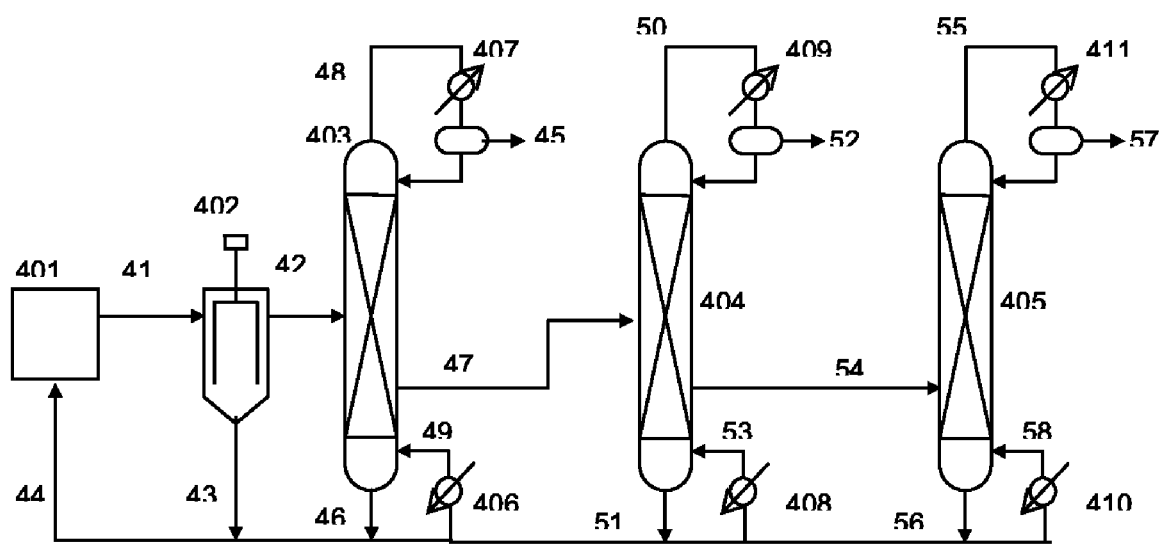
FIG. 3 shows a conceptual drawing illustrating the thermal decomposition reaction apparatus used in an embodiment of the present invention; and,
FIG. 4 shows a conceptual drawing illustrating the isocyanate production apparatus used in an embodiment of the present invention.

A thermal decomposition reaction was then carried out with the reaction apparatus as shown in FIG. 3 using this solution.

A thin film distillation apparatus 402 (Kobelco Eco-Solutions Co., Ltd., Japan) having a heat-conducting surface area of 0.2 m² was heated to 220° C., and the pressure inside the thin film distillation apparatus was set to about 1.3 kPa. The solution prepared in the manner described above was placed in a feed tank 401 and supplied to the thin film distillation apparatus via a line 41 at the rate of about 980 g/hr. A liquid component was extracted from a line 43 provided in the bottom of thin film distillation apparatus 402 and returned to feed tank 401 via a line 44. A gaseous component containing hexamethylene diisocyanate, 3-methyl-1-butanol and 2,6- dimethylphenol was extracted from a line 42 provided in the upper portion of thin film distillation apparatus 402. This gaseous component was introduced into a distillation column 403, the 3-methyl-1-butanol was separated, and a portion of the high boiling point component was returned to feed tank 401 through line 44 via a line 46 provided in the bottom of distillation column 403. A gaseous component containing hexamethylene diisocyanate and 2,6-dimethylphenol was extracted from a line 47 provided in distillation column 403 and introduced into a distillation column 404. The 2,6-dimethylphenol was separated in this distillation column 404, and the 2,6-dimethylphenol was recovered from a line 52. A gaseous component containing hexamethylene diisocyanate was extracted from a line 54 provided in distillation column 404 and introduced into a distillation column 405. The hexamethylene diisocyanate was separated by distillative separation in the distillation column 405 and recovered from a line 57. After carrying out the reaction for 13 hours, 304 g of a solution were recovered from line 57, and as a result of analyzing by $^1$H and $^{13}$C-NMR analysis, the solution was found to contain 99% by weight of hexamethylene diisocyanate. The yield based on hexamethylene diamine was 93.4%. In addition, there were no substances observed to be adhered to the inside of the thin film evaporator following the reaction. There were no compounds detected in the low boiling point component presumed to have originated from denaturation of 2,6-dimethylphenol.

Example 3

Step (3-1): Production of
N,N'-hexanediyl-bis-carbamic Acid Di(n-butyl) Ester

The same method as step (1-1) of Example 1 was carried out with the exception of using 1777 g (10.2 mol) of dibutyl carbonate instead of bis(3-methylbutyl) carbonate, and using 237.0 g (2.04 mol) of hexamethylene diamine and 19.7 g of sodium methoxide (28% methanol solution) to obtain a solution containing 31.6% by weight of N,N'-hexanediyl-bis-carbamic acid di(n-butyl) ester.

Step (3-2): Distillation of Low Boiling Point Component 1354 g of a distillate were obtained when distillation of the low boiling point component was carried out in the same manner as step (1-1) of Example 1 using the solution obtained in step (3-1) instead of the solution obtained in step (1-1). When analyzed by gas chromatography, the distillate was found to be a solution containing 78.0% by weight of dibutyl carbonate and 21.9% by weight of n-butanol. In addition, when the distillation residue obtained in the flask was analyzed by liquid chromatography, the distillation residue was found to contain 96.3% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.008 to N,N'-hexanediyl-bis-carbamic acid di(n-butyl) ester.

Step (3-3): Production of Hexamethylene
Diisocyanate by Thermal Decomposition of
N,N'-hexanediyl-bis-carbamic Acid Di(n-butyl) Ester 1919 g of 2,4,6-trimethylphenol (Aldrich Corp., USA) and 63.6 g of dibutyl tin dilaurate were added to the distillation residue obtained in step (3-2) to obtain a homogeneous solution. When this was analyzed by gas chromatography, the solution was found to contain dibutyl carbonate at a stoichiometric ratio of 0.0011 to 2,4,6-trimethylphenol. 314 g of a solution were recovered from line 57 by carrying out the same method as step (2-3) of Example 2 using the solution. As a result of analyzing the solution by $^1$H and $^{13}$C-NMR analysis, the solution was found to contain 99% by weight of hexamethylene diisocyanate. The yield based on hexamethylene diamine was 91.8%. In addition, there were no substances observed to be adhered to the inside of the thin film evaporator following the reaction. There were no compounds detected in the low boiling point component presumed to have originated from denaturation of 2,4,6-trimethylphenol.

Example 4

Step (4-1): Production of
N,N'-hexanediyl-bis-carbamic Acid
Bis(3-methylbutyl) Ester The same method as step (1-1) of Example 1 was carried out with the exception of using 2251 g (11.0 mol) of bis(3-methylbutyl) carbonate, 244.3 g (2.10 mol) of hexamethylene diamine and 40.5 g of sodium methoxide (28% methanol solution), and not carrying out neutralization treatment with an ion exchange resin to obtain a solution containing 28.4% by weight of N,N'-hexanediyl-bis-carbamic acid bis(3-methylbutyl) ester.

Step (4-2): Distillation of Low Boiling Point Component 1765 g of a distillate were obtained when the same method as step (1-2) of Example 1 was carried out using the solution obtained in step (4-1) instead of the solution obtained in step (1-1). When analyzed by gas chromatography, the distillate was found to be a solution containing 79.2% by weight of bis(3-methylbutyl) carbonate and 20.8% by weight of 3-methyl-1-butanol. In addition, when the distillation residue obtained in the flask was analyzed by liquid chromatography, the distillation residue was found to contain 93.6% by weight of N,N'-hexanediyl-bis-carbamic acid bis(3-methylbutyl) ester. In addition, when the distillation residue was analyzed by gas chromatography, the distillation residue was found to contain bis(3-methylbutyl) carbonate at a molar ratio of 0.015 to N,N'-hexanediyl-bis-carbamic acid bis(3-methylbutyl) ester.

Step (4-3): Production of Hexamethylene
Diisocyanate by Thermal Decomposition of
N,N'-hexanediyl-bis-carbamic Acid
Bis(3-methylbutyl) Ester 2544 g of 2,4-di-tert-amylphenol and 66.0 g of dibutyl tin dilaurate were added to the distillation residue obtained in step (4-2) to obtain a homogeneous solution. When this was analyzed by gas chromatography, the solution was found to contain bis(3-methylbutyl) carbonate at a stoichiometric ratio of 0.0029 to 2,4-di-tert-amylphenol.

312 g of a solution were recovered from line 32 by carrying out the same method as step (1-3) of Example 1 with the exception of using the solution and using a reaction time of 17 hours. As a result of analyzing the solution by $^1$H and $^{13}$C-NMR analysis, the solution was found to contain 99% by weight of hexamethylene diisocyanate. The yield based on hexamethylene diamine was 88.5%. In addition, there were no substances observed to be adhered to the inside of the thin film evaporator following the reaction. There were no compounds detected in the low boiling point component presumed to have originated from denaturation of 2,4-di-tert-amylphenol.

Example 5

Step (5-1): Production of N,N'-hexanediyl-bis-carbamic Acid Bis(3-methylbutyl) Ester The same method as step (1-1) of Example 1 was carried out with the exception of using 2355 g (11.6 mol) of bis(3-methylbutyl) carbonate, 225.4 g (1.94 mol) of hexamethylene diamine and 11.2 g of sodium methoxide (28% methanol solution) to obtain a solution containing 25.7% by weight of N,N'-hexanediyl-bis-carbamic acid bis(3-methylbutyl) ester.

Step (5-2): Distillation of Low Boiling Point Component 1775 g of a distillate were obtained when the same method as step (1-2) of Example 1 was carried out using the solution obtained in step (5-1) instead of the solution obtained in step (1-1). When analyzed by gas chromatography, the distillate was found to be a solution containing 81.0% by weight of bis(3-methylbutyl) carbonate and 18.9% by weight of 3-methyl-1-butanol.

The distillation residue obtained in the flask was washed with 5.6 L of n-hexane (dehydrated, Wako Pure Chemical Industries, Ltd., Japan) followed by filtering out a white solid. When this white solid was analyzed by liquid chromatography, the white solid was found to contain 99.8% by weight of N,N'-hexanediyl-bis-carbamic acid bis(3-methylbutyl) ester. In addition, when the white solid was analyzed by gas chromatography, there was no residual bis(3-methylbutyl) detected in the white solid.

Step (5-3): Production of Hexamethylene Diisocyanate by Thermal Decomposition of N,N'-hexanediyl-bis-carbamic Acid Bis(3-methylbutyl) Ester 2018 g of 2,4-di-tert-amylphenol and 54.4 g of dibutyl tin dilaurate were added to the white solid obtained in step (5-2) to obtain a homogeneous solution.

The same method as step (1-3) of Example 1 was carried out with the exception of storing the solution for 150 hours in feed tank 201 heated to 80° C. followed by reacting for 16 hours to recover 266 g of a solution from line 32. As a result of analyzing this solution by $^1$H and $^{13}$C-NMR analysis, the solution was found to contain 99% by weight of hexamethylene diisocyanate. The yield based on hexamethylene diamine was 86.2%. In addition, there were no substances observed to be adhered to the inside of the thin film evaporator following the reaction. There were compounds detected in the low boiling point component presumed to have originated from denaturation of 2,4-di-tert-amylphenol.

Example 6

Step (6-1): Production of N,N'-hexanediyl-bis-carbamic Acid Di(n-butyl) Ester

The same method as step (1-1) of Example 1 was carried out with the exception of using 1829.5 g (10.5 mol) of dibutyl carbonate instead of bis(3-methylbutyl) carbonate, and using 244.0 g (2.10 mol) of hexamethylene diamine and 40.5 g of sodium methoxide (28% methanol solution) to obtain a solution containing 34.1% by weight of N,N'-hexanediyl-bis-carbamic acid di(n-butyl) ester.

Step (6-2): Distillation of Low Boiling Point Component 1458 g of a distillate were obtained when the same method as step (1-2) of Example 1 was carried out using the solution obtained in step (6-1) instead of the solution obtained in step (1-1). When analyzed by gas chromatography, the distillate was found to be a solution containing 74.9% by weight of dibutyl carbonate and 25.0% by weight of n-butanol. In addition, when the distillation residue obtained in the flask was analyzed by liquid chromatography, the distillation residue was found to contain 93.4% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.020 to N,N'-hexanediyl-bis-carbamic acid di(n-butyl) ester.

Step (6-3): Production of Hexamethylene Diisocyanate by Thermal Decomposition of N,N'-hexanediyl-bis-carbamic Acid Di(n-butyl) Ester 2496 g of 2,4-di-tert-amylphenol and 66.0 g of dibutyl tin dilaurate were added to the distillation residue obtained in step (6-2) to obtain a homogeneous solution.

324 g of a solution were recovered from line 32 by carrying out the same method as Step (1-3) of Example 1 with the exception of using the solution and using a reaction time of 17 hours. As a result of analyzing the solution by $^1$H and $^{13}$C-NMR analysis, the solution was found to contain 99% by weight of hexamethylene diisocyanate. The yield based on hexamethylene diamine was 92.0%. In addition, there were no substances observed to be adhered to the inside of the thin film evaporator following the reaction. There were no compounds detected in the low boiling point component presumed to have originated from denaturation of 2,4-di-tert-amylphenol.

Example 7

Step (7-1): Production of N,N'-hexanediyl-bis-carbamic Acid Di(n-butyl) Ester

The same method as step (1-1) of Example 1 was carried out with the exception of using 1916 g (11.0 mol) of dibutyl carbonate instead of bis(3-methylbutyl) carbonate, and using 255.5 g (2.20 mol) of hexamethylene diamine and 42.4 g of sodium methoxide (28% methanol solution) to obtain a solution containing 34.1% by weight of N,N'-hexanediyl-bis-carbamic acid di(n-butyl) ester.

Step (7-2): Distillation of Low Boiling Point Component 1524 g of a distillate were obtained when the same method as step (1-2) of Example 1 was carried out using the solution obtained in step (7-1) instead of the solution obtained in step (1-1). When analyzed by gas chromatography, the distillate was found to be a solution containing 74.8% by weight of dibutyl carbonate and 25.1% by weight of 1-butanol. In addition, when the distillation residue obtained in the flask was analyzed by liquid chromatography, the distillation residue was found to contain 93.1% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.032 to N,N'-hexanediyl-bis-carbamic acid di(n-butyl) ester.

Step (7-3): Production of Hexamethylene Diisocyanate by Thermal Decomposition of N,N'-hexanediyl-bis-carbamic Acid Di(n-butyl) Ester 2331 g of 2,4-di-tert-butylphenol and 68.7 g of dibutyl tin dilaurate were added to the distillation residue obtained in step (7-2) to obtain a homogeneous solution.

336 g of a solution were recovered from line 32 by carrying out the same method as Step (1-3) of Example 1 with the exception of using the solution and using a reaction time of 18 hours. As a result of analyzing the solution by $^1$H and $^{13}$C-NMR analysis, the solution was found to contain 99% by weight of hexamethylene diisocyanate. The yield based on hexamethylene diamine was 90.9%. There were no substances observed to be adhered to the inside of the thin film evaporator following the reaction. In addition, there were no compounds detected in the low boiling point component presumed to have originated from denaturation of 2,4-di-tert-butylphenol.

Example 8

Step (8-1): Production of N,N'-hexanediyl-bis-carbamic Acid Dimethyl Ester

The same method as step (1-1) of Example 1 was carried out with the exception of using 1241 g (13.8 mol) of dimethyl carbonate (Aldrich Corp., USA) instead of bis(3-methylbutyl) carbonate, and using 290.5 g (2.50 mol) of hexamethylene diamine and 24.1 g of sodium methoxide (28% methanol solution) to obtain a solution containing 37.2% by weight of N,N'-hexanediyl-bis-carbamic acid dimethyl ester.

Step (8-2): Distillation of Low Boiling Point Component 949 g of a distillate were obtained when the same method as step (1-2) of Example 1 was carried using the solution obtained in step (8-1) instead of the solution obtained in step (1-1). When analyzed by gas chromatography, the distillate was found to be a solution containing 83.3% by weight of dimethyl carbonate and 16.6% by weight of methanol. In addition, when the distillation residue obtained in the flask was analyzed by liquid chromatography, the distillation residue was found to contain 95.7% by weight of N,N'-hexanediyl-bis-carbamic acid dimethyl ester. In addition, when the distillation residue was analyzed by gas chromatography, dimethyl carbonate was not detected in the distillation residue.

Step (8-3): Production of Hexamethylene Diisocyanate by Thermal Decomposition of N,N'-hexanediyl-bis-carbamic Acid Dimethyl Ester 1692 g of 2,4,6-trimethylphenol and 78.5 g of dibutyl tin dilaurate were added to the distillation residue obtained in step (8-2) to obtain a homogeneous solution in which the dimethyl carbonate was added at a molar ratio of 0.004 to the 2,4,6-trimethylphenol.

384 g of a solution were recovered from line 57 by carrying out the same method as Step (2-3) of Example 2 with the exception of using the solution and using a reaction time of 18 hours. As a result of analyzing the solution by $^1$H and $^{13}$C-NMR analysis, the solution was found to contain 99% by weight of hexamethylene diisocyanate. The yield based on hexamethylene diamine was 91.4%. There were no substances observed to be adhered to the inside of the thin film evaporator following the reaction. In addition, there were no compounds detected in the low boiling point component presumed to have originated from denaturation of 2,4,6-trimethylphenol.

Example 9

Step (9-1): Production of N,N'-hexanediyl-bis-carbamic Acid Dimethyl Ester

The same method as step (1-1) of Example 1 was carried out with the exception of using 1355 g (15.0 mol) of dimethyl carbonate instead of bis(3-methylbutyl) carbonate, and using 290.5 g (2.50 mol) of hexamethylene diamine and 24.1 g of sodium methoxide (28% methanol solution) to obtain a solution containing 34.7% by weight of N,N'-hexanediyl-bis-carbamic acid dimethyl ester.

Step (9-2): Distillation of Low Boiling Point Component 1062 g of a distillate were obtained when the same method as step (1-1) of Example 1 was carried using the solution obtained in step (9-1) instead of the solution obtained in step (1-1). When analyzed by gas chromatography, the distillate was found to be a solution containing 85.0% by weight of dimethyl carbonate and 14.9% by weight of methanol. In addition, when the distillation residue obtained in the flask was analyzed by liquid chromatography, the distillation residue was found to contain 95.7% by weight of N,N'-hexanediyl-bis-carbamic acid dimethyl ester. In addition, when the distillation residue was analyzed by gas chromatography, dimethyl carbonate was not detected in the distillation residue.

Step (9-3): Production of Hexamethylene Diisocyanate by Thermal Decomposition of N,N'-hexanediyl-bis-carbamic Acid Dimethyl Ester 1865 g of 2-tert-butylphenol (Aldrich Corp., USA) and 78.5 g of dibutyl tin dilaurate were added to the distillation residue obtained in step (9-2) to obtain a homogeneous solution in which the dimethyl carbonate was added at a molar ratio of 0.002 to the 2-tert-butylphenol. 396 g of a solution were recovered from line 57 by carrying out the same method as Step (2-3) of Example 2 with the exception of using the solution. As a result of analyzing the solution by $^1$H and $^{13}$C-NMR analysis, the solution was found to contain 99% by weight of hexamethylene diisocyanate. The yield based on hexamethylene diamine was 94.4%. In addition, there were no substances observed to be adhered to the inside of the thin film evaporator following the reaction. There were no butenes detected in the low boiling point component presumed to have originated from denaturation of 2-tert-butylphenol.

Example 10

Step (10-1): Production of N,N'-hexanediyl-bis-carbamic Acid Dimethyl Ester

The same method as step (1-1) of Example 1 was carried out with the exception of using 1463 g (16.2 mol) of dimethyl carbonate instead of bis(3-methylbutyl) carbonate, and using 313.7 g (2.70 mol) of hexamethylene diamine and 26.0 g of sodium methoxide (28% methanol solution) to obtain a solution containing 34.7% by weight of N,N'-hexanediyl-bis-carbamic acid dimethyl ester.

Step (10-2): Distillation of Low Boiling Point Component 1146 g of a distillate were obtained when the same method as step (1-1) of Example 1 was carried using the solution obtained in step (10-1) instead of the solution obtained in step (1-1). When analyzed by gas chromatography, the distillate was found to be a solution containing 85.0% by weight of dimethyl carbonate and 14.8% by weight of methanol. In addition, when the distillation residue obtained in the flask was analyzed by liquid chromatography, the distillation residue was found to contain 95.6% by weight of N,N'-hexanediyl-bis-carbamic acid dimethyl ester. In addition, when the distillation residue was analyzed by gas chromatography, dimethyl carbonate was not detected in the distillation residue.

Step (10-3): Production of Hexamethylene Diisocyanate by Thermal Decomposition of N,N'-hexanediyl-bis-carbamic Acid Dimethyl Ester 1865 g of 2-tert-butylphenol and 78.5 g of dibutyl tin dilaurate were added to the distillation residue obtained in step (10-2) to obtain a homogeneous solution. 388 g of a solution were recovered from line 57 by carrying out the same method as Step (2-3) of Example 2 using the solution. As a result of analyzing the solution by $^1$H and $^{13}$C-NMR analysis, the solution was found to contain 99% by weight of hexamethylene diisocyanate. The yield based on hexamethylene diamine was 85.4%. In addition, there were no substances observed to be adhered to the inside of the thin film evaporator following the reaction. There were butenes detected in the low boiling point component presumed to have originated from denaturation of 2-tert-butylphenol.

Example 11

Step (11-1): Production of N,N'-hexanediyl-bis-carbamic Acid Bis(3-methylbutyl) Ester 304.5 g (2.62 mol) of hexamethylene diamine, 313.2 g (5.22 mol) of urea (Wako Pure Chemical Industries, Ltd., Japan) and 4611 g of 3-methyl-1-butanol (reagent grade, Wako Pure Chemical Industries, Ltd., Japan) were placed in a 10 L volumetric four-mouth flask equipped with a reflux condenser, a thermometer, a stirrer and a gas feed tube. The flask was immersed in an oil bath (OBH-24, Masuda Corp., Japan) heated to 155° C. and the reaction was carried out while introducing nitrogen gas at the rate of 20 L/hr from a ball filter that reached to the bottom of the reaction vessel. Samples of the reaction liquid were suitably collected and subjected to NMR analysis, and the reaction was terminated at the time when hexamethylene diamine was no longer detected. A solution containing ammonia was distilled from the upper portion of the reaction vessel.

The flask was connected to a rotary evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd.), the oil bath temperature was set to 130° C., and the low boiling point component was distilled off at a pressure of 0.02 kPa to obtain a distillation residue inside the flask. When the distillation residue was analyzed by liquid chromatography, the distillation residue was found to contain 99.0% by weight of N,N'-hexanediyl-bis-carbamic acid bis(3-methylbutyl) ester. In addition, when the distillation residue was analyzed by gas chromatography, it was found to contain urea at a molar ratio of 0.005 to the N,N'-hexanediyl-bis-carbamic acid bis(3-methylbutyl) ester.

Step (11-2): Production of Hexamethylene Diisocyanate by Thermal Decomposition of N,N'-hexanediyl-bis-carbamic Acid Bis(3-methylbutyl) Ester 1787 g of 2,4-di-tert-butylphenol (Wako Pure Chemical Industries, Ltd., Japan) and 54.7 g of dibutyl tin dilaurate were added to the distillation residue obtained in step (11-1) to obtain a homogeneous solution. When this was analyzed by gas chromatography, the solution was found to contain urea at a stoichiometric ratio of 0.0010 to 2,4-di-tert-amylphenol. 273 g of a solution were recovered from line 32 by carrying out the same method as Step (1-3) of Example 1 with the exception of storing the solution for 150 hours in feed tank 201 heated to 80° C. As a result of analyzing by $^1$H and $^{13}$C-NMR analysis, the solution was found to contain 99% by weight of hexamethylene diisocyanate. The yield based on hexamethylene diamine was 92.0%. In addition, there were no substances observed to be adhered to the inside of the thin film evaporator following the reaction. There were no butenes detected in the low boiling point component presumed to have originated from denaturation of 2,4-di-tert-butylphenol.

Example 12

Step (12-1): Production of N,N'-hexanediyl-bis-carbamic Acid Bis(3-methylbutyl) Ester The same method as step (1-1) of Example 1 was carried out with the exception of using 2326 g (11.5 mol) of bis(3-methylbutyl) carbonate, 267.3 g (2.30 mol) of hexamethylene diamine and 44.4 g of sodium methoxide (28% methanol solution) to obtain a solution containing 29.9% by weight of N,N'-hexanediyl-bis-carbamic acid bis(3-methylbutyl) ester.

Step (12-2): Distillation of Low Boiling Point Component 1781 g of a distillate were obtained when distillation of the low boiling point component was carried out in the same manner as step (1-1) of Example 1 using the solution obtained in step (12-1) instead of the solution obtained in step (1-1). When analyzed by gas chromatography, the distillate was found to be a solution containing 78.2% by weight of bis(3-methylbutyl) carbonate and 21.2% by weight of 3-methyl-1-butanol. In addition, when the distillation residue obtained in the flask was analyzed by liquid chromatography, the distillation residue was found to contain 92.4% by weight of N,N'-hexanediyl-bis-carbamic acid bis(3-methylbutyl) ester. In addition, when the distillation residue was analyzed by gas chromatography, the distillation residue was found to contain bis(3-methylbutyl) carbonate at a molar ratio of 0.010 to N,N'-hexanediyl-bis-carbamic acid bis(3-methylbutyl) ester.

Step (12-3): Production of Hexamethylene Diisocyanate by Thermal Decomposition of N,N'-hexanediyl-bis-carbamic Acid Bis(3-methylbutyl) Ester 1801 g of 2-ethoxyphenol (Aldrich Corp., USA) and 72.3 g of dibutyl tin dilaurate were added to the distillation residue obtained in step (12-2) to obtain a homogeneous solution. When this was analyzed by gas chromatography, the solution was found to contain bis(3-methylbutyl) carbonate at a stoichiometric ratio of 0.0018 to 2-ethoxyphenol. 350 g of a solution were recovered from line 57 by carrying out the same method as step (2-3) of Example 2 using the solution. As a result of analyzing by $^1$H and $^{13}$C-NMR analysis, the solution was found to contain 99% by weight of hexamethylene diisocyanate. The yield based on hexamethylene diamine was 90.5%. In addition, there were no substances observed to be adhered to the inside of the thin film evaporator following the reaction. There were no compounds detected in the low boiling point component presumed to have originated from denaturation of 2-ethoxyphenol.

Example 13

Step (13-1): Production of N,N'-hexanediyl-bis-carbamic Acid Bis(3-methylbutyl) Ester The same method as step (1-1) of Example 1 was carried out with the exception of using 1913.7 g (9.50 mol) of bis(3-methylbutyl) carbonate, 255.6 g (2.20 mol) of hexamethylene diamine and 42.4 g of sodium methoxide (28% methanol solution) to obtain a solution containing 34.2% by weight of N,N'-hexanediyl-bis-carbamic acid bis(3-methylbutyl) ester.

Step (13-2): Distillation of Low Boiling Point Component 1401 g of a distillate were obtained when distillation of the low boiling point component was carried out in the same manner as step (1-2) of Example 1 using the solution obtained in step (13-1) instead of the solution obtained in step (1-1). When analyzed by gas chromatography, the distillate was found to be a solution containing 72.5% by weight of bis(3-methylbutyl) carbonate and 27.3% by weight of 3-methyl-1-butanol. In addition, when the distillation residue obtained in the flask was analyzed by liquid chromatography, the distillation residue was found to contain 93.3% by weight of N,N'-hexanediyl-bis-carbamic acid bis(3-methylbutyl) ester. In addition, when the distillation residue was analyzed by gas chromatography, the distillation residue was found to contain bis(3-methylbutyl) carbonate at a molar ratio of 0.023 to N,N'-hexanediyl-bis-carbamic acid bis(3-methylbutyl) ester.

Step (13-3): Production of Hexamethylene Diisocyanate by Thermal Decomposition of N,N'-hexanediyl-bis-carbamic Acid Bis(3-methylbutyl) Ester 3593 g of 2,4-bis(α,α-dimethylbenzyl)phenol and 68.7 g of dibutyl tin dilaurate were added to the distillation residue obtained in step (13-2) to obtain a homogeneous solution.

332 g of a solution were recovered from line 32 by carrying out the same method as step (1-3) of Example 1 using the solution with the exception of using a reaction time of 17 hours. As a result of analyzing by $^1$H and $^{13}$C-NMR analysis, the solution was found to contain 99% by weight of hexamethylene diisocyanate. The yield based on hexamethylene diamine was 89.9%. In addition, there were no substances observed to be adhered to the inside of the thin film evaporator following the reaction. There were no compounds detected in the low boiling point component presumed to have originated from denaturation of 2,4-bis(α,α-dimethylbenzyl)phenol.

Example 14

Step (14-1): Production of N,N'-hexanediyl-bis-carbamic Acid Bis(3-methylbutyl) Ester The same method as step (1-1) of Example 1 was carried out with the exception of using 2124 g (10.5 mol) of bis(3-methylbutyl) carbonate, 244.0 g (2.10 mol) of hexamethylene diamine and 40.5 g of sodium methoxide (28% methanol solution) to obtain a solution containing 29.9% by weight of N,N'-hexanediyl-bis-carbamic acid bis(3-methylbutyl) ester.

Step (14-2): Distillation of Low Boiling Point Component 1631 g of a distillate were obtained when the same method as step (1-2) of Example 1 was carried out using the solution obtained in step (14-1) instead of the solution obtained in step (1-1). When analyzed by gas chromatography, the distillate was found to be a solution containing 77.6% by weight of bis(3-methylbutyl) carbonate and 22.4% by weight of 3-methyl-1-butanol.

The distillation residue obtained in the flask was washed with 6.3 L of n-hexane and a white solid was filtered out. When this white solid was analyzed by liquid chromatography, the white solid was found to contain 99.8% by weight of N,N'-hexanediyl-bis-carbamic acid bis(3-methylbutyl) ester. In addition, when the white solid was analyzed by gas chromatography, there was no residual bis(3-methylbutyl) carbonate detected in the white solid.

Step (14-3): Production of Hexamethylene Diisocyanate by Thermal Decomposition of N,N'-hexanediyl-bis-carbamic Acid Bis(3-methylbutyl) Ester 1762 g of 2-phenylphenol (Aldrich Corp., USA) and 65.4 g of dibutyl tin dilaurate were added to the white solid obtained in step (14-2), and bis(3-methylbutyl) carbonate was further added at a molar ratio of 0.030 to the 2-phenyl phenol to obtain a homogeneous solution.

290 g of a solution were recovered from line 32 by carrying out the same method as step (1-3) of Example 1 with the exception of using this solution and using a reaction time of 19 hours. The yield based on hexamethylene diamine was 82.4%. There were no substances observed to be adhered to the inside of the thin film evaporator following the reaction. In addition, there were no compounds detected in the low boiling point component presumed to have originated from denaturation of 2-phenylphenol.

Example 15

Step (15-1): Production of N,N'-hexanediyl-bis-carbamic Acid Bis(3-methylbutyl) Ester The same method as step (1-1) of Example 1 was carried out with the exception of using 2427 g (12.0 mol) of bis(3- methylbutyl) carbonate, 232.4 g (2.0 mol) of hexamethylene diamine and 38.6 g of sodium methoxide (28% methanol solution) to obtain a solution containing 25.5% by weight of N,N'-hexanediyl-bis-carbamic acid bis(3-methylbutyl) ester.

Step (15-2): Distillation of Low Boiling Point Component 1969 g of a distillate were obtained by carrying out the same method as step (1-2) of Example 1 using the solution obtained in step (15-1) instead of the solution obtained in step (1-1). When analyzed by gas chromatography, the distillate was found to be a solution containing 77.6% by weight of bis(3-methylbutyl) carbonate and 22.4% by weight of 3-methyl-1-butanol.

The distillation residue obtained in the flask was washed with 6.3 L of n-hexane and a white solid was filtered out. When the white solid was analyzed by liquid chromatography, the white solid was found to contain 99.8% by weight of N,N'-hexanediyl-bis-carbamic acid bis(3-methylbutyl) ester. In addition, when the white solid was analyzed by gas chromatography, there was no residual bis(3-methylbutyl) carbonate detected in the white solid.

Step (15-3): Production of Hexamethylene Diisocyanate by Thermal Decomposition of N,N'-hexanediyl-bis-carbamic Acid Bis(3-methylbutyl) Ester 1762 g of 2-phenylphenol and 65.4 g of dibutyl tin dilaurate were added to the white solid obtained in step (15-2) to obtain a homogeneous solution.

253 g of a solution were recovered from line 32 by carrying out the same method as step (1-3) of Example 1 with the exception of using the solution and using a reaction time of 19 hours. As a result of analyzing by $^1$H and $^{13}$C-NMR analysis, the solution was found to contain 99% by weight of hexamethylene diisocyanate. The yield based on hexamethylene diamine was 75.5%. There were no substances observed to be adhered to the inside of the thin film evaporator following the reaction. In addition, there were compounds detected in the low boiling point component presumed to have originated from denaturation of 2-phenylphenol.

Example 16

Step (16-1): Production of N,N'-hexanediyl-bis-carbamic Acid Di(n-butyl) Ester

The same method as step (1-1) of Example 1 was carried out with the exception of using 1916 g (11.0 mol) of dibutyl carbonate instead of bis(3-methylbutyl) carbonate, and using 255.6 g (2.20 mol) of hexamethylene diamine and 21.2 g of sodium methoxide (28% methanol solution) to obtain a solution containing 31.4% by weight of N,N'-hexanediyl-bis-carbamic acid di(n-butyl) ester.

Step (16-2): Distillation of Low Boiling Point Component 1473 g of a distillate were obtained by carrying out the same method as step (1-2) of Example 1 using the solution obtained in step (16-1) instead of the solution obtained in step (1-1). When analyzed by gas chromatography, the distillate was found to be a solution containing 78.4% by weight of dibutyl carbonate and 21.6% by weight of n-butanol. In addition, when the distillation residue obtained in the flask was analyzed by liquid chromatography, the distillation residue was found to contain 95.8% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.006 to N,N'-hexanediyl-bis-carbamic acid di(n-butyl) ester.

Step (16-3): Production of Hexamethylene Diisocyanate by Thermal Decomposition of N,N'-hexanediyl-bis-carbamic Acid Di(n-butyl) Ester 2397 g of nonylphenol (Aldrich Corp., USA) and 68.7 g of dibutyl tin dilaurate were added to the distillation residue obtained in step (16-2) to obtain a homogeneous solution. When this was analyzed by gas chromatography, the solution was found to contain dibutyl carbonate at a stoichiometric ratio of 0.0012 to nonylphenol.

282 g of a solution were recovered from line 32 by carrying out the same method as step (1-3) of Example 1 with the exception of using the solution and using a reaction time of 15 hours. As a result of analyzing the solution by $^1$H and $^{13}$C-NMR analysis, the solution was found to contain 99% by weight of hexamethylene diisocyanate. The yield based on hexamethylene diamine was 76.1%. In addition, there were no substances observed to be adhered to the inside of the thin film evaporator following the reaction. There were no nonenes detected in the low boiling point component presumed to have originated from denaturation of nonylphenol.

Example 17

Step (17-1): Production of N,N'-hexanediyl-bis-carbamic Acid Di(n-butyl) Ester

The same method as step (1-1) of Example 1 was carried out with the exception of using 1964 g (11.3 mol) of dibutyl carbonate instead of bis(3-methylbutyl) carbonate, and using 267.3 g (2.30 mol) of hexamethylene diamine and 22.2 g of sodium methoxide (28% methanol solution) to obtain a solution containing 32.0% by weight of N,N'-hexanediyl-bis-carbamic acid di(n-butyl) ester.

Step (17-2): Distillation of Low Boiling Point Component 1506 g of a distillate were obtained by carrying out the same method as step (1-2) of Example 1 using the solution obtained in step (17-1) instead of the solution obtained in step (1-1). When analyzed by gas chromatography, the distillate was found to be a solution containing 77.6% by weight of dibutyl carbonate and 22.2% by weight of n-butanol. In addition, when the distillation residue obtained in the flask was analyzed by liquid chromatography, the distillation residue was found to contain 96.7% by weight of N,N'-hexanediyl-bis-carbamic acid di(n-butyl) ester. In addition, when the distillation residue was analyzed by gas chromatography, there was no dibutyl carbonate detected in the distillation residue.

Step (17-3): Production of Hexamethylene Diisocyanate by Thermal Decomposition of N,N'-hexanediyl-bis-carbamic Acid Di(n-butyl) Ester 2509 g of nonylphenol and 72.0 g of dibutyl tin dilaurate were added to the distillation residue obtained in step (17-2) to obtain a homogeneous solution.

264 g of a solution were recovered from line 32 by carrying out the same method as step (1-3) of Example 1 with the exception of using the solution and using a reaction time of 15 hours. As a result of analyzing the solution by $^1$H and $^{13}$C-NMR analysis, the solution was found to contain 99% by weight of hexamethylene diisocyanate. The yield based on hexamethylene diamine was 68.3%. In addition, there were no substances observed to be adhered to the inside of the thin film evaporator following the reaction. There were nonenes detected in the low boiling point component presumed to have originated from denaturation of nonylphenol.

Example 18

Step (18-1): Production of N,N'-hexanediyl-bis-carbamic Acid Di(n-butyl) Ester

The same method as step (1-1) of Example 1 was carried out with the exception of using 1777 g (10.2 mol) of dibutyl carbonate instead of bis(3-methylbutyl) carbonate, and using 237.0 g (2.04 mol) of hexamethylene diamine and 19.7 g of sodium methoxide (28% methanol solution) to obtain a solution containing 27.1% by weight of N,N'-hexanediyl-bis-carbamic acid di(n-butyl) ester.

Step (18-2): Distillation of Low Boiling Point Component 1631 g of a distillate were obtained by carrying out distillation of the low boiling point component in the same manner as step (1-1) of Example 1 using the solution obtained in step (18-1) instead of the solution obtained in step (1-1). When analyzed by gas chromatography, the distillate was found to be a solution containing 82.8% by weight of dibutyl carbonate and 17.2% by weight of n-butanol. In addition, when the distillation residue obtained in the flask was analyzed by liquid chromatography, the distillation residue was found to contain 98.1% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.006 to N,N'-hexanediyl-bis-carbamic acid di(n-butyl) ester.

Step (18-3): Production of Hexamethylene Diisocyanate by Thermal Decomposition of N,N'-hexanediyl-bis-carbamic Acid Di(n-butyl) Ester 1451 g of phenol (for nucleic acid extraction, Wako Pure Chemical Industries, Ltd., Japan) and 60.9 g of dibutyl tin dilaurate were added to the distillation residue obtained in step (18-2) to obtain a homogeneous solution. When this was analyzed by gas chromatography, the solution was found to contain dibutyl carbonate at a stoichiometric ratio of 0.00075 to phenol. 259 g of a solution were recovered from line 57 by carrying out the same method as step (2-3) of Example 2 using the solution. As a result of analyzing the solution by $^1$H and $^{13}$C-NMR analysis, the solution was found to contain 99% by weight of hexamethylene diisocyanate. The yield based on hexamethylene diamine was 79.5%. In addition, there were no substances observed to be adhered to the inside of the thin film evaporator following the reaction. There were no compounds detected in the low boiling point component presumed to have originated from denaturation of phenol.

Example 19

Step (19-1): Production of 3-((3-methylbutyl)oxycarbonylamino-methyl)-3,5,5-trimethylcyclohexylcarbamic Acid (3-methylbutyl) Ester 2080 g (10.3 mol) of bis(3-methylbutyl) carbonate and 318.5 g (1.87 mol) of 3-aminomethyl-3,5,5-trimethylcyclohexylamine (Aldrich Corp., USA) were placed in a 5 L volumetric four-mouth flask, a stirrer was placed in the flask, and a Dimroth condenser and a three-way valve were attached to the flask. After replacing the inside of the system with nitrogen, the four-mouth flask was immersed in an oil bath heated to 100° C. followed by the addition of 18.0 g of sodium methoxide (28% methanol solution) to start the reaction. Samples of the reaction liquid were suitably collected and subjected to NMR analysis, and the reaction was terminated at the time when 3-aminomethyl-3,5,5-trimethylcyclohexylamine was no longer detected. The resulting solution was supplied to a column which was packed with an acidic sulfonic acid ion exchange resin (Amberlyst-15 (spheres), Rohm and Haas Co.) adjusted by removing moisture and warmed to 65° C. with an external jacket, to obtain a solution in which the sodium methoxide had been neutralized. As a result of analyzing the solution by liquid chromatography, the solution was found to contain 30.7% by weight of 3-((3-methyl butyl) oxycarbonylamino-methyl)-3,5,5-trimethylcyclohexylcarbamic acid (3-methylbutyl) ester.

Step (19-2): Distillation of Low Boiling Point Component 1640 g of a distillate were obtained when the low boiling point component was distilled off in the same manner as step (1-1) of Example 1 using the solution obtained in step (19-1) instead of the solution obtained in step (1-1). As a result of analyzing by gas chromatography, the distillate was found to be a solution containing 80.3% by weight of bis(3-methylbutyl) carbonate and 19.6% by weight of 3-methyl-1-butanol. In addition, as a result of analyzing the distillation residue obtained in the flask by liquid chromatography, the distillation residue was found contain 96.4% by weight of 3-((3-methylbutyl)oxycarbonylamino-methyl)-3,5,5-trimethylcyclohexylcarbamic acid (3-methylbutyl) ester. In addition, when the distillation residue was analyzed by gas chromatography, the distillation residue was found to contain bis(3-methylbutyl) carbonate at a molar ratio of 0.001 to 3-((3-methylbutyl)oxycarbonylamino-methyl)-3,5,5-trimethylcyclohexylcarbamic acid (3-methylbutyl) ester.

Step (19-3): Production of Isophorone Diisocyanate by Thermal Decomposition of 3-((3-methylbutyl) oxycarbonylamino-methyl)-3,5,5-trimethylcyclohexylcarbamic Acid (3-methylbutyl) Ester 2171 g of 2,4-di-tert-amylphenol and 58.6 g of dibutyl tin dilaurate were added to the distillation residue obtained in step (19-2) to obtain a homogeneous solution. When this was analyzed by gas chromatography, the solution was found to contain bis(3-methylbutyl) carbonate at a stoichiometric ratio of 0.0020 to 2,4-di-tert-amylphenol.

378 g of a solution were recovered from line 32 by carrying out the same method as step (1-3) of Example 1 with the exception of using the solution and using a reaction time of 13 hours. As a result of analyzing the solution by $^1$H and $^{13}$C-NMR analysis, the solution was found to contain 99% by weight of isophorone diisocyanate. The yield based on 3-aminomethyl-3,5,5-trimethylcyclohexylamine was 91.2%. In addition, there were no substances observed to be adhered to the inside of the thin film evaporator following the reaction. There were no pentenes detected in the low boiling point component presumed to have originated from denaturation of 2,4-di-tert-amylphenol.

Example 20

Step (20-1): Production of 3-((n-butyl)oxycarbonylamino-methyl)-3,5,5-trimethylcyclohexylcarbamic Acid (n-butyl) Ester The same method as step (19-1) of Example 19 was carried out with the exception of using 1521 g (8.7 mol) of dibutyl carbonate instead of bis(3-methylbutyl) carbonate, and using 330.4 g (1.94 mol) of 3-aminomethyl-3,5,5-trimethylcyclohexylamine and 11.2 g of sodium methoxide (28% methanol solution) to obtain a solution containing 37.8% by weight of 3-((n-butyl)oxycarbonylamino-methyl)-3,5,5-trimethylcyclohexylcarbamic acid (n-butyl) ester.

Step (20-2): Distillation of Low Boiling Point Component 1142 g of a distillate were obtained when the low boiling point component was distilled off in the same manner as step (1-1) of Example 1 using the solution obtained in step (20-1) instead of the solution obtained in step (1-1). As a result of analyzing by gas chromatography, the distillate was found to be a solution containing 75.0% by weight of dibutyl carbonate and 24.5% by weight of 1-butanol. In addition, as a result of analyzing the distillation residue obtained in the flask by liquid chromatography, the distillation residue was found contain 97.8% by weight of 3-((n-butyl)oxycarbonylamino-methyl)-3,5,5-trimethylcyclohexylcarbamic acid (n-butyl) ester. In addition, when the distillation residue was analyzed by gas chromatography, the distillation residue was found to contain dibutyl carbonate at a molar ratio of 0.007 to 3-((n-butyl)oxycarbonylamino-methyl)-3,5,5-trimethylcyclohexylcarbamic acid (n-butyl) ester.

Step (20-3): Production of Isophorone Diisocyanate by Thermal Decomposition of 3-((n-butyl)oxycarbonylamino-methyl)-3,5,5-trimethylcyclohexylcarbamic Acid (n-butyl) Ester 1156 g of 2,6-dimethylphenol and 59.8 g of dibutyl tin dilaurate were added to the distillation residue obtained in step (20-2) to obtain a homogeneous solution. When this was analyzed by gas chromatography, the solution was found to contain dibutyl carbonate at a stoichiometric ratio of 0.0014 to 2,6-dimethylphenol.
387 g of a solution were recovered from line 57 by carrying out the same method as step (2-3) of Example 2 with the exception of using the solution and using a reaction time of 13 hours. As a result of analyzing the solution by $^1$H and $^{13}$C-NMR analysis, the solution was found to contain 99% by weight of isophorone diisocyanate. The yield based on 3-aminomethyl-3,5,5-trimethylcyclohexylamine was 89.8%. In addition, there were no substances observed to be adhered to the inside of the thin film evaporator following the reaction. There were no compounds detected in the low boiling point component presumed to have originated from denaturation of 2,6-dimethylphenol.

Example 21

Step (21-1): Production of 3-(methyloxycarbonylamino-methyl)-3,5,5-trimethylcyclohexylcarbamic Acid Methyl Ester The same method as step (19-1) of Example 19 was carried out with the exception of using 975 g (10.8 mol) of dimethyl carbonate instead of bis(3-methylbutyl) carbonate, using 306.5 g (1.80 mol) of 3-aminomethyl-3,5,5-trimethylcyclohexylamine and 6.9 g of sodium methoxide (28% methanol solution, Wako Pure Chemical Industries, Ltd., Japan), and not carrying out neutralization treatment using an ion exchange resin to obtain a solution containing 39.9% by weight of 3-(methyloxycarbonylamino-methyl)-3,5,5-trimethylcyclohexylcarbamic acid methyl ester.

Step (21-2): Distillation of Low Boiling Point Component 764 g of a distillate were obtained when the low boiling point component was distilled off in the same manner as step (1-1) of Example 1 using the solution obtained in step (21-1) instead of the solution obtained in step (1-1). As a result of analyzing by gas chromatography, the distillate was found to be a solution containing 85.1% by weight of dimethyl carbonate and 14.8% by weight of methanol. In addition, as a result of analyzing the distillation residue obtained in the flask by liquid chromatography, the distillation residue was found contain 98.2% by weight of 3-(methyloxycarbonylamino-methyl)-3,5,5-trimethylcyclohexylcarbamic acid methyl ester. In addition, when the distillation residue was analyzed by gas chromatography, there was no dimethyl carbonate detected in the distillation residue.

Step (21-3): Production of Isophorone Diisocyanate by Thermal Decomposition of 3-(methyloxycarbonylamino-methyl)-3,5,5-trimethylcyclohexylcarbamic Acid Methyl Ester 1219 g of 2,4,6-trimethylphenol and 56.6 g of dibutyl tin dilaurate were added to the distillation residue obtained in step (21-2) to obtain a homogeneous solution.
362 g of a solution were recovered from line 57 by carrying out the same method as step (2-3) of Example 2 with the exception of using the solution and using a reaction time of 16 hours. As a result of analyzing the solution by $^1$H and $^{13}$C-NMR analysis, the solution was found to contain 99% by weight of isophorone diisocyanate. The yield based on 3-aminomethyl-3,5,5-trimethylcyclohexylamine was 90.5%. In addition, there were no substances observed to be adhered to the inside of the thin film evaporator following the reaction. There were no compounds detected in the low boiling point component presumed to have originated from denaturation of 2,4,6-trimethylphenol.

Example 22

(Step 22-1): Production of 3-((3-methylbutyl)oxycarbonylamino-methyl)-3,5,5-trimethylcyclohexylcarbamic Acid (3-methylbutyl) Ester 301.4 g (1.77 mol) of 3-aminomethyl-3,5,5-trimethylcyclohexylamine, 212.4 g (3.4 mol) of urea and 3120 g of 3-methyl-1-butanol were placed in a 10 L volumetric four-mouth flask equipped with a reflux condenser, a thermometer, a stirrer and a gas feed tube. The flask was immersed in an oil bath preheated to 155° C. and the reaction was carried out while introducing nitrogen gas at the rate of 20 L/hr from a ball filter that reached to the bottom of the reaction vessel. Samples of the reaction liquid were suitably collected and subjected to NMR analysis, and the reaction was terminated at the time when 3-aminomethyl-3,5,5-trimethylcyclohexylamine was no longer detected. A solution containing ammonia was distilled from the upper portion of the reaction vessel.

The flask was connected to a rotary evaporator to which was connected an oil bath equipped with a temperature controller, a vacuum pump and a vacuum controller, the oil bath temperature was set to 130° C., and the low boiling point component was distilled off at a pressure of 0.02 kPa to obtain a distillation residue inside the flask. When the distillation residue was analyzed by liquid chromatography, the distillation residue was found to contain 99.0% by weight of 3-((3-methylbutyl)oxycarbonylamino-methyl)-3,5,5-trimethylcyclohexylcarbamic acid (3-methylbutyl) ester. In addition, when the distillation residue was analyzed by gas chromatography, it was found to contain urea at a molar ratio of 0.005 to the 3-((3-methylbutyl)oxycarbonylamino-methyl)-3,5,5-trimethylcyclohexylcarbamic acid (3-methylbutyl) ester.

Step (22-2): Production of Isophorone Diisocyanate by Thermal Decomposition of 3-((3-methylbutyl) oxycarbonylamino-methyl)-3,5,5-trimethylcyclohexylcarbamic Acid (3-methylbutyl) Ester 1305 g of 2-tert-butylphenol and 54.9 g of dibutyl tin dilaurate were added to the distillation residue obtained in step (22-1) to obtain a homogeneous solution. When this was analyzed by gas chromatography, the solution was found to contain urea at a stoichiometric ratio of 0.0010 to 2-tert-butylphenol. 347 g of a solution were recovered from line 57 by carrying out the same method as Step (2-3) of Example 2 using the solution. As a result of analyzing by $^1$H and $^{13}$C-NMR analysis, the solution was found to contain 99% by weight of isophorone diisocyanate. The yield based on 3-aminomethyl-3,5,5-trimethylcyclohexylamine was 88.4%. In addition, there were no substances observed to be adhered to the inside of the thin film evaporator following the reaction. There were no butenes detected in the low boiling point component presumed to have originated from denaturation of 2-tert-butylphenol.

Example 23

Step (23-1): Production of Bis(3-methylbutyl)-4,4'-methylene-dicyclohexylcarbamate 2124 g (10.5 mol) of bis(3-methylbutyl) carbonate and 368.1 g (1.75 mol) of 4,4'-methylenebis(cyclohexylamine) (Aldrich Corp., USA) were placed in a 5 L volumetric four-mouth flask, a stirrer was placed in the flask, and a Dimroth condenser and a three-way valve were attached to the flask. After replacing the inside of the system with nitrogen, the four-mouth flask was immersed in an oil bath heated to 100° C. followed by the addition of 6.8 g of sodium methoxide to start the reaction. Samples of the reaction liquid were suitably collected and subjected to NMR analysis, and the reaction was terminated at the time when 4,4'-methylenebis(cyclohexylamine) was no longer detected. The resulting solution was supplied to a column which was packed with an acidic sulfonic acid ion exchange resin (Amberlyst-15 (spheres), Rohm and Haas Co.) adjusted by removing moisture and warmed to 65° C. with an external jacket, to obtain a solution in which the sodium methoxide had been neutralized. As a result of analyzing the solution by liquid chromatography, the solution was found to contain 30.6% by weight of bis(3-methylbutyl)-4,4'-methylene-dicyclohexylcarbamate.

Step (23-2): Distillation of Low Boiling Point Component 1658 g of a distillate were obtained when the low boiling point component was distilled off in the same manner as step (1-1) of Example 1 using the solution obtained in step (23-1) instead of the solution obtained in step (1-1). As a result of analyzing by gas chromatography, the distillate was found to be a solution containing 82.2% by weight of bis(3-methylbutyl) carbonate and 17.8% by weight of 3-methyl-1-butanol. In addition, as a result of analyzing the distillation residue obtained in the flask by liquid chromatography, the distillation residue was found contain 98.3% by weight of bis(3-methylbutyl)-4,4'-methylene-dicyclohexylcarbamate. In addition, when the distillation residue was analyzed by gas chromatography, the distillation residue was found to contain bis(3-methylbutyl) carbonate at a molar ratio of 0.012 to bis(3-methylbutyl)-4,4'-methylene-dicyclohexylcarbamate.

Step (23-3): Production of 4,4'-methylene-di(cyclohexylisocyanate) by Thermal Decomposition of Bis (3-methylbutyl)-4,4'-methylene-dicyclohexylcarbamate 1305 g of 2,4-di-tert-amylphenol and 54.9 g of dibutyl tin dilaurate were added to the distillation residue obtained in step (23-2) to obtain a homogeneous solution. When this was analyzed by gas chromatography, the solution was found to contain bis(3-methylbutyl) carbonate at a stoichiometric ratio of 0.0022 to 2,4-di-tert-amylphenol. 404 g of a solution were recovered from line 57 by carrying out the same method as step (2-3) of Example 2 using the solution. As a result of analyzing the solution by $^1$H and $^{13}$C-NMR analysis, the solution was found to contain 99% by weight of 4,4'-methylene-di(cyclohexylisocyanate). The yield based on 4,4'-methylenebis(cyclohexylamine) was 88.2%. In addition, there were no substances observed to be adhered to the inside of the thin film evaporator following the reaction. There were no pentenes detected in the low boiling point component presumed to have originated from denaturation of 2,4-di-tert-amylphenol.

Example 24

Step (24-1): Production of Bis(n-butyl)-4,4'-methylene-dicyclohexylcarbamate

The same method as step (23-1) of Example 23 was carried out with the exception of using 2090 g (12.0 mol) of dibutyl carbonate instead of bis(3-methylbutyl) carbonate, and using 420.7 g (2.0 mol) of 4,4'-methylenebis(cyclohexylamine) and 11.6 g of sodium methoxide to obtain a solution containing 32.4% by weight of bis(n-butyl)-4,4'-methylene-dicyclohexylcarbamate Step (24-2): Distillation of Low Boiling Point Component 1683 g of a distillate were obtained when distillation of the low boiling point component was carried out in the same manner as step (1-1) of Example 1 using the solution obtained in step (24-1) instead of the solution obtained in step (1-1). When analyzed by gas chromatography, the distillate was found to be a solution containing 82.7% by weight of dibutyl carbonate and 17.2% by weight of 1-butanol. In addition, when the distillation residue obtained in the flask was analyzed by liquid chromatography, the distillation residue was found to contain 97.6% by weight of di(n-butyl)-4,4'-methylene-dicyclohexylcarbamate. In addition, when the distillation residue was analyzed by gas chromatography, the distillation residue was found to contain dibutyl carbonate at a molar ratio of 0.007 to di(n-butyl)-4,4'-methylene-dicyclohexylcarbamate.

Step (24-3): Production of 4,4'-methylene-di(cyclohexylisocyanate) by Thermal Decomposition of Di(n-butyl)-4,4'-methylene-dicyclohexylcarbamate 1215 g of 2,6-xylenol and 62.9 g of dibutyl tin dilaurate were added to the distillation residue obtained in step (24-2) to obtain a homogeneous solution. When this was analyzed by gas chromatography, the solution was found to contain dibutyl carbonate at a stoichiometric ratio of 0.0014 to 2,6-xylenol. 470 g of a solution were recovered from line 57 by carrying out the same method as step (2-3) of Example 2 using the solution. As a result of analyzing the solution by $^1H$ and $^{13}C$-NMR analysis, the solution was found to contain 99% by weight of 4,4'-methylene-di(cyclohexylisocyanate). The yield based on 4,4'-methylenebis(cyclohexylamine) was 89.6%. In addition, there were no substances observed to be adhered to the inside of the thin film evaporator following the reaction. There were no compounds detected in the low boiling point component presumed to have originated from denaturation of 2,6-xylenol.

Example 25

Step (25-1): Production of Dimethyl-4,4'-methylene-dicyclohexylcarbamate

The same method as step (23-1) of Example 23 was carried out with the exception of using 1390 g (15.4 mol) of dimethyl carbonate instead of bis(3-methylbutyl) carbonate, using 462.8 g (2.2 mol) of 4,4'-methylenebis(cyclohexylamine) and 8.5 g of sodium methoxide and carrying out neutralization treatment with an ion exchange resin to obtain a solution containing 38.5% by weight of dimethyl-4,4'-methylene-dicyclohexylcarbamate.

Step (25-2): Distillation of Low Boiling Point Component 1134 g of a distillate were obtained when distillation of the low boiling point component was carried out in the same manner as step (1-1) of Example 1 using the solution obtained in step (25-1) instead of the solution obtained in step (1-1). When analyzed by gas chromatography, the distillate was found to be a solution containing 87.6% by weight of dimethyl carbonate and 12.3% by weight of methanol. In addition, when the distillation residue obtained in the flask was analyzed by liquid chromatography, the distillation residue was found to contain 98.6% by weight of dimethyl-4,4'-methylene-dicyclohexylcarbamate. In addition, when the distillation residue was analyzed by gas chromatography, the distillation residue was found to contain dimethyl carbonate at a molar ratio of 0.002 to dimethyl-4,4'-methylene-dicyclohexylcarbamate.

Step (25-3): Production of 4,4'-methylene-di(cyclohexylisocyanate) by Thermal Decomposition of Dimethyl-4,4'-methylene-dicyclohexylcarbamate 1487 g of 2,4,6-trimethylphenol and 69.0 g of dibutyl tin dilaurate were added to the distillation residue obtained in step (25-2) to obtain a homogeneous solution. When this was analyzed by gas chromatography, the solution was found to contain dimethyl carbonate at a stoichiometric ratio of 0.00040 to 2,4,6-trimethylphenol. 487 g of a solution were recovered from line 57 by carrying out the same method as step (2-3) of Example 2 using the solution. As a result of analyzing the solution by $^1H$ and $^{13}C$-NMR analysis, the solution was found to contain 99% by weight of 4,4'-methylene-di(cyclohexylisocyanate). The yield based on 4,4'-methylenebis(cyclohexylamine) was 84.4%. In addition, there were no substances observed to be adhered to the inside of the thin film evaporator following the reaction. There were no compounds detected in the low boiling point component presumed to have originated from denaturation of 2,4,6-trimethylphenol.

Example 26

Step (26-1): Production of Bis(3-methylbutyl)-4,4'-methylene-dicyclohexylcarbamate 420.7 g (2.0 mol) of 4,4'-methylenebis(cyclohexylamine), 240 g (2.0 mol) of urea and 3526 g of 3-methyl-1-butanol were placed in a 10 L volumetric four-mouth flask equipped with a reflux condenser, a thermometer, a stirrer and a gas feed tube. The flask was immersed in an oil bath (OBH-24, Masuda Corp., Japan) preheated to 155° C. and the reaction was carried out while introducing nitrogen gas at the rate of 20 L/hr from a ball filter that reached to the bottom of the reaction vessel. Samples of the reaction liquid were suitably collected and subjected to NMR analysis, and the reaction was terminated at the time when 4,4'-methylenebis(cyclohexylamine) was no longer detected. A solution containing ammonia was distilled from the upper portion of the reaction vessel.

The flask was connected to a rotary evaporator to which was connected an oil bath equipped with a temperature controller, a vacuum pump and a vacuum controller, the oil bath temperature was set to 130° C., and the low boiling point component was distilled off at a pressure of 0.02 kPa to obtain a distillation residue inside the flask. When the distillation residue was analyzed by liquid chromatography, the distillation residue was found to contain 99.0% by weight of bis(3-methylbutyl)-4,4'-methylene-dicyclohexylcarbamate. In addition, when the distillation residue was analyzed by gas chromatography, it was found to contain urea at a molar ratio of 0.004 to the bis(3-methylbutyl)-4,4'-methylene-dicyclohexylcarbamate.

Step (26-2): Production of 4,4'-methylene-di(cyclohexylisocyanate) by Thermal Decomposition of Bis(3-methylbutyl)-4,4'-methylene-dicyclohexylcarbamate 1765 g of 2-tert-butylphenol and 61.9 g of dibutyl tin dilaurate were added to the distillation residue obtained in step (26-1) to obtain a homogeneous solution. When this was analyzed by gas chromatography, the solution was found to contain urea at a stoichiometric ratio of 0.00067 to 2-tert-butylphenol. 452 g of a solution were recovered from line 57 by carrying out the same method as Step (2-3) of Example 2 using the solution. As a result of analyzing by $^1$H and $^{13}$C-NMR analysis, the solution was found to contain 99% by weight of 4,4'-methylene-di(cyclohexylisocyanate). The yield based on 4,4'-methylene-di(cyclohexylamine) was 86.1%. In addition, there were no substances observed to be adhered to the inside of the thin film evaporator following the reaction. There were no butenes detected in the low boiling point component presumed to have originated from denaturation of 2-tert-butylphenol.

Example 27

Step (27-1): Production of Toluene-2,4-dicarbamic Acid Bis(3-methylbutyl) Ester 2791 g (13.8 mol) of bis(3-methylbutyl) carbonate and 281 g (2.3 mol) of 2,4-toluenediamine (Aldrich Corp., USA) were placed in a 5 L volumetric four-mouth flask, a stirrer was placed in the flask, and a Dimroth condenser and a three-way valve were attached to the flask. After replacing the inside of the system with nitrogen, the four-mouth flask was immersed in an oil bath heated to 80° C. followed by the addition of 13.3 g of sodium methoxide (28% methanol solution) to start the reaction. Samples of the reaction liquid were suitably collected and subjected to NMR analysis, and the reaction was terminated at the time when 2,4-toluenediamine was no longer detected. The resulting solution was supplied to a column which was packed with an acidic sulfonic acid ion exchange resin (Amberlyst-15 (spheres), Rohm and Haas Co.) adjusted by removing moisture and warmed to 80° C. with an external jacket, to obtain a solution in which the sodium methoxide had been neutralized. As a result of analyzing the solution by liquid chromatography, the solution was found to contain 25.6% by weight of toluene-2,4-dicarbamic acid bis(3-methylbutyl) ester.

Step (27-2): Distillation of Low Boiling Point Component 2268 g of a distillate were obtained when the low boiling point component was distilled off in the same manner as step (1-1) of Example 1 using the solution obtained in step (27-1) instead of the solution obtained in step (1-1). As a result of analyzing by gas chromatography, the distillate was found to be a solution containing 82.6% by weight of bis(3-methylbutyl) carbonate and 17.1% by weight of 3-methyl-1-butanol. In addition, as a result of analyzing the distillation residue obtained in the flask by liquid chromatography, the distillation residue was found contain 96.7% by weight of toluene-2,4-dicarbamic acid bis(3-methylbutyl) ester. In addition, when the distillation residue was analyzed by gas chromatography, the distillation residue was found to contain bis(3-methylbutyl) carbonate at a molar ratio of 0.010 to toluene-2,4-dicarbamic acid bis(3-methylbutyl) ester.

Step (27-3): Production of Toluene-2,4-diisocyanate by Thermal Decomposition of Toluene-2,4-dicarbamic Acid Bis(3-methylbutyl) Ester 2639 g of 2,4-di-tert-amylphenol and 71.2 g of dibutyl tin dilaurate were added to the distillation residue obtained in step (27-2) to obtain a homogeneous solution. When this was analyzed by gas chromatography, the solution was found to contain bis(3-methylbutyl) carbonate at a stoichiometric ratio of 0.0020 to 2,4-di-tert-amylphenol.

368 g of a solution were recovered from line 32 by carrying out the same method as step (1-3) of Example 1 with the exception of using the solution and using a reaction time of 14 hours. As a result of analyzing the solution by $^1$H and $^{13}$C-NMR analysis, the solution was found to contain 99% by weight of toluene-2,4-diisocyanate. The yield based on 2,4-toluenediamine was 92.1%. In addition, there were no substances observed to be adhered to the inside of the thin film evaporator following the reaction. There were no pentenes detected in the low boiling point component presumed to have originated from denaturation of 2,4-di-tert-amylphenol.

Example 28

Step (28-1): Production of Toluene-2,4-dicarbamic Acid Di(n-butyl) Ester

The same method as step (27-1) of Example 27 was carried out with the exception of using 1655 g (9.5 mol) of dibutyl carbonate instead of bis(3-methylbutyl) carbonate and using 232 g (1.9 mol) of 2,4-toluenediamine and 3.7 g of sodium methoxide (28% methanol solution) to obtain a solution containing 32.1% by weight of toluene-2,4-dicarbamic acid di(n-butyl) ester.

Step (28-2): Distillation of Low Boiling Point Component 1273 g of a distillate were obtained when distillation of the low boiling point component was carried out in the same manner as step (1-1) of Example 1 using the solution obtained in step (28-1) instead of the solution obtained in step (1-1). When analyzed by gas chromatography, the distillate was found to be a solution containing 78.3% by weight of dibutyl carbonate and 21.7% by weight of 1-butanol. In addition, when the distillation residue obtained in the flask was analyzed by liquid chromatography, the distillation residue was found to contain 98.3% by weight of toluene-2,4-dicarbamic acid di(n-butyl) ester. In addition, when the distillation residue was analyzed by gas chromatography, the distillation residue was found to contain dibutyl carbonate at a molar ratio of 0.007 to toluene-2,4-dicarbamic acid di(n-butyl) ester.

Step (28-3): Production of Toluene-2,4-diisocyanate by Thermal Decomposition of Toluene-2,4-dicarbamic Acid Di(n-butyl) Ester 1148 g of 2,6-dimethylphenol and 59.4 g of cobalt acetate were added to the distillation residue obtained in step (28-2) to obtain a homogeneous solution. When this was analyzed by gas chromatography, the solution was found to contain dibutyl carbonate at a stoichiometric ratio of 0.0014 to 2,6-dimethylphenol.

297 g of a solution were recovered from line 57 by carrying out the same method as step (2-3) of Example 2 using the solution with the exception of using a reaction time of 16 hours. As a result of analyzing the solution by $^1$H and $^{13}$C-NMR analysis, the solution was found to contain 99% by weight of toluene-2,4-diisocyanate. The yield based on 2,4-toluenediamine was 90.0%. In addition, there were no substances observed to be adhered to the inside of the thin film evaporator following the reaction. There were no compounds detected in the low boiling point component presumed to have originated from denaturation of 2,6-dimethylphenol.

Example 29

Step (29-1): Production of Toluene-2,4-dicarbamic Acid Dimethyl Ester

The same method as step (27-1) of Example 27 was carried out with the exception of using 1137 g (12.6 mol) of methyl carbonate instead of bis(3-methylbutyl) carbonate, using 256.6 g (2.10 mol) of 2,4-toluenediamine and 8.1 g of sodium methoxide (28% methanol solution, Wako Pure Chemical Industries, Ltd., Japan), and carrying neutralization treatment with an ion exchange resin to obtain a solution containing 35.3% by weight of toluene-2,4-dicarbamic acid dimethyl ester.

Step (29-2): Distillation of Low Boiling Point Component 895 g of a distillate were obtained when distillation of the low boiling point component was carried out in the same manner as step (1-1) of Example 1 using the solution obtained in step (29-1) instead of the solution obtained in step (1-1). When analyzed by gas chromatography, the distillate was found to be a solution containing 85.1% by weight of dimethyl carbonate and 14.8% by weight of methanol. In addition, when the distillation residue obtained in the flask was analyzed by liquid chromatography, the distillation residue was found to contain 97.9% by weight of toluene-2,4-dicarbamic acid dimethyl ester. In addition, when the distillation residue was analyzed by gas chromatography, the distillation residue was found to contain dimethyl carbonate at a molar ratio of 0.001 to toluene-2,4-dicarbamic acid dimethyl ester.

Step (29-3): Production of Toluene-2,4-diisocyanate by Thermal Decomposition of Toluene-2,4-dicarbamic Acid Dimethyl Ester 1413 g of 2,4,6-trimethylphenol and 65.6 g of dibutyl tin dilaurate were added to the distillation residue obtained in step (29-2) to obtain a homogeneous solution. When this was analyzed by gas chromatography, the solution was found to contain dimethyl carbonate at a stoichiometric ratio of 0.00020 to 2,4,6-trimethylphenol.

321 g of a solution were recovered from line 57 by carrying out the same method as step (2-3) of Example 2 using the solution with the exception of using a reaction time of 15 hours. As a result of analyzing the solution by $^1$H and $^{13}$C-NMR analysis, the solution was found to contain 99% by weight of toluene-2,4-diisocyanate. The yield based on 2,4-toluenediamine was 88.0%. In addition, there were no substances observed to be adhered to the inside of the thin film evaporator following the reaction. There were no compounds detected in the low boiling point component presumed to have originated from denaturation of 2,4,6-trimethylphenol.

Example 30

Step (30-1): Production of Toluene-2,4-dicarbamic Acid Bis(3-methylbutyl) Ester 232.1 g (1.9 mol) of 2,4-toluenediamine, 239.4 g (4.0 mol) of urea and 3349.7 g of 3-methyl-1-butanol were placed in a 10 L volumetric four-mouth flask equipped with a reflux condenser, a thermometer, a stirrer and a gas feed tube. The flask was immersed in an oil bath preheated to 155° C. and the reaction was carried out while introducing nitrogen gas at the rate of 20 L/hr from a ball filter that reached to the bottom of the reaction vessel. Samples of the reaction liquid were suitably collected and subjected to NMR analysis, and the reaction was terminated at the time when 2,4-toluenediamine was no longer detected. A solution containing ammonia was distilled from the upper portion of the reaction vessel.

The flask was connected to a rotary evaporator to which was connected an oil bath equipped with a temperature controller, a vacuum pump and a vacuum controller, the oil bath temperature was set to 130° C., and the low boiling point component was distilled off at a pressure of 0.02 kPa to obtain a distillation residue inside the flask. When the distillation residue was analyzed by liquid chromatography, the distillation residue was found to contain 99.0% by weight of toluene-2,4-dicarbamic acid bis(3-methylbutyl) ester. In addition, when the distillation residue was analyzed by gas chromatography, it was found to contain urea at a molar ratio of 0.003 to the toluene-2,4-dicarbamic acid bis(3-methylbutyl) ester.

Step (30-2): Production of Toluene-2,4-diisocyanate by Thermal Decomposition of Toluene-2,4-dicarbamic Acid Bis(3-methylbutyl) Ester 2613 g of 2,4-di-tert-amylphenol and 58.7 g of dibutyl tin dilaurate were added to the distillation residue obtained in step (30-1) to obtain a homogeneous solution. When this was analyzed by gas chromatography, the solution was found to contain urea at a stoichiometric ratio of 0.00050 to 2,4-di-tert-amylphenol.

285 g of a solution were recovered from line 32 by carrying out the same method as Step (1-3) of Example 1 using the solution with the exception of using a reaction time of 14 hours. As a result of analyzing by $^1$H and $^{13}$C-NMR analysis, the solution was found to contain 99% by weight of toluene-2,4-diisocyanate. The yield based on 2,4-toluenediamine was 86.1%. In addition, there were no substances observed to be adhered to the inside of the thin film evaporator following the reaction. There were no pentenes detected in the low boiling point component presumed to have originated from denaturation of 2,4-di-tert-amylphenol.

Example 31

Step (31-1): Production of N,N'-(4,4'-methanediyl-diphenyl)-biscarbamic Acid Bis(3-methylbutyl) Ester 2184 g (10.8 mol) of bis(3-methylbutyl) carbonate and 357 g (1.8 mol) of 4,4'-methylenedianiline (Aldrich Corp., USA) were placed in a 5 L volumetric four-mouth flask, a stirrer was placed in the flask, and a Dimroth condenser and a three-way valve were attached to the flask. After replacing the inside of the system with nitrogen, the four-mouth flask was immersed in an oil bath heated to 80° C. followed by the addition of 17.4 g of sodium methoxide (28% methanol solution) to start the reaction. Samples of the reaction liquid were suitably collected and subjected to NMR analysis, and the reaction was terminated at the time when 4,4'-methyleneaniline was no longer detected. The resulting solution was supplied to a column which was packed with an acidic sulfonic acid ion exchange resin (Amberlyst-15 (spheres), Rohm and Haas Co.) adjusted by removing moisture and warmed to 80° C. with an external jacket, to obtain a solution in which the sodium methoxide had been neutralized. As a result of analyzing the solution by liquid chromatography, the solution was found to contain 29.7% by weight of N,N'-(4,4'-methanediyl-diphenyl)-biscarbamic acid bis(3-methylbutyl) ester.

Step (31-2): Distillation of Low Boiling Point Component 1772 g of a distillate were obtained when the low boiling point component was distilled off in the same manner as step (1-1) of Example 1 using the solution obtained in step (31-1) instead of the solution obtained in step (1-1). As a result of analyzing by gas chromatography, the distillate was found to be a solution containing 82.3% by weight of bis(3-methylbutyl) carbonate and 17.7% by weight of 3-methyl-1-butanol. In addition, as a result of analyzing the distillation residue obtained in the flask by liquid chromatography, the distillation residue was found contain 96.6% by weight of N,N'-(4,4'-methanediyl-diphenyl)-biscarbamic acid bis(3-methylbutyl) ester. In addition, when the distillation residue was analyzed by gas chromatography, the distillation residue was found to contain bis(3-methylbutyl) carbonate at a molar ratio of 0.014 to N,N'-(4,4'-methanediyl-diphenyl)-biscarbamic acid bis(3-methylbutyl) ester.

Step (31-3): Production of 4,4'-diphenylmethane Diisocyanate by Thermal Decomposition of N,N'-(4,4'-methanediyl-diphenyl)-biscarbamic Acid Bis(3-methylbutyl) Ester 2086 g of 2,4-di-tert-amylphenol and 56.3 g of dibutyl tin dilaurate were added to the distillation residue obtained in step (31-2) to obtain a homogeneous solution. When this was analyzed by gas chromatography, the solution was found to contain bis(3-methylbutyl) carbonate at a stoichiometric ratio of 0.0028 to 2,4-di-tert-amylphenol.

423 g of a solution were recovered from line 57 by carrying out the same method as step (2-3) of Example 2 with the exception of using the solution and using a reaction time of 15 hours. As a result of analyzing the solution by $^1$H and $^{13}$C-NMR analysis, the solution was found to contain 99% by weight of 4,4'-diphenylmethane diisocyanate. The yield based on 4,4'-methylenedianiline was 94.0%. In addition, there were no substances observed to be adhered to the inside of the thin film evaporator following the reaction. There were no pentenes detected in the low boiling point component presumed to have originated from denaturation of 2,4-di-tert-amylphenol.

Example 32

Step (32-1): Production of N,N'-(4,4'-methanediyl-diphenyl)-bis Carbamic Acid Di(n-butyl) Ester The same method as step (31-1) of Example 31 was carried out with the exception of using 1820 g (10.5 mol) of dibutyl carbonate instead of bis(3-methylbutyl) carbonate and using 376.7 g (1.9 mol) of 4,4-methylenedianiline (Aldrich Corp., USA) and 7.3 g of sodium methoxide (28% methanol solution, Wako Pure Chemical Industries, Ltd., Japan) to obtain a solution containing 34.2% by weight of N,N'-(4,4'-methanediyl-diphenyl)-biscarbamic acid di(n-butyl) ester.

Step (32-2): Distillation of Low Boiling Point Component 1435 g of a distillate were obtained when distillation of the low boiling point component was carried out in the same manner as step (1-1) of Example 1 using the solution obtained in step (32-1) instead of the solution obtained in step (1-1). When analyzed by gas chromatography, the distillate was found to be a solution containing 80.6% by weight of dibutyl carbonate and 19.1% by weight of 1-butanol. In addition, when the distillation residue obtained in the flask was analyzed by liquid chromatography, the distillation residue was found to contain 98.1% by weight of N,N'-(4,4'-methanediyl-diphenyl)-biscarbamic acid di(n-butyl) ester. In addition, when the distillation residue was analyzed by gas chromatography, the distillation residue was found to contain dibutyl carbonate at a molar ratio of 0.012 to N,N'-(4,4'-methanediyl-diphenyl)-biscarbamic acid di(n-butyl) ester.

Step (32-3): Production of 4,4'-diphenylmethane Diisocyanate by Thermal Decomposition of N,N'-(4,4'-methanediyl-diphenyl)-biscarbamic Acid Di(n-butyl) Ester 2310 g of 2,6-dimethylphenol and 59.8 g of dibutyl tin dilaurate were added to the distillation residue obtained in step (32-2) to obtain a homogeneous solution. When this was analyzed by gas chromatography, the solution was found to contain dibutyl carbonate at a stoichiometric ratio of 0.0012 to 2,6-dimethylphenol.

430 g of a solution were recovered from line 57 by carrying out the same method as step (2-3) of Example 2 using the solution with the exception of using a reaction time of 15 hours. As a result of analyzing the solution by $^1$H and $^{13}$C-NMR analysis, the solution was found to contain 99% by weight of 4,4'-diphenylmethane diisocyanate. The yield based on 4,4'-methylenedianiline was 90.6%. In addition, there were no substances observed to be adhered to the inside of the thin film evaporator following the reaction. There were no compounds detected in the low boiling point component presumed to have originated from denaturation of 2,6-dimethylphenol.

Example 33

Step (33-1): Production of N,N'-(4,4'-methanediyl-diphenyl)-biscarbamic Acid Dimethyl Ester The same method as step (31-1) of Example 31 was carried out with the exception of using 957 g (10.6 mol) of dimethyl carbonate instead of bis(3-methylbutyl) carbonate, using 396.5 g (2.0 mol) of 4,4'-methylenedianline and 3.9 g of sodium methoxide (28% methanol solution, Wako Pure Chemical Industries, Ltd., Japan), and carrying neutralization treatment with an ion exchange resin to obtain a solution containing 34.2% by weight of N,N'-(4,4'-methanediyl-diphenyl)-biscarbamic acid dimethyl ester.

Step (33-2): Distillation of Low Boiling Point Component 724 g of a distillate were obtained when distillation of the low boiling point component was carried out in the same manner as step (1-1) of Example 1 using the solution obtained in step (33-1) instead of the solution obtained in step (1-1). When analyzed by gas chromatography, the distillate was found to be a solution containing 82.4% by weight of dimethyl carbonate and 17.5% by weight of methanol. In addition, when the distillation residue obtained in the flask was analyzed by liquid chromatography, the distillation residue was found to contain 99.1% by weight of N,N'-(4,4'-methanediyl-diphenyl)-biscarbamic acid dimethyl ester. In addition, when the distillation residue was analyzed by gas chromatography, the distillation residue was found to contain dimethyl carbonate at a molar ratio of 0.002 to N,N'-(4,4'-methanediyl-diphenyl)-biscarbamic acid dimethyl ester.

Step (33-3): Production of 4,4'-diphenylmethane Diisocyanate by Thermal Decomposition of N,N'-(4,4'-methanediyl-diphenyl)-biscarbamic Acid Dimethyl Ester 2714 g of 2,4,6-trimethylphenol and 63.4 g of dibutyl tin dilaurate were added to the distillation residue obtained in step (33-2) to obtain a homogeneous solution. When this was analyzed by gas chromatography, the solution was found to contain dimethyl carbonate at a stoichiometric ratio of 0.0020 to 2,4,6-trimethylphenol.

448 g of a solution were recovered from line 57 by carrying out the same method as step (2-3) of Example 2 using the solution with the exception of using a reaction time of 15 hours. As a result of analyzing the solution by $^1$H and $^{13}$C-NMR analysis, the solution was found to contain 99% by weight of 4,4'-diphenylmethane diisocyanate. The yield based on 4,4'-methylenedianiline was 89.7%. In addition, there were no substances observed to be adhered to the inside of the thin film evaporator following the reaction. There were no compounds detected in the low boiling point component presumed to have originated from denaturation of 2,4,6-trimethylphenol.

Example 34

Step (34-1): Production of N,N'-(4,4'-methanediyl-diphenyl)-biscarbamic Acid Bis(3-methylbutyl) Ester 376.3 g (1.9 mol) of 4,4'-methylenedianiline, 250.8 g (4.2 mol) of urea and 3684 g of 3-methyl-1-butanol were placed in a 10 L volumetric four-mouth flask equipped with a reflux condenser, a thermometer, a stirrer and a gas feed tube. The flask was immersed in an oil bath preheated to 155° C. and the reaction was carried out while introducing nitrogen gas at the rate of 20 L/hr from a ball filter that reached to the bottom of the reaction vessel. Samples of the reaction liquid were suitably collected and subjected to NMR analysis, and the reaction was terminated at the time when 4,4'-methylenedianiline was no longer detected. A solution containing ammonia was distilled from the upper portion of the reaction vessel.

The flask was connected to a rotary evaporator to which was connected an oil bath equipped with a temperature controller, a vacuum pump and a vacuum controller, the oil bath temperature was set to 130° C., and the low boiling point component was distilled off at a pressure of 0.02 kPa to obtain a distillation residue inside the flask. When the distillation residue was analyzed by liquid chromatography, the distillation residue was found to contain 98.4% by weight of N,N'-(4,4'-methanediyl-diphenyl)-biscarbamic acid bis(3-methylbutyl) ester. In addition, when the distillation residue was analyzed by gas chromatography, it was found to contain urea at a molar ratio of 0.007 to the N,N'-(4,4'-methanediyl-diphenyl)-biscarbamic acid bis(3-methylbutyl) ester.

Step (34-2): Production of 4,4'-diphenylmethane Diisocyanate by Thermal Decomposition of N,N'-(4,4'-methanediyl-diphenyl)-biscarbamic Acid Bis(3-methylbutyl) Ester 2304 g of 2,4-di-tert-butylphenol and 58.8 g of dibutyl tin dilaurate were added to the distillation residue obtained in step (34-1) to obtain a homogeneous solution. When this was analyzed by gas chromatography, the solution was found to contain urea at a stoichiometric ratio of 0.0012 to 2,4-di-tert-amylphenol.

419 g of a solution were recovered from line 57 by carrying out the same method as Step (2-3) of Example 2 using the solution with the exception of using a reaction time of 15 hours. As a result of analyzing by $^1$H and $^{13}$C-NMR analysis, the solution was found to contain 99% by weight of 4,4'-diphenylmethane diisocyanate. The yield based on 4,4'-methylenedianiline was 88.2%. In addition, there were no substances observed to be adhered to the inside of the thin film evaporator following the reaction. There were no butenes detected in the low boiling point component presumed to have originated from denaturation of 2,4-di-tert-butylphenol.

Example 35

Figure 4:
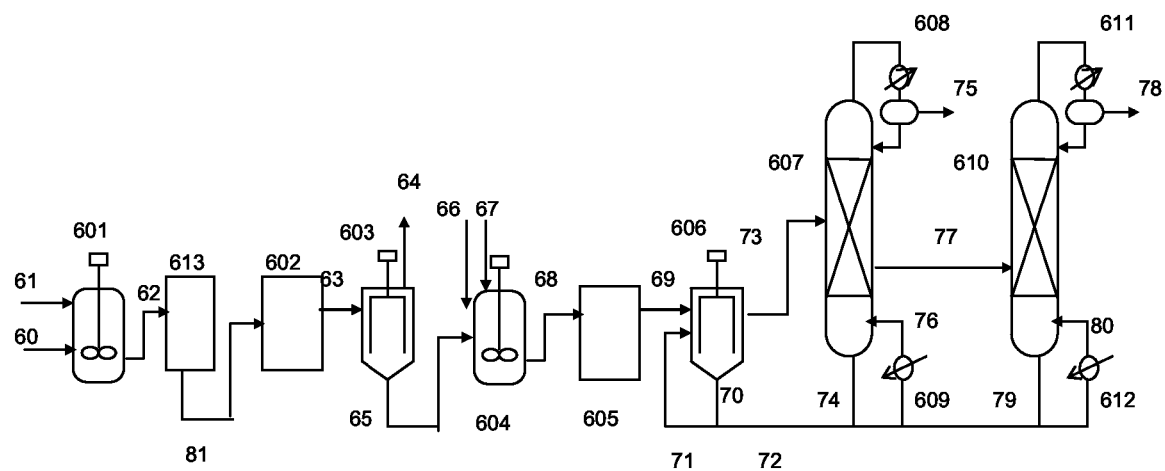

Hexamethylene diisocyanate was produced in a reaction apparatus as shown in FIG. 4.

Step (35-1): Production Process of N,N'-hexanediyl-bis-carbamic Acid Di(3-methylbutyl) Ester A stirring tank 601 (internal volume: 10 L) was heated to 80° C. Bis(3-methylbutyl) carbonate preheated to 80° C. was transferred to the stirring tank 601 from a line 60 at the rate of 589 g/hr with a line 62 closed, and a mixed solution of hexamethylene diamine, 3-methyl-1-butanol and sodium methoxide (28% methanol solution) (mixing ratio: hexamethylene diamine 50 parts/3-methyl-1-butanol 50 parts/sodium methoxide 4.2 parts) was simultaneously transferred from a line 61 at the rate of 128 g/hr. After 5 hours, line 62 was opened with a line 63 closed, the reaction liquid was supplied to an ion exchange resin column 613 which was packed with an acidic sulfonic acid ion exchange resin (Amberlyst-15 (spheres), Rohm and Haas Co.) adjusted by removing moisture and warmed to 80° C. with an external jacket to neutralize the sodium methoxide followed by transfer of the reaction liquid to a tank 602 through a line 81. Line 62 and line 81 were maintained at 80° C. to prevent precipitation of solids from the reaction liquid.

When the reaction liquid transferred to tank 602 was analyzed by liquid chromatography, the reaction liquid was found to contain 25.4% by weight of N,N'-hexanediyl-bis-carbamic acid di(3-methylbutyl) ester.

Step (35-2): Low Boiling Point Component Distillation Process

A thin film distillation apparatus 603 (heat-conducting surface area of 0.2 m$^2$, Kobelco Eco-Solutions Co., Ltd., Japan) was heated to 150° C. and the pressure inside the apparatus was made to be about 0.02 kPa.

The solution stored in tank 602 was transferred to thin film distillation apparatus 603 from line 63 at the rate of 717 g/hr where a low boiling point component contained in the solution was distilled off. The low boiling point component that had been distilled off was extracted from the thin film distillation apparatus 603 via a line 64. On the other hand, a high boiling point component was extracted from the thin film distillation apparatus 603 via a line 65 maintained at 150° C., and transferred to a stirring tank 604 maintained at 120° C. At the same time, 2,4-di-tert-amylphenol was transferred via a line 66 to stirring tank 604 at the rate of 618 g/hr, and dibutyl tin dilaurate was transferred to stirring tank 604 via a line 67 at the rate of 16.7 g/h.

The mixed liquid prepared in stirring tank 604 was transferred to a tank 605 via a line 68 with a line 69 closed, and stored in the tank 605. When the solution stored in the tank 605 was analyzed by liquid chromatography, the solution was found to contain 22.2% by weight of N,N'-hexanediyl-bis-carbamic acid di(3-methylbutyl) ester. In addition, when analyzed by gas chromatography, the solution was found to contain bis(3-methylbutyl)carbonate at a stoichiometric ratio of 0.0024 to 2,4-di-tert-amylphenol.

Step (35-3): Production Process of Hexamethylene Diisocyanate by Thermal Decomposition of N,N'-hexanediyl-bis-carbamic Acid Bis(3-methylbutyl) Ester The solution stored in tank 605 was supplied to a thin film distillation apparatus 606 (heat-conducting surface area of 0.2 m$^2$, Kobelco Eco-Solutions Co., Ltd., Japan) heated to 200° C. and set to an internal pressure of about 1.3 kPa via line 69 at the rate of 818 g/hr. A gaseous component containing hexamethylene diisocyanate, isoamyl alcohol and 2,4-di-tert-amylphenol was extracted from a line 73 provided in the upper portion of the thin film distillation apparatus 606. The gaseous component was introduced into a distillation column 607 where the isoamyl alcohol was separated after which a portion of the high boiling point component was returned to thin film distillation apparatus 606 via a line 71 through a line 70 provided in the bottom of the thin film distillation apparatus 606. The gaseous component containing hexamethylene diisocyanate and 2,4-di-tert-amylphenol was extracted from a line 77 provided in distillation column 607 and introduced into a distillation column 610. Separation of hexamethylene diisocyanate was carried out in the distillation column 610. After carrying out the reaction for 12 hours, 965 g of a solution were recovered from a line 78, and as a result of analyzing by $^1$H and $^{13}$C-NMR analysis, the solution was found to contain 99% by weight of hexamethylene diisocyanate. The yield based on hexamethylene diamine was 90.6%. In addition, there were no substances observed to be adhered to the inside of the thin film evaporator following the reaction. There were no pentenes detected in the low boiling point component presumed to have originated from denaturation of 2,4-di-tert-amylphenol.

Comparative Example 1

Step (A-1): Production of N,N'-hexanediyl-bis-carbamic Acid Di(n-butyl) Ester

The same method as step (1-1) of Example 1 was carried out with the exception of using 2012 g (11.6 mol) of dibutyl carbonate instead of bis(3-methylbutyl) carbonate, and using 244.0 g (2.10 mol) of hexamethylene diamine and 20.3 g of sodium methoxide (28% methanol solution) to obtain a solution containing 28.9% by weight of N,N'-hexanediyl-bis-carbamic acid di(n-butyl) ester.

Step (A-2): Distillation of Low Boiling Point Component 1527 g of a distillate were obtained by carrying out the same method as step (1-2) of Example 1 using the solution obtained in step (A-1) instead of the solution obtained in step (1-1). When analyzed by gas chromatography, the distillate was found to be a solution containing 81.0% by weight of dibutyl carbonate and 19.1% by weight of n-butanol. In addition, when the distillation residue obtained in the flask was analyzed by liquid chromatography, the distillation residue was found to contain 95.3% by weight of N,N'-hexanediyl-bis-carbamic acid di(n-butyl) ester. In addition, when the distillation residue was analyzed by gas chromatography, the distillation residue was found to contain dibutyl carbonate at a molar ratio of 0.006 to N,N'-hexanediyl-bis-carbamic acid di(n-butyl) ester.

Step (A-3): Production of Hexamethylene Diisocyanate by Thermal Decomposition of N,N'-hexanediyl-bis-carbamic Acid Di(n-butyl) Ester 2430 g of benzylbutyl phthalate (guaranteed reagent, Wako Pure Chemical Industries, Ltd., Japan) and 63.1 g of dibutyl tin dilaurate were added to the distillation residue obtained in step (A-2) to obtain a homogeneous solution.

208 g of a solution were recovered from line 32 by carrying out the same method as step (1-3) of Example 1 using the solution with the exception of using a reaction time of 13 hours. As a result of analyzing the solution by $^1$H and $^{13}$C-NMR analysis, the solution was found to contain 99% by weight of hexamethylene diisocyanate. The yield based on hexamethylene diamine was 59.0%. In addition, a black substance observed to be adhered to the inside of the thin film evaporator following the reaction.

Comparative Example 2

Step (B-1): Production of N,N'-hexanediyl-bis-carbamic Acid Di(n-butyl) Ester

The same method as step (1-1) of Example 1 was carried out with the exception of using 1986 g (11.4 mol) of dibutyl carbonate instead of bis(3-methylbutyl) carbonate, and using 22.8 g (1.90 mol) of hexamethylene diamine and 18.3 g of sodium methoxide (28% methanol solution) to obtain a solution containing 26.7% by weight of N,N'-hexanediyl-bis-carbamic acid di(n-butyl) ester.

Step (B-2): Distillation of Low Boiling Point Component 1606 g of a distillate were obtained by carrying out the same method as step (1-2) of Example 1 using the solution obtained in step (B-1) instead of the solution obtained in step (1-1). When analyzed by gas chromatography, the distillate was found to be a solution containing 82.8% by weight of dibutyl carbonate and 17.1% by weight of n-butanol.

The distillation residue obtained in the flask was washed with 6.3 L of n-hexane followed by filtering out a white solid. When this white solid was analyzed by liquid chromatography, the white solid was found to contain 99.8% by weight of N,N'-hexanediyl-bis-carbamic acid di(butyl) ester. In addition, when the white solid was analyzed by gas chromatography, there was no residual dibutyl carbonate detected in the white solid.

Step (B-3): Production of Hexamethylene Diisocyanate by Thermal Decomposition of N,N'-hexanediyl-bis-carbamic Acid Di(n-butyl) Ester 2430 g of benzylbutyl phthalate (guaranteed reagent, Wako Pure Chemical Industries, Ltd., Japan) and 63.1 g of dibutyl tin dilaurate were added to the distillation residue obtained in step (B-2) to obtain a homogeneous solution.

173 g of a solution were recovered from line 32 by carrying out the same method as step (1-3) of Example 1 using the solution with the exception of using a reaction time of 13 hours. As a result of analyzing the solution by $^1$H and $^{13}$C-NMR analysis, the solution was found to contain 99% by weight of hexamethylene diisocyanate. The yield based on hexamethylene diamine was 54.4%. In addition, a black substance observed to be adhered to the inside of the thin film evaporator following the reaction.

Comparative Example 3

Step (C-1): Production of
N,N'-hexanediyl-bis-carbamic Acid Di(n-butyl) Ester

The same method as step (1-1) of Example 1 was carried out with the exception of using 1955 g (11.2 mol) of dibutyl carbonate, 217.3 g (1.87 mol) of hexamethylene diamine and 18.0 g of sodium methoxide (28% methanol solution, Wako Pure Chemical Industries, Ltd., Japan) to obtain a solution containing 26.7% by weight of N,N'-hexanediyl-bis-carbamic acid di(n-butyl) ester.

Step (C-2): Distillation of Low Boiling Point Component 1600 g of a distillate were obtained by carrying out the same method as step (1-2) of Example 1 using the solution obtained in step (C-1) instead of the solution obtained in step (1-1). When analyzed by gas chromatography, the distillate was found to be a solution containing 82.8% by weight of dibutyl carbonate and 17.1% by weight of n-butanol.

The distillation residue obtained in the flask was washed with 5.9 L of n-hexane followed by filtering out a white solid. When this white solid was analyzed by liquid chromatography, the white solid was found to contain 99.8% by weight of N,N'-hexanediyl-bis-carbamic acid di(butyl) ester. In addition, when the white solid was analyzed by gas chromatography, there was no residual dibutyl carbonate detected in the white solid.

Step (C-3): Production of Hexamethylene Diisocyanate by Thermal Decomposition of
N,N'-hexanediyl-bis-carbamic Acid Di(n-butyl) Ester 2430 g of benzylbutyl phthalate (guaranteed reagent, Wako Pure Chemical Industries, Ltd., Japan) and 63.1 g of dibutyl tin dilaurate were added to the distillation residue obtained in step (C-2) to obtain a homogeneous solution.

159 g of a solution were recovered from line 32 by carrying out the same method as step (1-3) of Example 1 using the solution with the exception of storing the solution for 150 hours in feed tank 201 heated to 80° C. and using a reaction time of 13 hours. As a result of analyzing the solution by $^1$H and $^{13}$C-NMR analysis, the solution was found to contain 99% by weight of hexamethylene diisocyanate. The yield based on hexamethylene diamine was 50.7%. In addition, a black substance observed to be adhered to the inside of the thin film evaporator following the reaction.

INDUSTRIAL APPLICABILITY

Since the isocyanate production process according to the present invention allows isocyanate to be efficiently produced without using extremely toxic phosgene, the process for producing the isocyantes according to the present invention is highly industrially useful and has high commercial value.

We claim:
1. A process for producing an isocyanate by subjecting a carbamic acid ester to a decomposition reaction,
wherein the decomposition reaction is carried out in the presence of an aromatic hydroxy compound having a substituent at one or more ortho positions relative to a hydroxy group, and the substituent represents a group other than a hydrogen atom, the group being an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy and the aralkyl groups containing an atom selected from carbon, oxygen and nitrogen atoms; and
the carbamic acid ester is an aliphatic carbamic acid ester represented by the following formula (3):

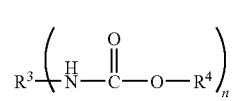

(wherein $R^3$ represents a group selected from the group consisting of an aliphatic group having 1 to 20 carbon atoms and an aromatic group having 6 to 20 carbon atoms, the aliphatic and the aromatic groups containing an atom selected from carbon and oxygen atoms, and the groups having a valence equal to n,
$R^4$ represents an aliphatic group which has 1 to 20 carbon atoms, and which has an atom selected from carbon and oxygen atoms, and
n represents an integer of 1 to 10).
2. The process according to claim 1, wherein the aromatic hydroxy compound having the substituent is a compound represented by the following formula (1):

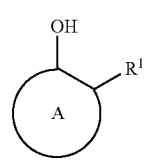

(wherein ring A represents an aromatic hydrocarbon which has 6 to 20 carbon atoms, and which may has a substituent, the ring A being monocyclic or multicyclic,
$R^1$ represents or a hydroxyl group or a group other than a hydrogen atom, the group being an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy and the aralkyl groups containing an atom selected from carbon, oxygen and nitrogen atoms, and $R^1$ may bond with A to form a ring structure).
3. The process according to claim 2, wherein the aromatic hydroxy compound is a compound represented by the following formula (2):

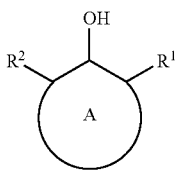

(2)

(wherein ring A and $R^1$ are the same as defined above,
$R^2$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 atoms, the above groups containing an atom selected from carbon, oxygen and nitrogen atoms, or a hydrogen atom or a hydroxyl group, and $R^2$ may bond with A to form a ring structure).

4. The process according to claim 3, wherein in formula (2) above, a total number of carbon atoms constituting $R^1$ and $R^2$ is from 2 to 20.

5. The process according to claim 2 or 3, wherein the ring A of the aromatic hydroxy compound is a structure containing at least one structure selected from the group consisting of a benzene ring, a naphthalene ring and an anthracene ring.

6. The process according to claim 1, wherein the aliphatic carbamic acid ester is an aliphatic polycarbamic acid ester.

7. The process according to claim 1, wherein the aliphatic carbamic acid ester is a compound represented by the formula (3) wherein $R^3$ represents a group selected from the group consisting of an alkyl group having 1 to 20 carbon atoms and a cycloalkyl group having 5 to 20 carbon atoms.

8. The process according to claim 1, wherein the decomposition reaction is carried out in the presence of the aromatic hydroxy compound having the substituent and a carbonic acid derivative.

9. The process according to claim 8, wherein the carbonic acid derivative is a compound represented by the following formula (4):

(8)

(wherein each of X and Y independently represents an aliphatic alkoxy group having 1 to 20 carbon atoms, an aryloxy group having 6 to 20 carbon atoms, an aralkyloxy group having 7 to 20 carbon atoms or an amino group having 0 to 20 carbon atoms).

10. The process according to claim 9, wherein the carbonic acid derivative is carbonic acid ester or urea compound.

11. The process according to claim 10, wherein the carbonic acid derivative is a carbonic acid ester represented by the following formula (5):

(5)

(wherein each of $R^5$ and $R^6$ independently represents an aliphatic group having 1 to 20 carbon atoms, an aryl group having 6 to 20 carbon atoms or an aralkyl group having 7 to 20 carbon atoms, the aliphatic, the aryl and the aralkyl groups containing an atom selected from carbon and oxygen atoms).

12. The process according to claim 10, wherein the urea compound is urea.

13. The process according to claim 1, wherein the decomposition reaction is a thermal decomposition reaction.

14. The process according to claim 1, wherein the aliphatic carbamic acid ester is supplied to a reaction vessel in which the decomposition reaction is carried out in a form of a mixture with the aromatic hydroxy compound having the substituent.

15. The process according to claim 1, wherein the aliphatic carbamic acid ester is supplied to a reaction vessel in which the decomposition reaction is carried out in a form of a mixture with the carbonic acid derivative.

16. The process according to claim 15, wherein the aliphatic carbamic acid ester is supplied to a reaction vessel in which the decomposition reaction is carried out in a form of a mixture with the carbonic acid derivative and the aromatic hydroxy compound having the substituent.

17. The process according to claim 14 or 15, wherein a low boiling point component formed by the decomposition reaction is extracted from the reaction vessel in a form of a gaseous component, and all or a portion of a solution containing the aliphatic carbamic acid ester and/or the aromatic hydroxy compound having the substituent is extracted from a bottom of the reaction vessel.

18. The process according to claim 10, wherein the aromatic hydroxy compound is selected from a group consisting of 2,4-di-tert-amylphenol; 2,6-dimethyphenol; 2,4,6-trimethylphenol; 2,4-di-tert-butylphenol; 2-tert-butylphenol; 2-ethoxyphenol; 3,6-dimethylphenol; 2-phenylphenol; 2,4-bis(α,α-dimethylbenzyl)phenol; nonylphenol; phenol; and 2,6-xylenol.

* * * * *